(12) United States Patent
Robison

(10) Patent No.: US 6,395,889 B1
(45) Date of Patent: May 28, 2002

(54) NUCLEIC ACID MOLECULES ENCODING HUMAN PROTEASE HOMOLOGS

(75) Inventor: Keith E. Robison, Wilmington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/392,184

(22) Filed: Sep. 9, 1999

(51) Int. Cl.[7] .................. C12N 15/57; C12N 15/12; C12N 9/64; C12N 15/79
(52) U.S. Cl. .............. 536/23.2; 536/23.5; 435/69.1; 435/252.3; 435/320.1
(58) Field of Search .................. 536/23.2, 23.5; 435/6, 226, 69.1, 252.3

(56) References Cited

U.S. PATENT DOCUMENTS

| | | | | |
|---|---|---|---|---|
| 5,552,526 A | * | 9/1996 | Nakamura et al. | 530/350 |
| 5,883,241 A | * | 3/1999 | Docherty et al. | 536/23.2 |
| 5,990,293 A | * | 11/1999 | Docherty et al. | 536/23.1 |

FOREIGN PATENT DOCUMENTS

| | | | | |
|---|---|---|---|---|
| EP | 0874050 A2 | * | 10/1998 | C12N/15/15 |
| WO | WO-98/55643 A1 | * | 12/1998 | C12P/21/02 |
| WO | WO-98/56804 A1 | * | 12/1998 | C07H/21/02 |
| WO | WO-99/07850 A1 | * | 2/1999 | C12N/15/12 |
| WO | WO-99/37660 A1 | * | 7/1999 | C07H/21/04 |

OTHER PUBLICATIONS

Vazquez, F., et al., 1999, "METH–1, a human ortholog of ADAMTS–1, and METH–2 are members of a new family of proteins with angio–inhibitory activity", The Journal of Biological Chemistry, vol. 274, No. 33, pp. 23349–23357.*
Descriptors of Protease Classes in Prosite and Pfam Databases.

* cited by examiner

Primary Examiner—Ponnathapu Achutamurthy
Assistant Examiner—William W. Moore
(74) Attorney, Agent, or Firm—Alston & Bird LLP

(57) ABSTRACT

The invention relates to polynucleotides encoding newly identified protease homologs. The invention also relates to the proteases. The invention further relates to methods using the protease polypeptides and polynucleotides as a target for diagnosis and treatment in protease-mediated disorders. The invention further relates to drug-screening methods using the protease polypeptides and polynucleotides to identify agonists and antagonists for diagnosis and treatment. The invention further encompasses agonists and antagonists based on the protease polypeptides and polynucleotides. The invention further relates to procedures for producing the protease polypeptides and polynucleotides.

1 Claim, No Drawings

SEQUENCE LISTING

<160> NUMBER OF SEQ ID NOS: 33

<210> SEQ ID NO 1
<211> LENGTH: 4858
<212> TYPE: DNA
<213> ORGANISM: Homo sapiens
<220> FEATURE:
<221> NAME/KEY: misc_feature
<222> LOCATION: (1)...(4858)
<223> OTHER INFORMATION: reprolysin (ADAM family of metalloprotease)
<221> NAME/KEY: misc_feature
<222> LOCATION: (1)...(4858)
<223> OTHER INFORMATION: n = A,T,C or G

<400> SEQUENCE: 1

```
ccacgcgtcc gagcggctcc gagccagggg ctattgcaaa gccagggtgc g ctaccggac      60
ggagagggga gagccctgag cagagtgagc aacatcgcag ccaaggcgga g gccgaagag     120
gggcgccagg caccaatctc cgcgttgcct cagccccgga ggcgcccag a gcgcttctt     180
gtcccagcag agccactctg cctgcgcctg cctctcagtg tctccaactt t gcgctggaa     240
gaaaaacttc ccgcgcgccg gcagaactgc agcgcctcct cttagtgact c cgggagctt     300
cggctgtagc cggctctgcg cgcccttcca acgaataata gaaattgtta a ttttaacaa     360
tccagagcag gccaacgagg ctttgctctc ccgacccgaa ctaaagctcc c tcgctccgt     420
gcgctgctac gagcggtgtc tcctgggggct ccaatgcagc gagctgtgcc c gagggggtc     480
ggaaggcgca agctgggcag cgacatgggg aacgcggagc gggctccggg g tctcggagc     540
tttgggcccg tacccacgct gctgctgctc gccgcggcgc tactggccgt g tcggacgca     600
ctcgggcgcc cctccgagga ggacgaggag ctagtggtgc cggagctgga g cgcgccccg     660
ggacacggga ccacgcgcct ccgcctgcac gcctttgacc agcagctgga t ctggagctg     720
cggcccgaca gcagcttttt ggcgcccggc ttcacgctcc agaacgtggg g cgcaaatcc     780
gggtccgaga cgccgcttcc ggaaaccgac ctggcgcact gcttctactc c ggcaccgtg     840
aatggcgatc ccagctcggc tgccgccctc agcctctgcg agggcgtgcg c ggcgccttc     900
tacctgctgg gggaggcgta tttcatccag ccgctgcccg ccgccagcga g cgcctcgcc     960
accgccgccc caggggagaa gccgccggca ccactacagt tccacctcct g cggcggaat    1020
cggcagggcg acgtaggcgg cacgtgcggg gtcgtggacg acgagccccg g ccgactggg    1080
aaagcggaga ccgaagacga ggacgaaggg actgagggcg aggacgaagg g cctcagtgg    1140
tcgccgcagg acccggcact gcaaggcgta ggacagccca caggaactgg a agcataaga    1200
aagaagcgat ttgtgtccag tcaccgctat gtggaaacca tgcttgtggc a gaccagtcg    1260
atggcagaat tccacggcag tggtctaaag cattaccttc tcaacgttgt t tcggtggc    1320
agccagattg tacaaacacc ccagcattcg taattcagtt agcctggtgg t ggtgaagat    1380
```

-continued

```
cttggtcatc cacgatgaac agaaggggcc ggaagtgacc tccaatgctg c cctcactct    1440 gcggaacttt tgcaactggc agaagcagca caacccaccc agtgaccggg a tgcagagca    1500 ctatgacaca gcaattcttt tcaccagaca ggacttgtgt gggtcccaga c atgtgatac    1560 tcttgggatg gctgatgttg gaactgtgtg tgatccgagc agaagctgct c cgtcataga    1620 agatgatggt ttacaagctg ccttcaccac agcccatgaa ttaggccacg t gtttaacat    1680 gccacatgat gatgcaaagc agtgtgccag ccttaatggt gtgaaccagg a ttcccacat    1740 gatggcgtca atgctttcca acctggacca cagccagcct tggtctcctt g cagtgccta    1800 catgattaca tcatttctgg ataatggtca tggggaatgt ttgatggaca a gcctcagaa    1860 tcccatacag ctcccaggcg atctccctgg cacctcgtac gatgccaacc g gcagtgcca    1920 gtttacattt ggggaggact ccaaacactg ccctgatgca gccagcacat g tagcacctt    1980 gtggtgtacc ggcacctctg gtggggtgct ggtgtgtcaa accaaacact t cccgtgggc    2040 ggatggcacc agctgtggag aagggaaatg gtgtatcaac ggcaagtgtg t gaacaaaac    2100 cgacagaaag cattttgata cgccttttca tggaagctgg ggaatgtggg g gccttgggg    2160 agactgttcg agaacgtgcg gtggaggagt ccagtacacg atgagggaat g tgacaaccc    2220 agtcccaaag aatggaggga agtactgtga aggcaaacga gtgcgctaca g atcctgtaa    2280 ccttgaggac tgtccagaca ataatggaaa aacctttaga gaggaacaat g tgaagcaca    2340 caacgagttt tcaaaagctt cctttgggag tgggcctgcg gtggaatgga t tcccaagta    2400 cgctggcgtc tcaccaaagg acaggtgcaa gctcatctgc caagccaaag g cattggcta    2460 cttcttcgtt ttgcagccca aggttgtaga tggtactcca tgtagcccag a ttccacctc    2520 tgtctgtgtg caaggacagt gtgtaaaagc tggttgtgat cgcatcatag a ctccaaaaa    2580 gaagtttgat aaatgtggtg tttgcggggg aaatggatct acttgtaaaa a aatatcagg    2640 atcagttact agtgcaaaac ctggatatca tgatatcatc acaattccaa c tggagccac    2700 caacatcgaa gtgaaacagc ggaaccagag gggatccagg aacaatggca g ctttcttgc    2760 catcaaagct gctgatggca catatattct taatggtgac tacactttgt c caccttaga    2820 gcaagacatt atgtacaaag gtgttgtctt gaggtacagc ggctcctctg c ggcattgga    2880 aagaattcgc agctttagcc ctctcaaaga gcccttgacc atccaggttc t tactgtggg    2940 caatgccctt cgacctaaaa ttaaatacac ctacttcgta agaagaagaa g ggaatcttt    3000 caatgctatc cccactttt cagcatgggt cattgaagag tggggcgaat g ttctaagtc    3060 atgtgaattg ggttggcaga agactggt agaatgccga gacattaatg g acagcctgc    3120 ttccgagtgt gcaaggaag tgaagccagc cagcaccaga ccttgtgcag a ccatccctg    3180 cccccagtgg cagctggggg agtggtcatc atgttctaag acctgtggga g ggttacaa    3240 aaaaagaagc ttgaagtgtc tgtcccatga tggaggggtg ttatctcatg a gagctgtga    3300 tcctttaaag aaacctaaac atttcataga cttttgcaca atggcagaat g cagttaagt    3360 ggtttaagtg gtgttagctt tgagggcaag gcaaagtgag gaagggctgg t gcagggaaa    3420 gcaagaaggc tggagggatc cagcgtatct tgccagtaac cagtgaggtg t atcagtaag    3480 gtgggattat gggggtagat agaaaaggag ttgaatcatc agagtaaact g ccagttgca    3540 aatttgatag gatagttagt gaggattatt aacctctgag cagtgatata g cataataaa    3600 gccccgggca ttattattat tatttctttt gttacatcta ttacaagttt a gaaaaaaca    3660 aagcaattgt caaaaaaagt tagaactatt acaacccctg tttcctggta c ttatcaaat    3720 acttagtatc atgggggttg ggaaatgaaa agtaggagaa aagtgagatt t tactaagac    3780
```

```
ctgtttact   ttacctcact  aacaatgggg  ggagaaagga  gtacaaatag  g atctttgac   3840 cagcactgtt  tatggctgct  atggtttcag  agaatgttta  tacattattt  c taccgagaa   3900 ttaaaacttc  agattgttca  acatgagaga  aaggctcagc  aacgtgaaat  a acgcaaatg   3960 gcttcctctt  tcctttttg   gaccatctca  gtctttattt  gtgtaattca  t tttgaggaa   4020 aaaacaactc  catgtattta  ttcaagtgca  ttaaagtcta  caatgaaaaa  a aagcagtga   4080 agcattagat  gctggtaaaa  gctagaggag  acacaatgag  cttagtacct  c caacttcct   4140 ttctttccta  ccatgtaacc  ctgctttggg  aatatggatg  taaagaagta  a cttgtgtct   4200 catgaaaatc  agtacaatca  cacaaggagg  atgaaacgcc  ggaacaaaaa  t gaggcggcg   4260 gaacaaaaat  ggggtgtgta  gaacagggtc  ccacaggttt  ggggacattg  a gatcacttg   4320 tcttgtggtg  gggaggctgc  tgaggggtag  caggtccatc  tccagcagct  g gtccaacag   4380 tcgtatcctg  gtgaatgtct  gttcagctct  tctgtgagaa  tatgattttt  t ccatatgta   4440 tatagtaaaa  tatgttacta  taaattacat  gtactttata  agtattggtt  t gggtgttcc   4500 ttccaagaag  gactagtagtt agtaataaat  gcctataata  acatatttat  t tttatacat   4560 ttatttctaa  tgaaaaaaac  ttttaaatta  tatcgcttt   gtggaagtgc  a tataaaata   4620 gagtatttat  acaatatatg  ttactagaaa  taaagaacaa  cttttggaaa  a aaaaaaaa   4680 aaaaaaaaa   aaaaaaaaa   aactactcta  naanannnnn  nnnnnnnnnn  n nnnnnnnn   4740 nnnnnnnnnn  nnnnnnnnnn  nnnnnnnnnn  nnnnnnnnnn  nnnnnnnnnn  n nnnnnnnn   4800 nnnnnnnnnn  nnnnnncaa   ataaagcant  agcatccaaa  ttttcaccaa  n taaagct    4858

<210> SEQ ID NO 2
<211> LENGTH: 179
<212> TYPE: DNA
<213> ORGANISM: Homo sapiens
<220> FEATURE:
<221> NAME/KEY: misc_feature
<222> LOCATION: (1)...(179)
<223> OTHER INFORMATION: ace (angiotensin-converting enzyme)

<400> SEQUENCE: 2
ggaatgtgaa  atcttgcccc  gggtcaaaat  caccttagt   ccttggcact  t gggggaca    60 gggcctggta  cttcaacctt  gaggtccacc  acatcccggt  tataaatttc  c ttgggtgag   120 gtttcatcaa  ataaactcca  ggcccaatga  tcgacgaggg  tagtcgaagg  g gaaaaagg    179

<210> SEQ ID NO 3
<211> LENGTH: 553
<212> TYPE: DNA
<213> ORGANISM: Homo sapiens
<220> FEATURE:
<221> NAME/KEY: misc_feature
<222> LOCATION: (1)...(553)
<223> OTHER INFORMATION: Hemoglobinase

<400> SEQUENCE: 3
ttttttttgg  tttctgttat  aaatctttat  tttttaagac  ttgaacacct  g cagaattaa   60 atacaaaagc  aatcaaaaat  catcatattt  tctaaaaaac  agttttccat  t tggggcttg   120 cgggccctct  tcaaataaaa  tcattctgaa  gatttaaaga  ggtttcagct  t caaattctc   180 agaataaaga  ctcctttga   gaggggctac  agaagccccc  atgagcttcc  t gctcctcaa   240 aactaacagg  caaaacaaca  aacctcctag  gaaaggcaaa  tatgacccct  c tcaatacag   300 agcttttccc  accctaattt  gtaggttttt  cagaaaagac  tgggggaag   g cagggtaac   360
```

-continued

| | | |
|---|---|---|
| agcgagcaag tcatcttgtg aagaaggtcc tggagcgagc cctggagcgg g ggctcccca | 420 |
| ggagggcccg agcagcggag acttctcact ccacctctcc aatccccaaa c agcacacag | 480 |
| tcggtggggc gctcacactt ggaaaagctt ccaggaggca gctcttcagt a ggaccaagg | 540 |
| cacacgtggc cac | 553 |

<210> SEQ ID NO 4
<211> LENGTH: 1232
<212> TYPE: DNA
<213> ORGANISM: Homo sapiens
<220> FEATURE:
<221> NAME/KEY: misc_feature
<222> LOCATION: (1)...(1232)
<223> OTHER INFORMATION: sercarboxy (serine carbox ypeptidase)

<400> SEQUENCE: 4

| | |
|---|---|
| accccgcgtc cgcaggtgga ctccgggctg gagctgtcct gggggagctt g tttgcggca | 60 |
| gcggctgctg ctgccactgc tgtgctgggg gcccggtcgc caggcaaaaa g ccctcccac | 120 |
| gtttgagggg agtcatgagc cgtttcctga atgtgttaag aagttggctg g ttatggtgt | 180 |
| ccatcatagc catgggaac acgctgcaga gcttccgaga ccacactttt c tctatgaaa | 240 |
| agctctacac tggcaagcca aaccttgtga atggcctcca agctcggacc t ttgggatct | 300 |
| ggacgctgct ctcatcagtg attcgctgcc tctgtgccat tgacattcac a acaagacgc | 360 |
| tctatcacat cacactctgg accttcctcc ttgccctggg gcatttcctc t ctgagttgt | 420 |
| ttgtctatgg aactgcagct cccacgattg gcgtcctggc acccctgatg g tggcaagtt | 480 |
| tctccatcct gggtatgctg gtcgggctcc ggtatctaga agtagaacca g tatccagac | 540 |
| agaagaagag aaactgaggc cagcattatc acctccagga ctttctcgtt t tccaccttg | 600 |
| gccatcttct tccttcgtcg tctctcctct ttaatttctt ttctattcca t catctgccc | 660 |
| ttttattcac ttttagcctc tttttttaat ttttaaaatt taaagatatg c atactgaaa | 720 |
| agtatataac atgtacgtac aatttaaaga ataattttaa agtgaatact a cgtaactcc | 780 |
| atccaagtca agaaattgcc agcttctcgg aagcccactg tgtctccttc c cctacctgc | 840 |
| aacctcttcc aggctcccct ttccagcctt ccccttttc ccttttattt t catgccttg | 900 |
| atttgacttg tgtggtggga acatgtgaac tatgaaactt aaacctgctg c ccacccaga | 960 |
| gcagctgtga ccaagggctg cctcaagggg ttgtccacgc aggttgggct c ctctctgct | 1020 |
| gctggaccca agactctgaa ccttccaagg gacaggcagt tcttctaaga a gggctcccc | 1080 |
| tgtgtgtgag caagaccaca gctctccttc tatctacaga tgcatgaggg t tggaagagt | 1140 |
| ctgggctgtt tttagccctt ctggtcagct gtatttgtgt aacaacttt g taataaata | 1200 |
| gaaaaaccct ctgctctgaa aaaaaaaaaa aa | 1232 |

<210> SEQ ID NO 5
<211> LENGTH: 5357
<212> TYPE: DNA
<213> ORGANISM: Homo sapiens
<220> FEATURE:
<221> NAME/KEY: misc_feature
<222> LOCATION: (1)...(5357)
<223> OTHER INFORMATION: reprolysin (ADAM family of metalloprotease)
<221> NAME/KEY: misc_feature
<222> LOCATION: (1)...(5357)
<223> OTHER INFORMATION: n = A,T,C or G

<400> SEQUENCE: 5

| | |
|---|---|
| tctttagact agtctnncgn ccngccctt tttttttgga atggtagatg c tcatttatg | 60 |

-continued

| | |
|---|---|
| taaaatcata taaaatgtta cacaaactgt tagaataaaa aaataccttt t ttgagggggg | 120 |
| aggaggtccc cagcctgctg ctgggtagtg agaggggggtt agcaccatta g ggcgcaggg | 180 |
| ggcgggagct ccgccacagc ccgtggtggg cactgaggtc tgtcggtcgg t ctgtgcatc | 240 |
| ctggcacagt cagcggcggg caacccgctg atggcctcgg gaggggcgc c gtggctggg | 300 |
| cggagagcac gaagcggcag cactgggtgc ggatggtggg cagctggcag c ggcccagta | 360 |
| ggcgcagcgt ctcgcagaac ccgaaggaca ggcggtcccg ctcacagcgg g gaggctcga | 420 |
| cgggctcaca atcctcggtg ccacgcgcc gggagctctc aggccaggcc t cgtggccac | 480 |
| actggtcact gtcttcctcg ggcagccctg tctgggtgtt gacacacttg a ccaggcgcc | 540 |
| gctggacacc accaccacag ggggctgagc actggcccca gggcccccacc a cccactgcg | 600 |
| tgcaggggtg ggtgttgcag ggccgggtgg tgttgggtct cagcgcctcc t cgcagaggc | 660 |
| ctggctccgg gcaggtcact agacgctgct gctcaccacc gccacaggcc t cggagcact | 720 |
| ccctccagga agatgtgtac cagctgaggc agggctgggc cccgcagggc c ggtgcgcag | 780 |
| gcggcttggc aggcccgggc tgacaatgga agggccgcag tggccggagg t cccgtgtgt | 840 |
| ccacacactg cacgtcccgc actgaggaac ctccgccgca gctgcgggag c acttactcc | 900 |
| agttgcctga gtgccaggtg gcacagggcc gcaggtggca gcggcgggca g gctggggcc | 960 |
| ggccagcggg ggcgcagtcc tcatcccggc cggagctaca gcgcaccggc c tccagaccg | 1020 |
| cacccaggcc acaggtggta gagcactcgc tccagtttcc cgcttgccag c tggcgttcc | 1080 |
| tgacaaccaa cgggtccgcg gggggccccg cttcagccag gctgggagcc a gcggctggg | 1140 |
| tctcagggac tctgtggctg ttggcggggc tgtcccaagc tggtgtggac a gcagcctag | 1200 |
| agctcagggg cacctcaggg ctgagggact caggctgacc cttgggtcct g ggttcaggg | 1260 |
| caggctcagg catgtgcccg aggccagtca gggttgtggg gaggaaggtc c cccacactg | 1320 |
| ccacagtctg caggtcccat gagcctggtc ctggggctgg gaaggaggga g tccccggct | 1380 |
| ccagggaact gtccctgacc ttcatctctg gcagagggc tatgggagga g gaaggagag | 1440 |
| aagccacccc aacagtgggc cacagttcac tgtccacagg ccccaggcca c cctccagag | 1500 |
| ctggctccca ggccactgtg cctcctgtcc acagctccgc cacgtcagga c taggagagg | 1560 |
| agtgggtgct gccaacaggg gacaaagggg gcagcgtgaa gctgggtctc g ggggcaggt | 1620 |
| ggggtgctcc gcggcccttg ggttccttca tcatcccttg aaaaccttca t tggtcctgt | 1680 |
| cccgccatgg aggggggcagc tggctctggc tgtccttgcc aactgggaaa t cattttggc | 1740 |
| tctcagggggt ggcaaggtgt cttgcaggcc atcagtggaa accctgggcc a ggacaggct | 1800 |
| ggggagccca agatctgggg cccctatggg ggtgtcttcc tcaggcagga a attgatcaa | 1860 |
| agggttccca ggggtctgct ctgagggtgg gggtggggag cggccggcct g gctaggcca | 1920 |
| agggctcggg gaccaaggtc ccagtacccc ctcctccttg gctgcaggag g ctctgtggc | 1980 |
| aggcacaggg ctacccgtgg agggcgcagc aggacggctg tgtggtgggg g tgtccggtc | 2040 |
| ccctgtcccc gccaggtcta gatcgggctc ctcagagggc ccgtaggaca g atcctcgtg | 2100 |
| gaaattgatg aaaattgtag tcgtagtaga agtcgtccac aaacacgggc c ccggcaggt | 2160 |
| ccagctctgg agcctcctcc tcaatggcgt tgcccatggt gcctggcttg g gtgatgagg | 2220 |
| cgggtaaagg gcgtggggcc aggtggtgcg ggatgaagtc agcctcgttg a agagctcgt | 2280 |
| ggctggagga gccgctgcct gagccttcag ggcccagtgt gccagggggc c accgacaga | 2340 |
| gtggcagaga gcaggtgact tcgctggctg gctgctgggc ctcgtcacag g ggacaccgg | 2400 |
| tgtcattggt gcagaggaca tttcggcgct gagtgccctc cccacatgtc a ctgagcact | 2460 |

-continued

```
gagaccagtt ccccacagcc caggtggccg gacagggtac atggcggttg c aaggggttt    2520 cagtaggggg ccggggaagg tgttcacagg cgggtggctc cagggcgctc t gctcatcca    2580 gccccacgct gcggatgcag agcacggccc ggcgggagag gcccccaggc c cgcaggagc    2640 tggagcacag ctgccactca cctgcccacc acctggcagg gcagggctgc t cgctgcact    2700 tcctctgttg gtcatcaggc cggcccaggg ggtcacagtc tcctcgtcc a cgggccctg     2760 cctgccgctc caagcagtac acattctgcc tctgcacacc tctgccgcag g tgactgtgc    2820 acttggtcca gggcccataa tgccaggaga acacgggcgg cgggacctcg t cgtggccac    2880 ctgcctccct gtggatggtg tactcgtagt gcaccccagg gttgctctcc t ggaacagca    2940 gctggatcca gacaggctcc ttggtgggac ccggggacgt gaggttctcc c agttgcccc    3000 tgcgtgcgta tgtgaaggtg gtccctgcca cctggtagtc cccgttccac t ggatggtcc    3060 agccaccatt gaggaagtac ttctccgggt cctcactccg cagtgccagg a agttggcag    3120 cctcggcaac ctcttggatg cggatctcgc gtgcgccggc tgggatcagc c ccacatcca    3180 cataccccag gccctcggcc tcctcgaagg tcccgctcac ggtgtggcag g tggagccgt    3240 tgccgtggca cacaccacag cggtcctcca tagcaccgga gtcaatctcg a agtcacagc    3300 ccacgttctt acagatgccg ttgatgcaga ggtcccggct ggctcggacc t ggtagcagg    3360 gggtgccatc gaccacggcg tcccgcagct tctcggcaaa gtactcattc g cgggccggc    3420 agtgcagctc gcaggggttc acgtcattga ccacgggcac ccatgtgtgc a gctggccct    3480 tgtagagcat agcgtcaaag tggctgcact ggacgtggcg gaaggagggg c ggccagcag    3540 ggcaggcctg caggttgcag aggcggaagc gcttgcgctc acccacacag t atctgcctt    3600 tgtatttggg cgtaggctgc gtgcactgcc gctcggcgct ctgtacgccc a tgccacagc    3660 tccgtgagca gatggaccag cgctccagc cagaccagcc accatccacg g cctcgggcc    3720 ggaagcccac gggtacgcac tccccactga cacaccactt attctcccca c accgggtgc    3780 cgtccacggg ctgcatccag cttggagtga caggtggtcc ccacagagca c cagagtgtg    3840 tggcagacat tatccatgtc ctcgcagaag gcagagtagg ccccgtactg g aggcggcac    3900 tggtggctta catcatagag gacgccaggt ggcaccgagg ggaagtcgat a atgtccttg    3960 gcaggagggt cgtccaggca caggccccac ccacggtcaa ggaacctggt g atatactgg    4020 cggctgcagc gggaccaggt gaggggagcg gcgtcgtaca ggagctgtgg a gacatgatg    4080 aaaggtcgtt tcccaacggg ctcacagtca ttgccgcttc cgtcatgctg a atgccaaaa    4140 ctgtgcccga gctcgtgggc tacagtgaag ccagcggca ggcccgtgtc c tcgttgatg     4200 ctgcagctgc ggtgcggctg gcacatgccc gccacatggg acagtcccag g gtctcacag    4260 ggccggttca tggctgcaca caggtccttt ctggtgagca ggatggcagt g tcatggtgc    4320 agggatggg catcccccttt catgttgatg cttttctgcc acttgcagaa g ctcttcagg    4380 gtgttgtctg catggtgcgt gatctttagg tcctcctcct catcttccag c aggaccagg    4440 cgcacaatgg tgatgtggat ggggttccca atgctgggt catgaaacag g ccagccacc    4500 atgttcatga tggtcagcac atagctctca acctgcggct gtccgtggta c tccaccatt    4560 ttggcatcag ctactaccag ggtctccacc cacttctctt tgctgaccga c cgctggtgt    4620 agacgcctca gccgtggccc gccgccactg ctgccgctgc tcccaacgct c ccgtcgaga    4680 ctccagctct gggtacactt gcactccaca ggtgcttgga gcactggaat c accccgctg    4740 tgccagcctc tccggggcct gacgcttgta caccacatgg ggctgggcgt g gccaggccg    4800
```

```
ggccggggca ctgtccaggg gctcaatgaa gtagtcctcg ttggagagct g aacacacc      4860 tttcaggccg tcgcaggcgc tgatggccgc caggccaccc tcgagctcag g gtcctgcac      4920 ctcgccaagc aggtggcagg ccggggtgtg gcccggatg tgcgcgcggc c caggccgcc       4980 gcgccgccgc gtctcgctca caaagccggg cgccagcagg tgcttgattg g cggtcaggt      5040 tgaagcgcag ctcgcgcccg cggtattgta gctcgtagaa ggcgggcgcg t ctcggcgca     5100 cagatacatc ccgcttgcgc agtgcgcggg gccacagctc gtaggacagg a aggagcccc     5160 ccgcgtcgac tcgaaccggg tgcacgatgt ccagtgccgc ccggccctcg g ttgcacgtc     5220 ctggtgcggg tccggggcg ccgggagcca gagcgcagag gagcaggagg a gggggcgca      5280 gcaaaggcgc ggggctgcgg ggactggggc cgccgggcat ggcaggaacc g ggcggccgc     5340 aagcttattc ccttngg                                              5357
```

<210> SEQ ID NO 6
<211> LENGTH: 703
<212> TYPE: DNA
<213> ORGANISM: Homo sapiens
<220> FEATURE:
<221> NAME/KEY: misc_feature
<222> LOCATION: (1)...(703)
<223> OTHER INFORMATION: reprolysin (ADAM family of metalloprotease)
<221> NAME/KEY: misc_feature
<222> LOCATION: (1)...(703)
<223> OTHER INFORMATION: n = A,T,C or G

<400> SEQUENCE: 6

```
gcaggagggg ctgtgtgaca ccctgggtgt ggcagacatc gggaccattt g tgaccccaa      60 caaaagctgc tccgtgatcg aggatgaggg gctccaggcg gcccacaccc t ggcccatga     120 actagggcac gtcctcagca tgccccacga cgactccaag ccctgcacac g gctcttcgg    180 gcccatgggc aagcaccacg tgatggcacc gctgttcgtc cacctgaacc a gacgctgcc    240 ctggtccccc tgcagcgcca tgtatctcac agagcttctg gacggcgggc a cggagactg    300 tctcctggat gcccctgctg cggccctgcc cctcccccaca ggcctcccgg g ccgcatggc   360 cctgtaccag ctggaccagc agtgcaggca gatctttggg ccggatttcc g ccactgccc    420 caacacctct gctcaggacg tctgcgccca gctttggtgc cacactgatg g ggctgagcc    480 cctgtgccac acgaagaatg gcagcctgcc ctgggctgac ggcacgccgt g cgggcctgg    540 gcacctctgc tcagaaggca gctgtctacc tgaggaggaa gtggagaggc c caagcccgt    600 ggtagatgga ggctgggcac cgtggggga ccctggggag aatgttctcc g gacctgtgg     660 aggaggaagt acaagtttcn caaccgtgaa tgcaaggacc ccc                       703
```

<210> SEQ ID NO 7
<211> LENGTH: 3126
<212> TYPE: DNA
<213> ORGANISM: Homo sapiens
<220> FEATURE:
<221> NAME/KEY: misc_feature
<222> LOCATION: (1)...(3126)
<223> OTHER INFORMATION: reprolysin (ADAM family of metalloprotease)

<400> SEQUENCE: 7

```
tcgcccttt ttttttttt tggcataaga tcacacttta gttcagagac a catttgcat      60 aaatacttga aatggatcca ccctgcagg tggcagcctg agaacatgtg g ctctccaaa    120 ccctgcgacg ctgcggccct ttaggtgatg gatttttaaca ctgaagacag t cgtggtcat    180 tcttgaagac agcttggggt ccagctttgg agcctgcttt gacattcacc a ttgactccc   240
```

```
tgccccacgc ctctcttgta ctaattttt  ccctgtgag gtagattatt t atcgggaa    300 accagataga attttttt  tcatttaagt tgctagtcc tttgcaaaca g actgacgct    360 gagtgtcctg tctgagtcaa taagtgcact tttacctttt aacctatgcc c tctacttga  420 acccgagcaa ggtccagtcc actggacagt tgatgatagg gtctgccgcc c catacctc   480 tcctcttccc ccttaggaat ttgtgcagta ctggaggggt tgcggcaatg g gaggcctgg  540 gtgggccgtg ctgccttgat atggccaagg gacccagtca ccacagtgga g acccttgtc  600 tgcacctcag taccgcatgt ccaggagcac aagactggcc cctgccccc  t gaatcacag   660 ggggcacagc tggctttcgc agggcttggc atcctcgggt ttcagagcct t gttgcaggt  720 ggcagaggcc tggccggagg ggtccctgca ctctacagtt cgcctctgcc a gccggcccc  780 gcaggtgcta gagcactcag accagtcccc cagcacccac tgtgcgtgga g cagcggctg  840 gatgatgttg gtggttgctc tctctttgct gctctgcatg ctaaagtcca c gtcattagg  900 aacaaagaag gtgtatttga ctttggggg  gaagacctcg ccagggactg t caggagctg   960 cactgtcaga ggctctggca agggccggaa gctctgcagg cgctccaggg t ggcgatgga 1020 gccgctgtac ttcaggatgg tccccttcac caagatgtcc tgctctatgg c agagatggc 1080 caggttgccg ttgagcaggt actgcccatc agccgtcttc agcgccaggt a gttcccatc 1140 gttctgcaca cccgggtggc tccgctgctt cacgtcaata ttagtggcac c agctgggat 1200 ggtgacaatg tcattgtagc cataattggt ggggtgagg  gacccggaga c cttcctgca  1260 ggagttgcct ttgcccccac acaccccgca tttgtccagc ttccgaggcg a gtccaccac 1320 atggtcacag ccggccttga cacactggca acggacacag atggccagtg t ttctggccc 1380 acacagggtg ccatcaatca ccttggcctc gaacactttg aactcgctcc t ccccgggc  1440 tcggcagaac aacttgcagc ggtcccgggg ggacacccca gcatacttgg g gacccactg 1500 caggagattc ccgtccatgt cagtgtaatt gtaggcatta tacttctcac a ctgctgctc 1560 cctgaagctt ttcccgtcag gggggcattc ctccgtgtgg catgactggt a cttggctct 1620 ccgacccagg cagtatcttc ctccattctg aggctcgggg tccttgcact c acggtgtga 1680 aaactgtact cctcctccac aggtccgaga acattctccc caggtccccc a cggtgccca 1740 gcctccatct accacgggct tgggcctctc cacttcctcc tcaggtagac a gcttgcctt 1800 ctgagcagag gtgcccaggc ccgcacggcg tgccgtcagc ccagggcagg c tgccattct 1860 tcgtgtggca caggggctca gccccatcag tgtggcacca agctgggcg  c agacgtcct  1920 gagcagaggt gttggggcag tggcggaaat ccggcccaaa gagcataatg c aacgctgta 1980 gcacctagac acagggccat aaatacctga aatcggtgcc ccccgtcaag a agctctgtg 2040 agatacatgg cgctgcaggg ggaccagggc agcgtctggt tcaggtggac g aacagcggt 2100 gccatcacgt ggtgcttgcc catgggcccg aagagccgtg tgcagggctt g gagtcgtcg 2160 tggggcatgc tgaggacgtg ccctagttca tgggccaggg tgtgggccgc c tggagcccc 2220 tcatcctcga tcacggagca gcttttgttg gggtcacaaa tggtcccgat g tctgccaca 2280 cccagggtgt cacacagccc ctcctgccca cagaagttct gtctggtgag c aggatggcc 2340 gtgtcgtagt gctctgggtg gcggtcgctg ggctggttga acgccgctg  c cagttgcag  2400 aagttacgca gtgtaagccc cccattgtcg gacacctctg ggccccattt t tcatcttct 2460 acgatcagca cttttaccac catcaggttg atggaattct tgatgctggg g tgcttgtag 2520 attcgggctg ccacagacat taacgtcagg atgtggttct gcaggtcggc c ccgtagaag 2580 gcagccatgg acgcatcggc caccagcagc gtctccacga agcgcgcctc a gacacaaac 2640
```

```
cgcttggtcc tactcgtggc ccccagggc ggtggcggct cgctagcgcc t tctgcctcc      2700 tcttcttggc tctcctcctc gctgtcctcc tggtggtctc ctctctcctg c ctctgaccc      2760 tctcccgtct ccacctccca ctcgggtcct cgcgggaggg ggcgggctcc g gcgggaccc      2820 cagcgctgca ggcggtgcgg ctgacccagg gagcccccg cgccctgcgg c tggatggtg      2880 aactcctcgc cgtccagcag gaaggagccg ctcagcccgc ggcacaggct g accgccgcc      2940 agcgactcgg cggacgcgtg gacggtgccg gagaagaagc agccgcgcag c cccgctcg      3000 ccccggtcg cccggccgga gccccgagg cgctcgatct tgaagtcggg c gccaggaag      3060 ctgtcgtcgg gcgccaggcg cagcacgaag cccttgccga aggcggacag g tggagcgcg      3120 agcttc                                                                  3126
```

<210> SEQ ID NO 8
<211> LENGTH: 482
<212> TYPE: DNA
<213> ORGANISM: Homo sapiens
<220> FEATURE:
<221> NAME/KEY: misc_feature
<222> LOCATION: (1)...(482)
<223> OTHER INFORMATION: reprolysin (ADAM family of metalloprotease)
<221> NAME/KEY: misc_feature
<222> LOCATION: (1)...(482)
<223> OTHER INFORMATION: n = A,T,C or G

<400> SEQUENCE: 8

```
acgcgtccga cttgaaccac accaaacagc gtctcctgga agtcgccaac t acgtggacc      60 agcttctcag gactctggac attcaggtgg cgctgaccgg cctggaggtg t ggaccgagc      120 gggaccgcag ccgcgtcacg caggacgcca acgccacgct ctgggccttc c tgcagtggc      180 gccgggggct gtgggcgcag cggccccacg actccgcgca gctgctcacg t gggtgcctc      240 tgacccggac gcgggtcccg ggtggggcgg cctcacctcc cggccccgcc t ggtcacgcc      300 gcgctccgcc cccaggggcc gcgccttcca gggcgccaca gtgggcctgg c gcccgtcga      360 gggcatgtgc cgcgccgaga gctcgggagg cgtgagcacg gaccacttcg g agctnccca      420 ttcggcgccg cagccaccat ggcccattga gatcggccac agccttcngc t taagccacg      480 ac                                                                      482
```

<210> SEQ ID NO 9
<211> LENGTH: 522
<212> TYPE: DNA
<213> ORGANISM: Homo sapiens
<220> FEATURE:
<221> NAME/KEY: misc_feature
<222> LOCATION: (1)...(522)
<223> OTHER INFORMATION: t1a (t1a (proteasome-a) protease)
<221> NAME/KEY: misc_feature
<222> LOCATION: (1)...(522)
<223> OTHER INFORMATION: n = A,T,C or G

<400> SEQUENCE: 9

```
taactttatt ttctgggttt attcccccct tgttccaagc tcttaagcct c agcttactc      60 cacctccata gcctgcacag tttcctccac tagctccagg gttagtggct t cactgtctg      120 ggtcaggaca gctgtggttc caggcacaaa gtggtagcgg ccagacctct t cacgggctc      180 tgtgggtgag ctcagtgtcc gcagcagctt ggcgccagtc tttgtgatca c acatgcgtc      240 cacattgccc ccggagccca ggtcacccaa gatcccggcg gtgacggctt c caccagcag      300 cccctgagca gcctccagcg tcatgttcgg ctggaaccgg tcttctagca c cgccagggc      360
```

```
cgcgtcctga  ccagagccca  gggctgtgaa  gggcagacgg  ctgtaggagc  c attgggatg      420 cacaccgtag  agctgcgcgg  acgcgtgggt  acgccgnccc  agatcagcga  t gcaaccacg      480 tggccctggt  accttgaaga  gcgctgtgcg  caagatagca  gt                           522

<210> SEQ ID NO 10
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: t1a (t1a (proteasome-a) proteases)
<221> NAME/KEY: misc_feature
<222> LOCATION: (1)...(271)
<223> OTHER INFORMATION: n = A,T,C or G

<400> SEQUENCE: 10
gccngaggaa  tgcgtncttg  gaacacgtcc  ttccgggact  tcgggttcct  c atgcacgca       60 agaccgggac  taccatcgcg  gggcttgtgt  tccgagatgg  agtcatcctg  g gagcggnca      120 cgcgggctca  ctaacngatt  cggttgtggc  ggacaaaagc  tgncagaaga  t ccacttnat     180 cgnccctaaa  nttntacttg  ctgttggngc  tggagtagnt  tgcggacact  g agnatgact     240 acgcggangg  cagcnttnca  agattggnaa  c                                      271

<210> SEQ ID NO 11
<211> LENGTH: 407
<212> TYPE: DNA
<213> ORGANISM: Homo sapiens
<220> FEATURE:
<221> NAME/KEY: misc_feature
<222> LOCATION: (1)...(407)
<223> OTHER INFORMATION: pcnp (procollagen N-prote inase)
<221> NAME/KEY: misc_feature
<222> LOCATION: (1)...(407)
<223> OTHER INFORMATION: n = A,T,C or G

<400> SEQUENCE: 11
tattgtctgg  gcgnggagtg  ggagtacaga  gacgaggacg  gcccgggaga  c gctgcacac       60 catgggcccc  ctccacggca  ccatcaccgt  ngntggtcat  nnnggtggga  g acacccnga     120 tntnnnnnnn  gnacaaattn  ataatnatca  ttgngctcac  tgaatgtgtg  a nctnnacat     180 nntactgtan  nangncnctn  tnncctacga  gtggacnntg  aagangngga  c tgangtgct     240 cnaagctctg  anaacngagg  gtccnancnn  accnngtatg  gcngccntcg  t angctggac     300 cacaagatgg  tacaccgngn  cttttgtncc  gcnctctcga  agcncannnt  n natncntan     360 nagcgngcaa  cccacaggaa  tgctcctaag  ccaagtgtgg  gtcacag                      407

<210> SEQ ID NO 12
<211> LENGTH: 502
<212> TYPE: DNA
<213> ORGANISM: Homo sapiens
<220> FEATURE:
<221> NAME/KEY: misc_feature
<222> LOCATION: (1)...(502)
<223> OTHER INFORMATION: reprolysin (ADAM family of metalloprotease)
<221> NAME/KEY: misc_feature
<222> LOCATION: (1)...(502)
<223> OTHER INFORMATION: n = A,T,C or G

<400> SEQUENCE: 12
cgcgtccggg  actccctctg  gctttacaat  tgcccatgag  ctnggacaca  g cttcggcat       60 ccagcatgat  gggaaagaaa  atgactgtga  gcctgtgggc  agacatccgt  a catcatgtc     120
```

-continued

```
ccgccagctc cagtacgatc ccactccgct gacatggtcc aagtgcagcg a ggagtacat      180 cacccgcttc ttggaccgag gctggggggtt ctgtcttgat gacatacta a aaagaaagg      240 cttgaagtcc aaggtcattg cccccggagt gatctatgat gttcaccacc a gtgccagct     300 acaatatgga cccaatgcta ccttctgcag ggaagtagaa aacgtctgcc a gacacttgt     360 ggtggctccg tgaagggctt ttgtcgctct aagctggacg ctgctgcaga t ggaactcaa     420 tntgtngaag aaaantggtn gattngaggg caagtgctca caggggggga a gaaaccaga    480 gagcantcct ggaggctggg gc                                                502
```

<210> SEQ ID NO 13
<211> LENGTH: 738
<212> TYPE: DNA
<213> ORGANISM: Homo sapiens
<220> FEATURE:
<221> NAME/KEY: misc_feature
<222> LOCATION: (1)...(738)
<223> OTHER INFORMATION: pcnp (procollagen N-prote inase)

<400> SEQUENCE: 13

```
cgcgtccgcc cctaccctga ccccggccgc tatgcctggc actgacccac c cacggcagt      60 gctctgccac ctgtggagag ggcatccagc agcggcaggt ggtgtgcagg a ccaacgcca    120 acagcctcgg gcattgcgag ggggataggc cagacactgt ccaggtctgc a gcctgcctg    180 cctgtggagg aaatcaccag aactccacgg tgagggccga tgtctgggaa c ttgggacgc    240 cagaggggca gtgggtgcca caatctgaac ccctacatcc cattaacaag a tatcatcaa    300 cggagccctg cacggagac aggtctgtct tctgccagat ggaagtgctc g atcgctact    360 gctccattcc cggctaccac cggctctgct gtgtgtcctg catcaagaag g cctcgggcc    420 ccaaccctgg cccagaccct ggcccaacct cactgccccc cttctccact c ctggaagcc    480 ccttaccagg accccaggac cctgcagatg ctgcggagcc tcctggaaag c caacgggat    540 cagaggacca tcagcatggc cgagccacac agctcccagg agctctggat a caagctccc    600 cagggaccca gcatcccttt gccccctgaga caccaatccc tggagcatcc t ggagcatct    660 cccctaccac ccccgggggg ctgccttggg gctggactca gacacctacg c cagtccctg   720 aggacaaagg gcaacctg                                                      738
```

<210> SEQ ID NO 14
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: pcnp (procollagen N-prote inase)
<221> NAME/KEY: misc_feature
<222> LOCATION: (1)...(734)
<223> OTHER INFORMATION: n = A,T,C or G

<400> SEQUENCE: 14

```
ccgctcggga gggcttgggt gggaaggaaa ggcncggtgg acaggagccc a gaaggctca      60 ctgggaaggc cttgaatttc atattcatgg cccgcccct gtgggagagg g agcagaaat    120 ctgtgtgacc ctctccccc accggtcagt ggtgaagaac cagggtcacc g gcagcttca    180 tcctcaaccc caagggcaag ggaaagccac aagccgnacc ttcaccgcca t gggcctgga    240 gtgggaggat gcggtggagg atgccaaggg aaagcttcaa gaccaagcgg c ccctgcctg    300 aagccattgc catcctggct ctcccccaa ctgagggtgg ccccgcagc a gcctggcct    360
```

```
acaagtacgt catccatgag gacctgctgc cccttatcgg gagcaacaat g tgctcctgg    420 aggagatgga cacctatgag tgggcgctca agagctgggc ccctgcagc a aggcctgtg     480 gagggaggga tccagttcac caaatacggc tgncggcgca nacgagacca c cacatggtg   540 cagcgacacc tgtgtgacca caagaagagg cccaagccca tccgccngcg c tgnaccagc   600 acccgtgctc tancctgtgt gggtgacnga ggaatgggt  gcctgcagcc g gagctgtgn   660 gaagctgggg gtgcatacac ngggnataca atgcctgatg cccctctnca a tggaaccca   720 caaggtcatg ccgg                                                      734

<210> SEQ ID NO 15
<211> LENGTH: 733
<212> TYPE: DNA
<213> ORGANISM: Homo sapiens
<220> FEATURE:
<221> NAME/KEY: misc_feature
<222> LOCATION: (1)...(733)
<223> OTHER INFORMATION: matrixin (matrix metallop roteases)
<221> NAME/KEY: misc_feature
<222> LOCATION: (1)...(733)
<223> OTHER INFORMATION: n = A,T,C or G

<400> SEQUENCE: 15
gtgtcgacca cgcgtccgag cggcgcgacc ctggccctcc gggaccctcc g ctgactcca    60 ccgcgcactt cccgggaccc ccacacacat cccagccctc cggccgatnc c tccctactc   120 ggtgccgggt gccccccgcc ctctccaggc ccggatctcc tccccaggt c cccggggcg    180 gccccagcca ggccccccttc gaaccccgcc ggcggcccgg gctggggcgc a ccatgcggc  240 tgcggctccg gcttctggcg ctgctgcttc tgctgctggc accgcccgcg c cgcgcccga   300 agccctcggc gcaggacgtg agcctgggcg tggactggct gactcgctat g gttacctgc   360 cgccacccca ccctgcccag gcccagctgc agagccctga aagttgcgc g atgccatca    420 aagtcatgca gaggttcgcg gggctgccgg agaccggccg catgggctgg a gtgcaatgg   480 gtaccatctc ggctcaccgc aacctctgcc ttccaggttc aagtgattct c tgcctcagc   540 ctttctgagt aagctgggat tacagaacag aagtcttact tctggggccc a agctggagt   600 acaagtggcg caatcttcgg ctcattgcaa tctctggctc cgggtttaaa g ngattnttc   660 ttggcttaag cttctgaggt aggctgggac taacagggca ttccggcaac c atgcccaag   720 ctaaattttt tng                                                       733

<210> SEQ ID NO 16
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: matrixin (matrix metallop roteases)
<221> NAME/KEY: misc_feature
<222> LOCATION: (1)...(621)
<223> OTHER INFORMATION: n = A,T,C or G

<400> SEQUENCE: 16
tttttttttt tttttaact gatcagcctt tgtataatgt ttttaaatc a tttctaaat      60 aaaacagaaa tacagagtgt gtcatttccc tgggatgagg aacaaagat c aggttccaa    120 gagtaacctt aggacgctct gggaagagaa ccgggtcctt tggggtgtct g ggagctgcc   180 cacccatctc ctctgccaga ccggcggtca gatagcctcc ctctacaaca g gctggccct   240 ggggggcccag ggttattggg gttccaggaa cacagcctga tgatgcctcc t tacgatcca  300
```

```
ggatggagag cagccccccc aggagtatgg ggagggtcac tgtggcacgg g cttctccat    360 gacctgggac atgaccagga ggcctgtcct gcctctggaa gccagcgaca g agagggatg    420 cccccgaccc agccagccgg agaaagggat ggggtggtca cgaaggtctg a gctgggtct    480 gggtgtaggc tggaagcag gctggggtgt agactgcgaa gcggccctg c cgggacttc     540 tttccagtcc ccggcgacct cttcgaattc tctgctatct ctggggagcc t cgggnggag    600 ggggtgtaag cggacgcgtg g                                              621
```

```
<210> SEQ ID NO 17
<211> LENGTH: 2629
<212> TYPE: DNA
<213> ORGANISM: Homo sapiens
<220> FEATURE:
<221> NAME/KEY: misc_feature
<222> LOCATION: (1)...(2629)
<223> OTHER INFORMATION: matrixin (matrix metallop roteases)

<400> SEQUENCE: 17
```

```
atcgtgaata tttaaatgtc ctgtcactac tgtcccattg tgcaaaggct g cttgaggct    60 ttaggtgaac tagaggtgac tgtcttggtg atgaggccag catagcggcc c tcccccagg   120 cgacaaggac caaggtgctg ctaaggccac tctagcgccc agacacccca g tagctgagc   180 tctgctccta tggctacaga gctggggcag aagctgaccc catttctgga g gaagatccg    240 agtttgtgac cgtcctccac tcccctctat tgtcactgtc cccagctttg c tccagtctg    300 tcacttgcag cctggagctc agcctcacca gttaggtgag cagagatggc t gcagggcca    360 acactggcag agctggggag tccttcggaa ggggaccagg gcgtctgaag t gctcagtgc    420 ccccactact ctgaggccga ctccagctac tctgaggccg actcaatctc t cggctggaa    480 gcagtgtttt cccagagctt ggcccttgct gacctcgctc actgggccca t cttcccaca    540 ctgctcttag aaggacaccc ctaccggtag cagccccaag ctgaggggc t ccctttttg     600 accttcactg gcccgccctt cactgtctcc agcaggagtt cctagggctt g gcctgcctt    660 gctccacagt acggcggagg cagccctgct tgtcactgag gagccctaga c aaggccaat    720 gggttcatca atgcccactg gctctctgcc aaagccaaaa aggtgtcagg c agtctccag    780 cgtgctggcc gggtctcgga tgccaccct gctcactgag cctgcatggg c cttgccccc     840 gaccctgtgg tctctgggat tggggtcggc ttaccctgta gcacagacag g gactcctgc    900 tgccctggga gctgtctcaa gcaaaatctc ttgtcccaga ggtgcccatg t gggtccgct    960 gtgtcccctg tcatcatcct tgttttttct cattttggcc aagggaaggc t ccctgggac   1020 aggcagggaa caactgcgga gatattagtg attcatagtt ttttttttt t tttatactt    1080 tgcaaagcac tttattagct cacacctgtc cactcacatg aaactcgtgt t aggccctgg    1140 gaggccgacg taactctca ccgtgccctc agatgaagca cagagaggtt g ttacttgcc    1200 cgggccatcc agtgggctgg ctgggtcttg tgtccccatc tgtggacccc t ctagggtct    1260 gagatgagat gagaagtgtc tcctgtatcc acctcttcct ggcctccctt c ccccacttc    1320 ctggtccctg tccactcctc aggttggtgc tctcacttct tgaaagctct a ggcaccccc    1380 gcctcccgcc aggctccccg ttggctcctg gcaggccagc tgagaatgaa c aggagatgg    1440 aggcaggcag cccaggctgc agaggtgagg gatgtgggc caggcccaga g ggctcagcc     1500 tagaggcttc caatctcaga ttctcctgcc tgtggtcatc tgtttgtcca t cacccagg    1560 acagggcaga cagaggggca aagcactggg ggccccagag cctagcttcc c ctcagcctg    1620
```

-continued

```
ggggacatca cagcatttca gtgtcagtca cattttaaac tgatcagcct t tgtataatg   1680 tttttttaaat catttctaaa taaaacagaa atacagagtg tgtcatttcc c tgggatgag   1740 ggaacaaaga tcaggttcca agagtaacct taggacgctc tgggaagaga a ccgggtcct   1800 ttggggtgtc tgggagctgc ccacccatct cctctgccag accggcggtc a gatagcctc   1860 cctctacaac aggctggccc tggggccca gggttattgg ggttccagga a cacagcctg   1920 atgatgcctc cttacgatcc aggatggaga gcagccccc caggagtatg g ggagggtca   1980 ctgtggcacg ggcttctcca tgacctggga catgacctgg gacacatagt c aagagcacg   2040 gttatcagca atacagatat taataaaagg cagacgaagt caggaggtca g caactttgc   2100 gggcttacca ggaggcctgt cctgcctctg gaagccagcg acagagggg a tgcccccga   2160 cccagccagc cggagaaagg gatggggtgg tcacgaaggt ctgagctggg t ctgggtgta   2220 ggctgggaag caggctgggg tgtagactgc gaaggcggcc ctgccgggac t tctttccag   2280 tccccggcga cctcttcgaa ttctctgcta tctctgggga gcctcgggtg g gagggggtg   2340 taagagacgc agggacgtgg ggagaggaga caaggcagga agaaccaca g gggacggcg   2400 gacagacggg cgacatcctg cggaggacgc cgtcagtacc aggaagtgca g gcgatgagg   2460 aagcgcacgt cgtccagcgg cccccacggg ctgggctcgg gctggggctg g ggctggggc   2520 tggggctggg gctggggcgg atgccgggc tgttccgggc cctccggcgc c gcaggctgg   2580 ggctggggct gggctgggt ttgcgcaggc tccgggcgc gcggccgc           2629
```

<210> SEQ ID NO 18
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: reprolysin (ADAM family of metalloproteases)
<221> NAME/KEY: misc_feature
<222> LOCATION: (1)...(388)
<223> OTHER INFORMATION: n = A,T,C or G

<400> SEQUENCE: 18

```
acgcgtccgg ggagcaggaa gcctcatgat ctacaggcac tgtcctactt g tggtcacac    60 aaaaagtacg tggagatgtt tgtcgtggac aacaaccagc ggngncagat g tggggcagt   120 aacgtcaatg agacggtcca gacagtagtg gatgtcattg ctctggccaa c agcttcact   180 agggaataa acacagaggt ggtgctggct ggaatggaga tttggaccga g ggggaccta   240 atagatgtca cagtggactt gcaaatcaca ctcaggaatt tcaatcactg g agacaagag   300 atgctcttca tcgtgcaaaa cacgatgttg cccacatgat cgttgggcat n accctggac   360 aagaatatgg ggccaggcct ttctcagt                                        388
```

<210> SEQ ID NO 19
<211> LENGTH: 678
<212> TYPE: DNA
<213> ORGANISM: Homo sapiens
<220> FEATURE:
<221> NAME/KEY: misc_feature
<222> LOCATION: (1)...(678)
<223> OTHER INFORMATION: reprolysin (ADAM family of metalloproteases)
<221> NAME/KEY: misc_feature
<222> LOCATION: (1)...(678)
<223> OTHER INFORMATION: n = A,T,C or G

<400> SEQUENCE: 19

```
gcccacgcgt ccgcaggaaa gtgccccaca agaggggtgg agttgagatg c cagaccagc    60
```

| | |
|---|---|
| tctcttacag catgcgtttc cggggccgaa gacacgtgat tcacatgaag c tcaagaaga | 120 |
| acatgatgcc cagacattta cctgttttta ctgataatga ccaagggcc a tgcaggaga | 180 |
| actacccttt tgtcccacga gactgttact atgactgcta cctggaaggg g ttcctgggt | 240 |
| ctgcggccac attggatacc tgccgtggag gtcttgcatg gcatgcttgc a ggtggatga | 300 |
| cttgacttac gaaatcaaac ccctggaggc ttctttcaaa tttgagcatg t agtatctct | 360 |
| gcttgtgtca gaagaaaaga ccaaggagan gctagtggat gtattgactt c cacgcgtcc | 420 |
| ggatagatca agaatctgaa aaggtaaaac tggctgaaac tcccagagca g gccacgttt | 480 |
| atttgtggag gcatcataga aaaaacttga aaattcacta cacggttact c gtggattat | 540 |
| tcatgcggaa ccctaatgtg tcacatataa tagagaatgt agtgattatt a acagcatca | 600 |
| tacataccat tttcaaacca gtttatttaa atgtctatat atgtgttttg n gcatatgga | 660 |
| atcaaaagga tgcagtac | 678 |

<210> SEQ ID NO 20
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: trypsin (trypsin-like ser ine proteases)
<221> NAME/KEY: misc_feature
<222> LOCATION: (1)...(493)
<223> OTHER INFORMATION: n = A,T,C or G

<400> SEQUENCE: 20

| | |
|---|---|
| gccccgcgga cgcgtgggcg gacgcgtggg gatgatattg cccttgtgca g cttgctgaa | 60 |
| gaagtttctt ttacagagta cattcgtaag atttgtcttc ctgaagccaa a atgaagctc | 120 |
| tcagaaaatg acaatgttgt agttacaggt tggggaacac tttatatgaa t ggttcattt | 180 |
| ccagtgatac ttcaagaagc cttttgaag attattgaca acaaaatttg c aatgcctca | 240 |
| tatgcatact ctggctttgt gactgattca atgttatgtg ctggatttat g tcaggagaa | 300 |
| gctgatgcat gtcagaatga ttctggtgga ccactagctt accctgattc c agaaatatc | 360 |
| tggcatcttg ttggaatagt aagctggggt gatgggattg tggtcaaaag a atnngccnc | 420 |
| ngcngtctat actccnagtg acttcttatc gcaattggat ttcatncaan a ctgggcttt | 480 |
| tgaaaaaaaa aaa | 493 |

<210> SEQ ID NO 21
<211> LENGTH: 483
<212> TYPE: DNA
<213> ORGANISM: Homo sapiens
<220> FEATURE:
<221> NAME/KEY: misc_feature
<222> LOCATION: (1)...(483)
<223> OTHER INFORMATION: uch2 (Ubiquitin carboxy-t erminal hydrolases
    family 2)

<400> SEQUENCE: 21

| | |
|---|---|
| gccgccccgc gtccgcacaa cttgaccgtg aacctgacca cgttccgact g tggtgttac | 60 |
| gcctgtgaga aggaggtatt cctggagcag cggctggcag cccctctgct g ggctcctct | 120 |
| tccaagttct ctgaacagga ctccccgcca ccctcccacc ctctgaaagc t gttcctatt | 180 |
| gctgtggctg atgaaggaga gtctgagtca gaggacgatg acctgaaacc t cgaggcctc | 240 |
| acgggcatga agaacctcgg gaactcctgc tacatgaacg ctgtcctgca g gccctgtcc | 300 |

```
aattgtcccg ccgctgtact cagttcttct tgagatgtgt ggcggcctgg t gccgcacag    360 ataagaagcc agccctgtgc aagaagctac cagaagcttg gtctcttgag g tctggcata    420 agaaaacccc aagctacgtg gtccccacca gtctgtctca tgggatcaag t tggtcaacc    480 caa                                                                  483

<210> SEQ ID NO 22
<211> LENGTH: 265
<212> TYPE: DNA
<213> ORGANISM: Homo sapiens
<220> FEATURE:
<221> NAME/KEY: misc_feature
<222> LOCATION: (1)...(265)
<223> OTHER INFORMATION: caspase (caspase family of apoptosis regulating
      proteases)

<400> SEQUENCE: 22
ttagagctat ggcccttgga gtaccaaatg attgctgtac cttccgaact a ctatctcta     60 ggtggcaaca ccaaaaatat ttctggaagc atgtgatgag acgagtgatg a atatcgagc    120 ccatcgcgct gactatacag aacacggcgt gtgccgcaga atagcttata g caaagacgc    180 ccttctccac gtgggtcttg gaaacagcat cttcctccac gtgactgaga t gactgtgag    240 aggtcactta caaggatgct cgcga                                          265

<210> SEQ ID NO 23
<211> LENGTH: 385
<212> TYPE: DNA
<213> ORGANISM: Homo sapiens
<220> FEATURE:
<221> NAME/KEY: misc_feature
<222> LOCATION: (1)...(385)
<223> OTHER INFORMATION: pcnp (procollagen N-prote inase)

<400> SEQUENCE: 23
tttgccttct ccaaggaatg tcaacaaaaa taactcaaaa ggaatgtttg a cttcatatt     60 gtctttccca caattagttc actacatgta ggccaggcac tagaagtttg t gctaaaaga    120 atgttcaagt cttactctaa aaactcagtg atatattttc gactacactt t gaccacatc    180 caggggttgg tgtagaagtt cagtgttgga gccatgacat gctggggact c ttaactcct    240 tcttctttac atttgttgtt gtcatcatga ggcatgttaa acacatggcc c agctcatgg    300 gcgatcgtaa aagctgtact caatccacta tcttcactaa tagaacagct t ctataggga    360 tcacaaatgg ttcccagttc agcca                                          385

<210> SEQ ID NO 24
<211> LENGTH: 349
<212> TYPE: DNA
<213> ORGANISM: Homo sapiens
<220> FEATURE:
<221> NAME/KEY: misc_feature
<222> LOCATION: (1)...(349)
<223> OTHER INFORMATION: reprolysin (ADAM family of metalloproteases)

<400> SEQUENCE: 24
tttttctctc tctaccccgt atttacactg acgcgatttg actccatgct g aaagcggca     60 ttgctcatct gcatcgtagg cttggccagg tgccactgtc gggtacacaa a gtcctgtct    120 gggggggccgg ttgttcaggc agagccgcag gccctgagtc tagaaagctg g tgatgtagt    180 cacggctgca ggatgaccac acgaatgggt tggtcttcat ggtaatgtgg g cagccatga    240 gcttggctgg gtccttacca cgggccccac agctgtttcc cacgccgtca t ggttcatgc    300
```

```
cgaatgtgtg cccgatctcg tgggcaatgg tgaacgctgt ggccaggcc          349
```

<210> SEQ ID NO 25
<211> LENGTH: 323
<212> TYPE: DNA
<213> ORGANISM: Homo sapiens
<220> FEATURE:
<221> NAME/KEY: misc_feature
<222> LOCATION: (1)...(323)
<223> OTHER INFORMATION: matrixin (matrix metallop roteases)
<221> NAME/KEY: misc_feature
<222> LOCATION: (1)...(323)
<223> OTHER INFORMATION: n = A,T,C or G

<400> SEQUENCE: 25

```
aaatgagggt tggcatgca gctcgtcatc ttaagagtta ctatcttctt g ccctggtgt    60 ttcgccgttc cagtgccccc tgctgcagac cataaaggat gggactttgt t gagggctat   120 ttccatcaat ttttcctgac cgagaaggag tcgccactcc ttacccagga g acacaaaca  180 cagctcctgc aacaattcca tcggaatggg acagacctac ttgacatgca g ttgcatgct  240 tctgctacan cagcccccact gtggggtgcc tgatgggtcc gacaactnca t ctcgccagg 300 aagatgcaag tggattaagc aca                                            323
```

<210> SEQ ID NO 26
<211> LENGTH: 118
<212> TYPE: DNA
<213> ORGANISM: Homo sapiens
<220> FEATURE:
<221> NAME/KEY: misc_feature
<222> LOCATION: (1)...(118)
<223> OTHER INFORMATION: m17 (peptidase family m17)
<221> NAME/KEY: misc_feature
<222> LOCATION: (1)...(118)
<223> OTHER INFORMATION: n = A,T,C or G

<400> SEQUENCE: 26

```
tacgattgaa atacgggagc gtgtntggag gatgcnntct tgcgaagatt a tanaagata   60 ggttgtagat tggnagcttg cngatgttaa gaanattgga aaatagagat c ngnagga    118
```

<210> SEQ ID NO 27
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: m17 (peptidase family m17)
<221> NAME/KEY: misc_feature
<222> LOCATION: (1)...(658)
<223> OTHER INFORMATION: n = A,T,C or G

<400> SEQUENCE: 27

```
nnnnnnnnnn nnnnnnnnnn nnnccacaac aggtggcttt tttggttttg g ccaggggca   60 aagaattttc aagttggcta atgtccctac catcaaaaat ttgagtacca a tttggtttc  120 taaaggaaaa ccatatcctc ggaaagggga ttgggaggtt caaaaaattt a aatctttta  180 tagagtttct aaaaaaccct tacaaggaaa aatttaacct tcccctttat a aattttggg  240 gggaaggaa aaaaaaacca gggcttccaa tttcattggg gttctccttt t taaaaaccc   300 acccttggcc cccgtaaaaa aattttaacc cttttttaa aaacccttta a ggtccaccg   360 gcccatttaa aaacagaggg aaaactttt ggggtttcgg acctaaccttt g gcctggcct  420 gaaccaaaga aaaactaat ggaaagccct gggggcccctc ccagccttgc c ttcccgaag  480
```

```
ataggaact taatctttgt gggccatcac gctggctatg ctaaatgggc c cactaagga      540 ggagaccaaa tccttcagaa tggctgcagc ggacatgctc ctgcgatctt g atttccaaa      600 tgtggtacat aagcaagctg gaatcaaaca cctggcttgg atagtgtcgg a agagagg       658
```

<210> SEQ ID NO 28
<211> LENGTH: 561
<212> TYPE: DNA
<213> ORGANISM: Homo sapiens
<220> FEATURE:
<221> NAME/KEY: misc_feature
<222> LOCATION: (1)...(561)
<223> OTHER INFORMATION: caspase (caspase family of apoptosis regulating proteases)
<221> NAME/KEY: misc_feature
<222> LOCATION: (1)...(561)
<223> OTHER INFORMATION: n = A,T,C or G

<400> SEQUENCE: 28

```
tttaaaaag atacagtctt tactttatt gaaataccaa atattgacta t gcaagctat       60 actggtaaat gtgctctttg atgttgacag aggagggctg ggctgcctgt g gtttccttt      120 cagattgtct gtgagtctaa tttctcatgg tcgtgtgaca aggaccccat c tttagctga      180 aattttcaat tgccaggaaa gaggtagaaa tctcttgtca aggttgctcg t tctatggtg     240 ggcatctggg ctttagctcg tggaacttca aatgatttct gtaccttccg a aatatttcc     300 attaggtggc agcagcaaga atatttctgg aagcatgtga tgagttccgt a atgaagatg    360 gagccccttg tgcggtctct ccaggacacg ttatgtggtg ttgaagaaca g aaagcaatg     420 aagtccttct ccccggggag tcttgcaaac agaatctgcc tccaaggttc t cagaggact    480 tgtgaagaga tgacngccaa aggatgctgg agagtcttgg acccagagtt c cccanggtt    540 ttcaacctct gcangccccg g                                                561
```

<210> SEQ ID NO 29
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: caspase (caspase family of apoptosis regulating proteases)

<400> SEQUENCE: 29

```
tgccaggaaa gagggggaaa tatcttggga tggacagtca ctttatgggg g gcatttaag    60 ctttggccct tggagtttca aaagattgct gggccttccg aaatacttct t ctacgtggc    120 atcaccaata attttctgg aagcatgtga tgagttgtgt gatgaaaata g agcccattg   180 ggctggctct tcaggacacg ttgagtggtg ttttaaacca taaagctatg a attccttct     240 ttaagtgggt cttgtgaaca aaatcttttt ctcagttctt acttgtaatt g aaaaagcct    300 tttc                                                                  304
```

<210> SEQ ID NO 30
<211> LENGTH: 250
<212> TYPE: DNA
<213> ORGANISM: Homo sapiens
<220> FEATURE:
<221> NAME/KEY: misc_feature
<222> LOCATION: (1)...(250)
<223> OTHER INFORMATION: renaldipep (renal dipeptidase)
<221> NAME/KEY: misc_feature
<222> LOCATION: (1)...(250)

```
<223> OTHER INFORMATION: n = A,T,C or G

<400> SEQUENCE: 30
tgctttccct tctcacctgt tccacttgtc tgaagacccg cactatgtat g catgatgga        60 cacattgaac ctcttcctcg ctccagctac gactcatcaa cttctctatc a tgactgggt      120 atgtggacac atcctacatc cactgaggta accggcctcg tctcgtctat t ntccactaa      180 tgctgatgaa ctcagatcca atgactgctg tgttgtgttc aaagatatct g ccacagtgg      240 acacgttggc                                                              250

<210> SEQ ID NO 31
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: prolyloligo (prolyl oligo peptidase)
<221> NAME/KEY: misc_feature
<222> LOCATION: (1)...(612)
<223> OTHER INFORMATION: n = A,T,C or G

<400> SEQUENCE: 31
tccnttgccg gngaccaatg angtgatcca aggtnttctn gngggtngtn a aaggtnnan       60 ggtcanatat tgtcctcccg attcagnacc tctnntgttg gncttctccn g aggttggtt     120 ctgnaantca tttggtttcc cagccctcac taaaaacctn agtantntnc t ggtntgtga     180 aaantggaaa tcctaatcca ggaaaccatn taagagaagn aacnnattgg g tncagaggg     240 gaactttcct gntggaatgg ccacagatcc taagtaatag ccctgtccat n ctggnnagg     300 gtgacccatn taacgtcccg ngtttcctgt ttcatagaag atccacagag t gactggggc     360 cccagaaata gaaccctgan gatatctgac ctctgaatta ntgccatcag g gagaggtat     420 cctccatagg acagccgngg attgccacac gatcttangt caatgaaatc a tttcgagaa     480 gttagatatt gggagtccnc ccacctgatc cgacaattct tnnggtttnc c ccggatnag     540 cacncnnnnn nnnnnnnnnn ncgnntnnnn nncnnnnnnn nnnnccnnn n ncnnncccn       600 ngnncgnntn tt                                                          612

<210> SEQ ID NO 32
<211> LENGTH: 239
<212> TYPE: DNA
<213> ORGANISM: Homo sapiens
<220> FEATURE:
<221> NAME/KEY: misc_feature
<222> LOCATION: (1)...(239)
<223> OTHER INFORMATION: prolyloligo (prolyl oligo peptidase)

<400> SEQUENCE: 32
ctgagctgag aggaggctgg cttccaacaa agaaatttac agttggatgc a aagctgctg       60 actttggata tggaacccga aaagtctttg ggaacaggag agactcaaca c agcagaagg     120 agaattcaat aagggggact actgcgtagt aaaaacgggc aatagcataa t aagagacag     180 atggagacca ccacaaagca gaggagggggc tgaagagctt ccttcaaaac c cagccagt     239

<210> SEQ ID NO 33
<211> LENGTH: 466
<212> TYPE: DNA
<213> ORGANISM: Homo sapiens
<220> FEATURE:
<221> NAME/KEY: misc_feature
<222> LOCATION: (1)...(466)
```

```
<223> OTHER INFORMATION: aspartyl (aspartyl protea se)

<400> SEQUENCE: 33
ccaggcccac ccggacgctg tttttaatgt accctgggtg taagagggcc a catatgtcc      60
ccaataagac gttcccgagg aaccacaagg gccctgcacg cggaggaaca t ccagggcct    120
ggaaaccgca caagtgaagg cgcccaccat ttctagtctt ctgtatgacg t aatcatgga   180
ccgagaggtt aaaccaaacc ccctaacaa ggaatgagat tggggagggc t ttgtgattt    240
ccgagcacag gatgatgaac taccgaccca gcaaggggat tcccaaagag g atgaatgca   300
gggcccaaat gctctcagtg gctacgtgaa tgagggacct gcccgtatcc a ggatggtag   360
cgcagcccTT gacacaaaga ggcagacatg ggcccacctt cacacgctca a tgtggatct   420
gccagacggc agggaccgtg actggaccct aggtcaggga tggtat                  466
```

NUCLEIC ACID MOLECULES ENCODING HUMAN PROTEASE HOMOLOGS

FIELD OF THE INVENTION

The invention relates to newly identified polynucleotides having homology to various protease families. The invention also relates to protease polypeptides. The invention further relates to methods using the protease polypeptides and polynucleotides as a target for diagnosis and treatment in protease-mediated and related disorders. The invention further relates to drug-screening methods using the protease polypeptides and polynucleotides to identify agonists and antagonists for diagnosis and treatment. The invention further encompasses agonists and antagonists based on the protease polypeptides and polynucleotides. The invention further relates to procedures for producing the protease polypeptides and polynucleotides.

BACKGROUND OF THE INVENTION

Proteases are a major target for drug action and development. Accordingly, it is valuable to the field of pharmaceutical development to identify and characterize previously unknown protease nucleic acids and polypeptides. The present invention advances the state of the art by providing previously unidentified human protease sequences.

SUMMARY OF THE INVENTION

It is an object of the invention to identify novel proteases.

It is a further object of the invention to provide novel protease polypeptides that are useful as reagents or targets in protease assays applicable to treatment and diagnosis of protease-mediated disorders.

It is a further object of the invention to provide polynucleotides corresponding to the novel protease polypeptides that are useful as targets and reagents in protease assays applicable to treatment and diagnosis of protease-mediated disorders and useful for producing novel protease polypeptides by recombinant methods.

A specific object of the invention is to identify compounds that act as agonists and antagonists and modulate the expression of the novel proteases.

A further specific object of the invention is to provide compounds that modulate expression of the proteases for treatment and diagnosis of protease- related disorders.

The present invention is based on the identification of novel nucleic acid molecules that are homologous to protease sequences.

Thus, in one aspect, the invention provides an isolated nucleic acid molecule that comprises a nucleotide sequence selected from the group consisting of SEQ ID NOS: 1–33 and the complements of SEQ ID NOS: 1–33.

In another aspect, the invention provides isolated proteins and polypeptides encoded by nucleic acid molecules of the invention.

In another embodiment, the invention provides an isolated nucleic acid molecule that comprises a nucleotide sequence that is at least about 60% identical, preferably at least about 80% identical, preferably at least about 85% identical, more preferably at least about 90% identical, and even more preferably at least about 95% identical, and most preferably about 98% or more identical to a nucleotide sequence selected from the group consisting of SEQ ID NOS: 1–33 and the complements of SEQ ID NOS: 1–33.

The invention also provides isolated variant polypeptides.

The invention also provides an isolated fragment or portion of any of SEQ ID NOS: 1–33 and the complement of SEQ ID NOS: 1–33. In preferred embodiments, the fragment is useful as a probe or primer, and/or is at least 15, more preferably at least 18, even more preferably 20–25, 30, 50, 100, 200 or more nucleotides in length.

The invention also provides isolated fragments of the polypeptides.

In another embodiment, the invention provides an isolated nucleic acid molecule that hybridizes under high stringency conditions to a nucleotide sequence selected from the group consisting of SEQ ID NOS: 1–33 and the complements of SEQ ID NOS: 1–33.

The invention further provides nucleic acid constructs comprising the nucleic acid molecules described above. In a preferred embodiment, the nucleic acid molecules of the invention are operatively linked to a regulatory sequence.

The invention also provides vectors and host cells for expressing the protease nucleic acid molecules and polypeptides and particularly recombinant vectors and host cells.

The invention also provides methods of making the vectors and host cells and methods for using them to produce the protease nucleic acid molecules and polypeptides.

The invention also provides antibodies or antigen-binding fragments thereof that selectively bind the protease polypeptides and fragments.

The invention also provides methods of screening for compounds that modulate expression or activity of the protease polypeptides or nucleic acid (RNA or DNA).

The invention also provides a process for modulating protease polypeptide or nucleic acid expression or activity, especially using the screened compounds. Modulation may be used to treat conditions related to aberrant activity or expression of the protease polypeptides or nucleic acids.

The invention also provides assays for determining the presence or absence of and level of the protease polypeptides or nucleic acid molecules in a biological sample, including for disease diagnosis.

The invention also provides assays for determining the presence of a mutation in the protease polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

The following text describes classes of proteins with which the sequences described herein have been compared with respect to homology.

Eukaryotic and Viral Aspartyl Active Sites

Aspartyl proteases, also known as acid proteases, (EC 3.4.23.-), are a widely distributed family of proteolytic enzymes (Foltman (1981) *Essays Biochem* 17:52–84; Davis (1990) *Annu. Rev. Biophys. Chem.* 19: 189–215; Rao et al. (1991) *Biochemistry* 30: 4663–4671) that exist in vertebrates, fungi, plants, retroviruses and some plant viruses. Aspartate proteases of eukaryotes are monomeric enzymes which consist of two domains. Each domain contains an active site centered on a catalytic aspartyl residue. The two domains most probably evolved from the duplication of an ancestral gene encoding a primordial domain. Currently known eukaryotic aspartyl proteases include, but are not limited to:

Vertebrate gastric pepsins A and C (also known as gastricsin).

Vertebrate chymosin (rennin), involved in digestion and used for making cheese.

Vertebrate lysosomal cathepsins D (EC 3.4.23.5) and E (EC 3.4.23.34).

Mammalian renin (EC 3.4.23.15) whose function is to generate angiotensin I from angiotensinogen in the plasma.

Fungal proteases such as aspergillopepsin A (EC 3.4.23.18), candidapepsin (EC 3.4.23.24), mucoropepsin (EC 3.4.23.23) (mucor rennin), endothiapepsin (EC 3.4.23.22), polyporopepsin (EC 3.4.23.29), and rhizopuspepsin (EC 3.4.23.21).

Yeast saccharopepsin (EC 3.4.23.25) (proteinase A) (gene PEP4). PEP4 is implicated in posttranslational regulation of vacuolar hydrolases.

Yeast barrierpepsin (EC 3.4.23.35) (gene BAR1), a protease that cleaves alpha-factor and thus acts as an antagonist of the mating pheromone.

Fission yeast sxa1 which is involved in degrading or processing the mating pheromones.

Most retroviruses and some plant viruses, such as badnaviruses, encode an aspartyl protease which is an homodimer of a chain of about 95 to 125 amino acids. In most retroviruses, the protease is encoded as a segment of a polyprotein which is cleaved during the maturation process of the virus. It is generally part of the pol polyprotein and, more rarely, of the gag polyprotein.

Caspase Family Active Sites

Interleukin-1 beta converting enzyme (EC 3.4.22.36) (ICE) (Thornberry et al. (1995) *Protein Sci.* 4:3–12; Kumar (1995) *Trends Biochem. Sci.* 20:198–202) is responsible for the cleavage of the IL-1 beta precursor at an Asp-Ala bond to generate the mature biologically active cytokine, ICE, a thiol protease composed of two subunits of 10 (p10) and 20 Kd (p20), both derived by the autocleavage of a 45 Kd precursor (p45). Two residues are implicated in the catalytic mechanism: a cysteine and an histidine. ICE belongs to a family of peptidases (Nicholson et al. (1997) *Trends Biochem Sci.* 22:299–306) which is implicated in programmed cell death (apoptosis) and which has been termed 'caspase' for cysteine aspase. ICE is known as Caspase-1 and the other members of this family (Alnemri et al. (1996) *Cell* 87:171–171) include, but are not limited to:

Caspase-2 (ICH-1, NEDD-2).

Caspase-3 (also known as apopain, CPP32, Yama), a protease which, at the onset of apoptosis, proteolytically cleaves poly(ADP-ribose) polymerase (see) at an Asp-Gly bond.

Caspase-4 (ICH-2, TX ICErel-II).

Caspase-5 (ICH-3, TY, ICErel-III).

Caspase-6 (MCH-2).

Caspase-7 (MCH-3, ICE-LAP3, CMH-1, SCA-2, LICE2).

Caspase-8 (MCH-5, MACH, FLICE).

Caspase-9 (MCH-6, ICE-LAP6).

Caspase-10 (MCH-4, FLICE2).

Caspase-11.

Caspase-12.

*Caenorhabditis elegans* ced-3 is involved in the initiation of apoptosis.

Drosophila Ice.

Eukaryotic Thiol (Cysteine) Proteases Active Sites Eukaryotic thiol proteases (EC 3.4.22.-) (Dufour (1988) *Biochimie* 70:1335–1342) are a family of proteolytic enzymes which contain an active site cysteine. Catalysis proceeds through a thioester intermediate and is facilitated by a nearby histidine side chain; an asparagine completes the essential catalytic triad. Proteases that belong to this family include, but are not limited to:

Vertebrate lysosomal cathepsins B (EC 3.4.22. 1), H (EC 3.4.22.16), L (EC 3.4.22.15), and S (EC 3.4.22.27) (Kirschke et al. (1995) *Protein Prof.* 2:1587–1643).

Vertebrate lysosomal dipeptidyl peptidase I (EC 3.4.14.1) (also known as cathepsin C) (Kirschke et al. (1995) *Protein Prof.* 2:1587–1643).

Vertebrate calpains (EC 3.4.22.17). Calpains are intracellular calcium- activated thiol proteases that contain both N-terminal catalytic and C-terminal calcium-binding domains.

Mammalian cathepsin K, which seems involved in osteoclastic bone resorption (Shi et al. (1995) *FEBS Lett.* 357:129–134).

Human cathepsin O (Velasco et al. (1994) *J. Biol. Chem.* 269:27136–27142).

Bleomycin hydrolase, an enzyme that catalyzes the inactivation of the antitumor drug BLM (a glycopeptide).

Plant enzymes: barley aleurain (EC 3.4.22.16), EP-B1/B4; kidney bean EP-C1, rice bean SH-EP; kiwi fruit actinidin (EC 3.4.22.14); papaya latex papain (EC 3.4.22.2), chymopapain (EC 3.4.22.6), caricain (EC 3.4.22.30), and proteinase IV (EC 3.4.22.25); pea turgor-responsive protein 15A; pineapple stem bromelain (EC 3.4.22.32); rape COT44; rice oryzain alpha, beta, and gamma; tomato low-temperature induced, *Arabidopsis thaliana* A494, RD19A and RD21A.

House-dust mites allergens DerP1 and EurM1.

Cathepsin B-like proteinases from the worms *Caenorhabditis elegans* (genes gcp-1, cpr-3, cpr-4, cpr-5 and cpr-6), *Schistosoma mansoni* (antigen SM31) and Japonica (antigen SJ31), *Haemonchus contortus* (genes AC-1 and AC-2), and *Ostertagia ostertagi* (CP-1 and CP-3).

Slime mold cysteine proteinases CP1 and CP2.

Cruzipain from *Trypanosoma cruzi* and *brucei*.

Throphozoite cysteine proteinase (TCP) from various Plasmodium species.

Proteases from *Leishmania mexicana, Theileria annulata* and *Theileria parva*.

Baculoviruses cathepsin-like enzyme (v-cath).

Drosophila small optic lobes protein (gene sol), a neuronal protein that contains a calpain-like domain.

Yeast thiol protease BLH1/YCP1/LAP3.

*Caenorhabditis elegans* hypothetical protein C06G4.2, a calpain-like protein.

Two bacterial peptidases are also part of this family:

Aminopeptidase C from *Lactococcus lactis* (gene pepC) (Chapot-Chartier et al. (1993) *Appl. Environ. Microbiol* 59:330–333).

Thiol protease tpr from *Porphyromonas gingivalis*.

Three other proteins are structurally related to this family.

Soybean oil body protein P34. This protein has its active site cysteine replaced by a glycine.

Rat testin, a Sertoli cell secretory protein highly similar to cathepsin L but with the active site cysteine is replaced by a serine. Rat testin should not be confused with mouse testin which is a LIM-domain protein.

*Plasmodium falciparum* serine-repeat protein (SERA), the major blood stage antigen. This protein of 111 Kd possesses a C-terminal thiol-protease-like domain Higgins et al. (1989) *Nature* 340:604–604), but the active site cysteine is replaced by a serine.

Insulinase family, zinc-binding region signature

A number of proteases dependent on divalent cations for their activity have been shown (Rawlings et al. (1991) *Biochem. J.* 275:389–391; Braun et al. (1995) *Trends Biochem. Sci.* 20:171–175) to belong to one family, on the basis of sequence similarity.

These enzymes include but are not limited to:

Insulinase (EC 3.4.24.56) (also known as insulysin or insulin-degrading enzyme or IDE), a cytoplasmic enzyme which seems to be involved in the cellular processing of insulin, glucagon and other small polypeptides.

*Escherichia coli* protease III (EC 3.4.24.55) (pitrilysin) (gene ptr), a periplasmic enzyme that degrades small peptides.

Mitochondrial processing peptidase (EC 3.4.24.64) (MPP). This enzyme removes the transit peptide from the precursor form of proteins imported from the cytoplasm across the mitochondrial inner membrane. It is composed of two nonidentical homologous subunits termed alpha and beta. The beta subunit seems to be catalytically active while the alpha subunit has probably lost its activity.

Nardilysin (EC 3.4.24.61) (N-arginine dibasic convertase or NRD convertase) this mammalian enzyme cleaves peptide substrates on the N-terminus of Arg residues in dibasic stretches.

*Klebsiella pneumoniae* protein pqqF. This protein is required for the biosynthesis of the coenzyme pyrroloquinoline-quinone (PQQ). It is thought to be a protease that cleaves peptide bonds in a small peptide (gene pqqA) thus providing the glutamate and tyrosine residues necessary for the synthesis of PQQ.

Yeast protein AXL1, which is involved in axial budding (Becker et al. (1992) *Proc. Natl. Acad Sci. U.S.A.* 89:3835–3839).

*Eimeria bovis* sporozoite developmental protein.

*Escherichia coli* hypothetical protein yddC and HI1368, the corresponding *Haemophilus influenzae* protein.

*Bacillus subtilis* hypothetical protein ymxG.

*Caenorhabditis elegans* hypothetical proteins C28F5.4 and F56D2.1.

It should be noted that in addition to the above enzymes, this family also includes the core proteins I and II of the mitochondrial bc1 complex (also called cytochrome c reductase or complex III):

In mammals and yeast, core proteins I and II lack enzymatic activity.

In *Neurospora crassa* and in potato core protein I is equivalent to the beta subunit of MPP.

In *Euglena gracilis*, core protein I seems to be active, while subunit II is inactive.

These proteins do not share many regions of sequence similarity; the most noticeable is in the N-terminal section. This region includes a conserved histidine followed, two residues later by a glutamate and another histidine. In pitrilysin, it has been shown (Fujita et al. (1994) *Nature* 372:567–570) that this H-x-x-E-H motif is involved in enzyme activity; the two histidines bind zinc and the glutamate is necessary for catalytic activity. Non active members of this family have lost from one to three of these active site residues.

Cytosol Aminopeptidase Signature

Cytosol aminopeptidase is a eukaryotic cytosolic zinc-dependent exopeptidase that catalyzes the removal of unsubstituted amino-acid residues from the N-terminus of proteins. This enzyme is often known as leucine aminopeptidase (EC 3.4.11.1) (LAP) but has been shown (Matsushima et al. (1991) *Biochem. Biophys. Res. Commun.* 178:1459–1464) to be identical with prolyl aminopeptidase (EC 3.4.11.5). Cytosol aminopeptidase is a hexamer of identical chains, each of which binds two zinc ions.

Cytosol aminopeptidase is highly similar to *Escherichia coli* pepA, a manganese dependent aminopeptidase. Residues involved in zinc ion-binding (Burley et al. (1992) *J. Mol. Biol.* 224:113–140) in the mammalian enzyme are absolutely conserved in pepA where they presumably bind manganese.

A cytosol aminopeptidase from *Rickettsia prowazekii* (Wood et al. (1993) *J. Bacteriol.* 175:159–165) and one from *Arabidopsis thaliana* also belong to this family.

Zinc carboxypeptidases, zinc-binding regions signatures

There are a number of different types of zinc-dependent carboxypeptidases (EC3.4.17.-) (Tan et al. (1989) *J. Biol. Chem.* 264:13165–13170; Reynolds et al. (1989) *J. Biol. Chem.* 264:20094–20099). All these enzymes seem to be structurally and functionally related. The enzymes that belong to this family include, but are not limited to those listed below.

Carboxypeptidase A1 (EC 3.4.17.1), a pancreatic digestive enzyme that can remove all C-terminal amino acids with the exception of Arg, Lys and Pro.

Carboxypeptidase A2 (EC 3.4.17.15), a pancreatic digestive enzyme with a specificity similar to that of carboxypeptidase A1, but with a preference for bulkier C-terminal residues.

Carboxypeptidase B (EC 3.4.17.2), also a pancreatic digestive enzyme, but that preferentially removes C-terminal Arg and Lys.

Carboxypeptidase N (EC 3.4.17.3) (also known as arginine carboxypeptidase), a plasma enzyme which protects the body from potent vasoactive and inflammatory peptides containing C-terminal Arg or Lys (such as kinins or anaphylatoxins) which are released into the circulation.

Carboxypeptidase H (EC 3.4.17.10) (also known as enkephalin convertase or carboxypeptidase E), an enzyme located in secretory granules of pancreatic islets, adrenal gland, pituitary and brain. This enzyme removes residual C-terminal Arg or Lys remaining after initial endoprotease cleavage during prohormone processing.

Carboxypeptidase M (EC 3.4.17.12), a membrane bound Arg and Lys specific enzyme. It is ideally situated to act on peptide hormones at local tissue sites where it could control their activity before or after interaction with specific plasma membrane receptors.

Mast cell carboxypeptidase (EC 3.4.17.1), an enzyme with a specificity to carboxypeptidase A, but found in the secretory granules of mast cells.

Streptomyces griseus carboxypeptidase (Cpase SG) (EC 3.4.17.-) (Narahashi, Y. (1990) *J. Biochem.* 107:879–886), which combines the specificities of mammalian carboxypeptidases A and B.

*Thermoactinomyces vulgaris* carboxypeptidase T (EC 3.4.17.18) (CPT) (Teplyakov et al. (1992) *Eur. J. Biochem.* 208:281–288), which also combines the specificities of carboxypeptidases A and B.

AEBP1 (He et al. (1995) *Nature* 378:92–96), a transcriptional repressor active in preadipocytes. AEBP1 seems to regulate transcription by cleavage of other transcriptional proteins.

Yeast hypothetical protein YHR132c.

All of these enzymes bind an atom of zinc. Three conserved residues are implicated in the binding of the zinc atom: two histidines and a glutamic acid.

Neutral Zinc Metallopeptidases, Zinc-Binding Region Signature

The majority of zinc-dependent metallopeptidases (with the notable exception of the carboxypeptidases) share a common pattern of primary structure (Jongeneel et al. (1989) *FEBS Lett.* 242:211–214; Murphy et al. (1991) *FEBS Lett.* 289:4–7) in the part of their sequence involved in the binding of zinc, and can be grouped together as a superfamily on the basis of this sequence similarity. They can be classified into a number of distinct families (Rawlings et al. (1995) *Meth. Enzymol.* 248:183–228) including, but not limited to those listed below, along with some proteases that belong to these families:

Family M1

Bacterial aminopeptidase N (EC 3.4.11.2) (gene pepN).

Mammalian aminopeptidase N (EC 3.4.11.2).

Mammalian glutamyl aminopeptidase (EC 3.4.11.7) (aminopeptidase A). It may play a role in regulating growth and differentiation of early B-lineage cells.

Yeast aminopeptidase yscII (gene APE2).

Yeast alanine/arginine aminopeptidase (gene AAP1).

Yeast hypothetical protein YIL137c.

Leukotriene A-4 hydrolase (EC 3.3.2.6). This enzyme is responsible or the hydrolysis of an epoxide moiety of LTA-4 to form LTB-4; it has been shown (Medina et al. (1991) *Proc. Natl. Acad Sci. U.S.A*. 88:7620–7624) that it binds zinc and is capable of peptidase activity.

Family M2

Angiotensin-converting enzyme (EC 3.4.15.1) (dipeptidyl carboxypeptidase I) (ACE) the enzyme responsible for hydrolyzing angiotensin I to angiotensin II. There are two forms of ACE: a testis-specific isozyme and a somatic isozyme which has two active centers (Ehlers et al. (1991) *Biochemistry* 30:7118–7126).

Family M3

Thimet oligopeptidase (EC 3.4.24.15), a mammalian enzyme involved in the cytoplasmic degradation of small peptides.

Neurolysin (EC 3.4.24.16) (also known as mitochondrial oligopeptidase M or microsomal endopeptidase).

Mitochondrial intermediate peptidase precursor (EC 3.4.24.59) (MIP). It is involved the second stage of processing of some proteins imported in the mitochondrion.

Yeast saccharolysin (EC 3.4.24.37) (proteinase yscD) (Buchler et al. (1994) *Eur. J. Biochem.* 219:627–639).

*Escherichia coli* and related bacteria dipeptidyl carboxypeptidase (EC 3.4.15.5) (gene dcp).

*Escherichia coli* and related bacteria oligopeptidase A (EC 3.4.24.70) (gene opdA or prlC).

Yeast hypothetical protein YKL134c.

Family M4

Thermostable thermolysins (EC 3.4.24.27), and related thermolabile neutral proteases (bacillolysins) (EC 3.4.24.28) from various species of Bacillus.

Pseudolysin (EC 3.4.24.26) from *Pseudomonas aeruginosa* (gene lasB).

Extracellular elastase from *Staphylococcus epidermidis.*

Extracellular protease prt1 from *Erwinia carotovora.*

Extracellular minor protease smp from *Serratia marcescens.*

Vibriolysin (EC 3.4.24.25) from various species of Vibrio.

Protease prtA from *Listeria monocytogenes.*

Extracellular proteinase proA from *Legionella pneumophila.*

Family M5

Mycolysin (EC 3.4.24.31) from *Streptomyces cacaoi.*

Family M6

Immune inhibitor A from *Bacillus thuringiensis* (gene ina). Ina degrades two classes of insect antibacterial proteins, attacins and cecropins.

Family M7

Streptomyces extracellular small neutral proteases

Family M8

Leishmanolysin (EC 3.4.24.36) (surface glycoprotein gp63), a cell surface protease from various species of Leishmania.

Family M9

Microbial collagenase (EC 3.4.24.3) from *Clostridium perfringens* and *Vibrio alginolyticus.*

Family M10A

Serralysin (EC 3.4.24.40), an extracellular metalloprotease from Serratia.

Alkaline metalloproteinase from *Pseudomonas aeruginosa* (gene aprA).

Secreted proteases A, B, C and G from *Erwinia chrysanthemi.*

Yeast hypothetical protein YIL 108w.

Family M10B

Mammalian extracellular matrix metalloproteinases (known as matrixins) (Woessner (1991) *FASEB J.* 5:2145–2154): MMP-1 (EC 3.4.24.7) (interstitial collagenase), MMP-2 (EC 3.4.24.24) (72 Kd gelatinase), MMP-9 (EC 3.4.24.35) (92 Kd gelatinase), MMP-7 (EC 3.4.24.23) (matrylisin), MMP-8 (EC 3.4.24.34) (neutrophil collagenase), MMP-3 (EC 3.4.24.17) (stromelysin-1), MMP-10 (EC 3.4.24.22) (stromelysin-2), and MMP-11 (stromelysin-3), MMP-12 (EC 3.4.24.65) (macrophage metalloelastase).

Sea urchin hatching enzyme (envelysin) (EC 3.4.24.12), a protease that allows the embryo to digest the protective envelope derived from the egg extracellular matrix.

Soybean metalloendoproteinase 1.

Family M11

*Chlamydomonas reinhardtii* gamete lytic enzyme (GLE).

Family M12A

Astacin (EC 3.4.24.21), a crayfish endoprotease.

Meprin A (EC 3.4.24.18), a mammalian kidney and intestinal brush border metalloendopeptidase.

Bone morphogenic protein 1 (BMP-1), a protein which induces cartilage and bone formation and which expresses metalloendopeptidase activity. The Drosophila homolog of BMP-1 is the dorsal-ventral patterning protein tolloid.

Blastula protease 10 (BP 10) from *Paracentrotus lividus* and the related protein SpAN from *Strongylocentrotus purpuratus*.

*Caenorhabditis elegans* hypothetical proteins F42A10.8 and R151.5.

Choriolysins L and H (EC 3.4.24.67) (also known as embryonic hatching proteins LCE and HCE) from the fish *Oryzias lapides*. These proteases participate in the breakdown of the egg envelope, which is derived from the egg extracellular matrix, at the time of hatching.

Family M12B

Snake venom metalloproteinases (Hite et al. (1992) *Bio. Chem. Hoppe-Seyler* 373:381–385). This subfamily mostly groups proteases that act in hemorrhage. Examples are: adamalysin II (EC 3.4.24.46), atrolysin C/D (EC 3.4.24.42), atrolysin E (EC 3.4.24.44), fibrolase (EC 3.4.24.72), trimerelysin I (EC 3.4.25.52) and II (EC 3.4.25.53).

Mouse cell surface antigen MS2.

Family M13

Mammalian neprilysin (EC 3.4.24.11) (neutral endopeptidase) (NEP).

Endothelin-converting enzyme I (EC 3.4.24.71) (ECE-1), which processes the precursor of endothelin to release the active peptide.

Kell blood group glycoprotein, a major antigenic protein of erythrocytes. The Kell protein is very probably a zinc endopeptidase.

Peptidase O from *Lactococcus lactis* (gene pepO).

Family M27

Clostridial neurotoxins, including tetanus toxin (TeTx) and the various botulinum toxins (BoNT). These toxins are zinc proteases that block neurotransmitter release by proteolytic cleavage of synaptic proteins such as synaptobrevins, syntaxin and SNAP-25 (Montecucco et al. (1993) *Trends Biochem. Sci.* 18:324–327; Niemann et al. (1994) *Trends Cell Biol.* 4:179–185).

Family M30

*Staphylococcus hyicus* neutral metalloprotease.

Family M32

Thermostable carboxypeptidase 1 (EC 3.4.17.19) (carboxypeptidase Taq), an enzyme from *Thermus aquaticus* which is most active at high temperature.

Family M34

Lethal factor (LF) from *Bacillus anthracis*, one of the three proteins composing the anthrax toxin.

Family M35

Deuterolysin (EC 3.4.24.39) from *Penicillium citrinum* and related proteases from various species of Aspergillus.

Family M36

Extracellular elastinolytic metalloproteinases from Aspergillus.

From the tertiary structure of thermolysin, the position of the residues acting as zinc ligands and those involved in the catalytic activity are known. Two of the zinc ligands are histidines which are very close together in the sequence; C-terminal to the first histidine is a glutamic acid residue which acts as a nucleophile and promotes the attack of a water molecule on thecarbonyl carbon of the substrate.

Prolyl oligopeptidase family serine active site

The prolyl oligopeptidase family (Rawlings et al. (1991) *Biochem. J.* 279:907–911; Barrett et al. (1992) *Biol. Chem. Hoppe-Seyler* 373:353–360; Polgar et al. (1992) *Biol. Chem. Hoppe-Seyler* 373:361–366) consist of a number of evolutionary related peptidases whose catalytic activity seems to be provided by a charge relay system similar to that of the trypsin family of serine proteases, but which evolved by independent convergent evolution. The known members of this family include:

Prolyl endopeptidase (EC 3.4.21.26) (PE) (also called post-proline cleaving enzyme). PE is an enzyme that cleaves peptide bonds on the C-terminal side of prolyl residues. The sequence of PE has been obtained from a mammalian species (pig) and from bacteria (*Flavobacterium meningosepticum* and *Aeromonas hydrophila*); there is a high degree of sequence conservation between these sequences.

*Escherichia coli* protease II (EC 3.4.21.83) (oligopeptidase B) (gene prtB) which cleaves peptide bonds on the C-terminal side of lysyl and argininyl residues.

Dipeptidyl peptidase IV (EC 3.4.14.5) (DPP IV). DPP IV is an enzyme that removes N-terminal dipeptides sequentially from polypeptides having unsubstituted N-termini provided that the penultimate residue is proline.

Yeast vacuolar dipeptidyl aminopeptidase A (DPAP A) (gene: STE13) which is responsible for the proteolytic maturation of the alpha-factor precursor.

Yeast vacuolar dipeptidyl aminopeptidase B (DPAP B) (gene: DAP2).

Acylamino-acid-releasing enzyme (EC 3.4.19.1) (acylpeptide hydrolase). This enzyme catalyzes the hydrolysis of the amino-terminal peptide bond of an N-acetylated protein to generate a N-acetylated amino acid and a protein with a free amino-terminus.

A conserved serine residue has experimentally been shown (in *E. coli* protease II as well as in pig and bacterial PE) to be necessary for the catalytic mechanism. This serine, which is part of the catalytic triad (Ser, His, Asp), is generally located about 150 residues away from the C-terminal extremity of these enzymes (which are all proteins that contains about 700 to 800 amino acids).

Renal dipeptidase active site

Renal dipeptidase (rDP) (EC 3.4.13.19), also known as microsomal dipeptidase, is a zinc-dependent metalloenzyme which hydrolyzes a wide range of dipeptides. It is involved in renal metabolism of glutathione and its conjugates. It is a homodimeric disulfide-linked glycoprotein attached to the renal brush border microvilli membrane by a GPI-anchor.

A glutamate residue has recently been shown (Adachi et al. (1993) *Biochim. Biophys. Acta* 1163:42–48) to be important for the catalytic activity of rDP.

RDP seems to be evolutionary related to hypothetical proteins in the PQQ biosynthesis operons of *Acinetobacter calcoaceticus* and *Klebsiella pneumoniae*.

Aminopeptidase P and Proline Dipeptidase Signature

Aminopeptidase P (EC 3.4.11.9) is the enzyme responsible for the release of any N-terminal amino acid adjacent to a proline residue. Proline dipeptidase (EC 3.4.13.9) (prolidase) splits dipeptides with a prolyl residue in the carboxyl terminal position.

Bacterial aminopeptidase P II (gene pepP) (Yoshimoto et al. (1989) *J. Biochem.* 105:412–416), proline dipeptidase (gene pepQ) (Nakahigashi et al. (1990) *Nucleic Acids Res.* 18:6439–6439), and human proline dipeptidase (gene PEPD) (Endo et al. (1989) *J. Biol chem.* 264: 4476–4481) are evolutionary related. These proteins are manganese metalloenzymes.

Yeast hypothetical proteins YER078c and YFR006w and *Mycobacterium tuberculosis* hypothetical protein MtCY49.29c also belong to this family.

Methionine Aminopeptidase Signatures

Methionine aminopeptidase (EC 3.4.11.18) (MAP) is responsible for the removal of the amino-terminal (initiator) methionine from nascent eukaryotic cytosolic and cytoplasmic prokaryotic proteins if the penultimate amino acid is small and uncharged. All MAP studied to date are monomeric proteins that require cobalt ions for activity.

Two subfamilies of MAP enzymes are known to exist (Arfin et al. (1995) *Proc. Natl. Acad. Sci. U.S.A.* 92:7714–1128; Keeling et al. (1996) *Trends Biochem. Sci.* 21:285–286). While being evolutionary related, they only share a limited amount of sequence similarity mostly clustered around the residues shown, in the *Escherichia coli* MAP (Roderick et al. (1993) *Biochemistry* 32:3907–3912), to be involved in cobalt-binding.

The first family consists of enzymes from prokaryotes as well as eukaryotic MAP-1, while the second group is made up of archebacterial MAP and eukaryotic MAP-2. The second subfamily also includes proteins which do not seem to be MAP, but that are clearly evolutionary related such as mouse proliferation-associated protein 1 and fission yeast curved DNA-binding protein.

Matrixins Cysteine Switch

Mammalian extracellular matrix metalloproteinases (EC 3.4.24.-), also known as matrixins (Woessner (1991) *FASFB J.* 5:2145–2154) (see ), are zinc-dependent enzymes. They are secreted by cells in an inactive form (zymogen) that differs from the mature enzyme by the presence of an N-terminal propeptide. A highly conserved octapeptide is found two residues downstream of the C-terminal end of the propeptide. This region has been shown to be involved in autoinhibition of matrixins (Sanchez-Lopez et al. (1988) *J. Biol. Chem.* 266:11892–11899; Parks et al. (1991) *J. Biol. Chem.* 266:1584–1590); a cysteine within the octapeptide chelates the active site zinc ion, thus inhibiting the enzyme. This region has been called the "cysteine switch" or "autoinhibitor region".

A cysteine switch has been found in the following zinc proteases:

MMP-1 (EC 3.4.24.7) (interstitial collagenase).
MMP-2 (EC 3.4.24.24) (72 Kd gelatinase).
MMP-3 (EC 3.4.24.17) (stromelysin-1).
MMP-7 (EC 3.4.24.23) (matrilysin).
MMP-8 (EC 3.4.24.34) (neutrophil collagenase).
MMP-9 (EC 3.4.24.35) (92 Kd gelatinase).
MMP-10 (EC 3.4.24.22) (stromelysin-2).
MMP-11 (EC 3.4.24.-) (stromelysin-3).
MMP-12 (EC 3.4.24.65) (macrophage metalloelastase).
MMP-13 (EC 3.4.24.-) (collagenase 3).
MMP-14 (EC 3.4.24.-) (membrane-type matrix metalliproteinase 1).
MMP-15 (EC 3.4.24.-) (membrane-type matrix metalliproteinase 2).
MMP-16 (EC 3.4.24.-) (membrane-type matrix metalliproteinase 3).
Sea urchin hatching enzyme (EC 3.4.24.12) (envelysin) (Lepage et al. (1990) *EMBO J.* 93003–3012).
*Chlamydomonas reinhardtii* gamete lytic enzyme (GLE) (Kinshita et al. (1992) *Proc. Natl. Acad. Sci. U.S.A.* 89:4693–4697).

Serine Carboxypeptidases, Active Sites

All known carboxypeptidases are either metallo carboxypeptidases or serine carboxypeptidases (EC 3.4.16.5 and EC 3.4.16.6). The catalytic activity of the serine carboxypeptidases, like that of the trypsin family serine proteases, is provided by a charge relay system involving an aspartic acid residue hydrogen-bonded to a histidine, which is itself hydrogen-bonded to aserine (Liao et al. (1990) *J. Biol. Chem.* 265:6528–6531). Proteins known to be serine carboxypeptidases include, but are not limited to:

Barley and wheat serine carboxypeptidases I, II, and III (Sorenson et al. (1989) *Carlsberg Res. Commun.* 54:193–202).

Yeast carboxypeptidase Y (YSCY) (gene PRC1), a vacuolar protease involved in degrading small peptides.

Yeast KEX1 protease, involved in killer toxin and alpha-factor precursor processing.

Fission yeast sxa2, a probable carboxypeptidase involved in degrading or processing mating pheromones (Imai et al. (1992) *Mol. Cell. Biol.* 12:1827–1834).

*Penicillium janthinellum* carboxypeptidase S1 (Svendsen et al. (1993) *FEBS Lett.* 333:39043).

*Aspergullus niger* carboxypeptidase pepF.

*Aspergullus satoi* carboxypeptidase cpdS.

Vertebrate protective protein/cathepsin A (Galjart et al. (1991) *J. Biol. Chem* 266:14754–14762), a lysosomal protein which is not only a carboxypeptidase but also essential for the activity of both beta-galactosidase and neuraminidase.

Mosquito vitellogenic carboxypeptidase (VCP) (Cho et at. (1991) *Proc. Natl. Acad. Sci. U.S.A.* 88:10821–10824).

*Naegleria fowleri* virulence-related protein Nf314 (Hu et al. (1992) *Infect. Immun.* 60:2418–2424).

Yeast hypothetical protein YBR139w.

*Caenorhabditis elegans* hypothetical proteins C08H9.1, F13D12.6, F32A5.3, F41C3.5 and K10B2.2.

This family also includes:

Sorghum (s)-hydroxymandelonitrile lyase (EC 4.1.2.11) (hydroxynitrile lyase) (HNL) (Wajant et al. (1994) *Plant Mol. Biol.* 26:735–746), an enzyme involved in plant cyanogenesis.

The sequences surrounding the active site serine and histidine residues are highly conserved in all these serine carboxypeptidases.

Subtilases (Siezen et al. (1991) *Protein Eng.* 4:719–737; Siezen, R. J. (1992) In: Proceedings Subtilisin Symposium, Hamburg) are an extensive family of serine proteases whose catalytic activity is provided by a charge relay system similar to that of the trypsin family of serine proteases but which evolved by independent convergent evolution. The sequence around the residues involved in the catalytic triad (aspartic acid, serine and histidine) are completely different from that of the analogous residues in the trypsin serine proteases. The subtilase family is described below.

Proteasome A-type Subunits Signature

The proteasome (or macropain) (EC 3.4.99.46) (Rivett (1993) *Biochem. J.* 29: 1–10; Rivett (1989) *Arch. Biochem Biophys.* 268:1–8; Goldbert et al. (1992) *Nature* 357:375–379; Wilk (1993) *Enzyme Protein* 47:187–188; Hilt et a. (1996) *Trends Biochem. Sci.* 21:96–102) is an eukaryotic and archaebacterial multicatalytic proteinase complex that seems to be involved in an ATP/ubiquitin-dependent nonlysosomal proteolytic pathway. In eukaryotes the proteasome is composed of about 28 distinct subunits which form a highly ordered ring-shaped structure (20S ring) of about 700 Kd.

Most proteasome subunits can be classified, on the basis on sequence similarities into two groups, A and B. Subunits that belong to the A-type group are proteins of from 210 to 290 amino acids that share a number of conserved sequence regions. Subunits that are known to belong to this family include, but are not limited to:

Vertebrate subunits C2 (nu), C3, C8, C9, iota and zeta.

Drosophila PROS-25, PROS-28.1, PROS-29 and PROS-35.

Yeast C1 (PRS1), C5 (PRS3), C7-alpha (Y8) (PRS2), Y7, Y13, PRE5, PRE6 and PUP2.

*Arabidopsis thaliana* subunits alpha and PSM30.

*Thermoplasma acidophilum* alpha-subunit. In this archaebacteria the proteasome is composed of only two different subunits.

Proteasome B-type Subunits Signature

The proteasome (or macropain) (EC 34.99.46) (Rivett (1993) *Biochem. J.* 29:1–10; Rivett (1989) *Arch. Biochem Biophys.* 268:1–8; Goldbert et al. (1992) *Nature* 357:375–379; Wilk (1993) *Enzyme Protein* 47:187–188; Hilt et al. (1996) *Trends Biochem. Sci.* 21:96–102) is an eukaryotic and archaebacterial multicatalytic proteinase complex that seems to be involved in an ATP/ubiquitin-dependent nonlysosomal proteolytic pathway. In eukaryotes the proteasome is composed of about 28 distinct subunits which form a highly ordered ring-shaped structure (20S ring) of about 700 Kd.

Most proteasome subunits can be classified, on the basis on sequence similarities into two groups, A and B. Subunits that belong to the B-type group are proteins of from 190 to 290 amino acids that share a number of conserved sequence regions. Subunits that belong to this family include, but are not limited to:

Vertebrate subunits C5, beta, delta, epsilon, theta (C10-II), LMP2/RING12, C13 (LMP7/RING10), C7-I and MECL-1.

Yeast PRE1, PRE2 (PRG1), PRE3, PRE4, PRS3, PUP1 and PUP3.

Drosophila L(3)73AI.

Fission yeast pts1.

*Thermoplasma acidophilum* beta-subunit. In this archaebacteria the proteasome is composed of only two different subunits.

Serine proteases subtilase family, active sites

Subtilases (Siezen et al. (1991) *Protein Eng.* 4:719–737, Siezen, R. J. (1992) In: Proceedings Subtilisin Symposium, Hamburg) are an extensive family of serine proteases whose catalytic activity is provided by a charge relay system similar to that of the trypsin family of serine proteases but which evolved by independent convergent evolution. The sequence around the residues involved in the catalytic triad (aspartic acid, serine and histidine) are completely different from that of the analogous residues in the trypsin serine proteases. The subtilase family includes, but is not limited to, the following proteases.

Subtilisins (EC 3.4.21.62), these alkaline proteases from various Bacillus species have been the target of numerous studies in the past thirty years.

Alkaline elastase YaB from Bacillus sp. (gene ale).

Alkaline serine exoprotease A from *Vibrio alginolyticus* (gene proA).

Aqualysin I from *Thermus aquaticus* (gene pstI).

AspA from *Aeromonas salmonicida*.

Bacillopeptidase F (esterase) from *Bacillus subtilis* (gene bpf).

C5A peptidase from *Streptococcus pyogenes* (gene scpA).

Cell envelope-located proteases PI, PII, and PIII from *Lactococcus lactis*.

Extracellular serine protease from *Serratia marcescens*.

Extracellular protease from *Xanthomonas campestris*.

Intracellular serine protease (ISP) from various Bacillus.

Minor extracellular serine protease epr from *Bacillus subtilis* (gene epr).

Minor extracellular serine protease vpr from *Bacillus subtilis* (gene pr).

Nisin leader peptide processing protease nisP from *Lactococcus lactis*.

Serotype-specific antigene 1 from *Pasteurella haemolytica* (gene ssa1).

Thermitase (EC 3.4.21.66) from *Thermoactinomyces vulgaris*.

Calcium-dependent protease from *Anabaena variabilis* (gene prcA).

Halolysin from halophilic bacteria sp. 172p1 (gene hly).

Alkaline extracellular protease (AEP) from *Yarrowia lipolytica* (gene xpr2).

Alkaline proteinase from *Cephalosporium acremonium* (gene alp).

Cerevisin (EC 3.4.21.48) (vacuolar protease B) from yeast (gene PRB1).

Cuticle-degrading protease (pr1) from *Metarhizium anisopliae*.

KEX-1 protease from *Kluyveromyces lactis*.

Kexin (EC 3.4.21.61) from yeast (gene KEX-2).

Oryzin (EC 3.4.21.63) (alkaline proteinase) from Aspergillus (gene alp).

Proteinase K (EC 3.4.21.64) from *Tritirachium album* (gene proK).

Proteinase R from *Tritirachium album* (gene proR).

Proteinase T from *Tritirachium album* (gene proT).

Subtilisin-like protease III from yeast (gene YSP3).

Thermomycolin (EC 3.4.21.65) from *Malbranchea sulfurea*.

Furin (EC 3.4.21.85), neuroendocrine convertases 1 to 3 (NEC-1 to 3) and PACE4 protease from mammals, other vertebrates, and invertebrates. These proteases are involved in the processing of hormone precursors at sites comprised of pairs of basic amino acid residues (Barr, P. J. (1991) *Cell* 66:1–3).

Tripeptidyl-peptidase II (EC 3.4.14.10) (tripeptidyl aminopeptidase) from human.

Prestalk-specific proteins tagB and tagC from slime mold (Shaulsky et al. (1995) *Genes Dev.* 9:1111–1122). Both proteins consist of two domains: a N-terminal subtilase catalytic domain and a C-terminal ABC transporter domain.

Serine Proteases, Trypsin Family, Active Sites

The catalytic activity of the serine proteases from the trypsin family is provided by a charge relay system involving an aspartic acid residue hydrogen-bonded to a histidine, which itself is hydrogen-bonded to a serine. The sequences in the vicinity of the active site serine and histidine residues are well conserved in this family of proteases (Brenner (1988) *Nature* 334:528–530). Proteases that belong to the trypsin family include, but are not limited to:

Acrosin.

Blood coagulation factors VII, IX, X, XI and XII, thrombin, plasminogen, and protein C.

Cathepsin G.

Chymotrypsins.

Complement components C1r, C1s, C2, and complement factors B, D and I.

Complement-activating component of RA-reactive factor.

Cytotoxic cell proteases (granzymes A to H).

Duodenase I.

Elastases 1, 2, 3A, 3B (protease E), leukocyte (medullasin).

Enterokinase (EC 3.4.21.9) (enteropeptidase).

Hepatocyte growth factor activator.

Hepsin.

Glandular (tissue) kallikreins (including EGF-binding protein types A, B, and C, NGF-gamma chain, gamma-renin, prostate specific antigen (PSA) and tonin).

Plasma kallikrein.

Mast cell proteases (MCP) 1 (chymase) to 8.

Myeloblastin (proteinase 3) (Wegener's autoantigen).

Plasminogen activators (urokinase-type, and tissue-type).

Trypsins I, II, III, and IV.

Tryptases.

Snake venom proteases such as ancrod, batroxobin, cerastobin, flavoxobin, and protein C activator.

Collagenase from common cattle grub and collagenolytic protease from Atlantic sand fiddler crab.

Apolipoprotein(a).

Blood fluke cercarial protease.

Drosophila trypsin like proteases: alpha, easter, snake-locus.

Drosophila protease stubble (gene sb).

Major mite fecal allergen Der p III.

All the above proteins belong to family S1 in the classification of peptidases (Rawlings et al. (1994) *Meth. Enzymol.* 244:19–61) and originate from eukaryotic species. It should be noted that bacterial proteases that belong to family S2A are similar enough in the regions of the active site residues that they can be picked up by the same patterns. These proteases include, but are not limited to:

*Achromobacter lyticus* protease I.

Lysobacter alpha-lytic protease.

Streptogrisin A and B (Streptomyces proteases A and B).

*Streptomyces griseus* glutamyl endopeptidase II.

*Streptomyces fradiae* proteases 1 and 2.

Ubiquitin Carboxyl-Terminal Hydrolases Family 1 Cysteine Active Sites

Ubiquitin carboxyl-terminal hydrolases (EC 3.1.2.15) (UCH) (deubiquitinating enzymes) (Jentsch et al. (1991) *Biochim. Biophys. Acta* 1089:127–139) are thiol proteases that recognize and hydrolyze the peptide bond at the C-terminal glycine of ubiquitin. These enzymes are involved in the processing of poly-ubiquitin precursors as well as that of ubiquinated proteins.

There are two distinct families of UCH. The first class consist of enzymes of about 25 Kd and is currently represented by:

Mammalian isozymes L1 and L3.

Yeast YUH1.

Drosophila Uch.

One of the active site residues of class-1 UCH (Johnston et al. (1997) *EMBO J.* 16:3787–3796) is a cysteine.

Ubiquitin Carboxyl-Terminal Hydrolases Family 2 Signatures

Ubiquitin carboxyl-terminal hydrolases (EC 3.1.2.15) (UCH) (deubiquitinating enzymes) (Jentsch et al. (1991) *Biochim. Biophysi. Acta* 1089:127–139) are thiol proteases that recognize and hydrolyze the peptide bond at the C-terminal glycine of ubiquitin. These enzymes are involved in the processing of poly-ubiquitin precursors as well as that of ubiquinated proteins.

There are two distinct families of UCH. The second class (Papa et al. (1993) *Nature* 366:313–319) consist of large proteins (800 to 2000 residues) and is represented by:

Yeast UBP1, UBP2, UBP3, UBP4 (or DOA4/SSV7), UBP5, UBP7, UBP9, UBP11, UBP12 and UBP13.

Yeast hypothetical protein YBR058c.

Yeast hypothetical protein YFR010w.

Yeast hypothetical protein YMR304w.

Yeast hypothetical protein YMR223w.

Yeast hypothetical protein YNL186w.

Human tre-2.

Human isopeptidase T.

Human isopeptidase T-3.

Mammalian Ode-1.

Mammalian Unp.

Mouse Dub-1.

Drosophila fat facets protein (gene faf).

Mammalian faf homolog.

*Caenorhabditis elegans* hypothetical protein R10E11.3.

*Caenorhabditis elegans* hypothetical protein K02C4.3.

These proteins only share two regions of similarity. The first region contains a conserved cysteine which is probably implicated in the catalytic mechanism. The second region contains two conserved histidines residues, one of which is also probably implicated in the catalytic mechanism.

The identification and characterization of the novel genes encoding the novel human proteases is described. The invention is based, at least in part, on the identification of human genes encoding members of protease families, including but not limited to those described herein. The human protease family members were isolated based on a specific consensus motif or protein domain characteristic of a protease family of proteins. The search of the nucleic acid sequence database (usually derived from random cDNA library sequencing) was performed with one or more HMM motifs, a TBLASTN set, or both.

The TBLASTN set included a set of protein sequence probes which correspond to amino acid sequence motifs that are conserved in the protease family of proteins.

The HMM motif included a consensus sequence for a protein domain. Such consensus sequences can be found in a database of Hidden Markov Models (HMMs), e.g., the Pfam database, release 2.1, (http://www.sanger.ac.uk/Software/Pfam/HMM search). A description of the Pfam database can be found in Sonhammer et al. (1997) *Proteins* 23(3):405–420 and detailed description of HMMs can be found in, for example, Gribskov et al. (1990) *Meth. Enzymol.* 183:146–159; Gribskov et al. (1987) *Proc. Natl. Acad. Sci. USA* 84:4355–4358 Krogh et al. (1994) *J. Mol. Biol.* 235:1501–1531; and Stultz et al. (1993) *Protein Sci.* 2:305–314, the contents of which are incorporated herein by reference.

The sequences of the positive clones were determined and are set forth herein as SEQ ID NOS:1–33.

Polynucleotides

Accordingly, the invention provides isolated nucleic acid molecules comprising a nucleotide sequence selected from the group consisting of SEQ ID NOS: 1–33 and the complements thereof. The Sequence Listing shows the relationship between each nucleotide sequence and protease family.

In one embodiment, the isolated nucleic acid molecule has the formula:

$$5'(R_1)_n-(R_2)-(R_3)m3'$$

wherein, at the 5' end of the molecule $R_1$ is either hydrogen or any nucleotide residue when n=1, and is any nucleotide residue when n>1; at the 3' end of the molecule $R_3$ is either hydrogen, a metal or any nucleotide residue when m=1, and is any nucleotide residue when m>1; n and m are integers between about 1 and 5000; and $R_2$ is a nucleic acid having a nucleotide sequence selected from the group consisting of SEQ ID NOS: 1–33 and the complements of SEQ ID NOS: 1–33. The $R_2$ nucleic acid is oriented so that its 5' residue is bound to the 3' molecule of $R_1$, and its 3' residue is bound to the 5' molecule of $R_3$. Any stretch of nucleic acid residues denoted by either $R_1$ or $R_3$, which is greater than 1, is preferably a heteropolymer, but can also be a homopolymer. In certain embodiments, n and m are integers between about 1 and 2000, preferably between about 1 and 1000, and preferably between about 1 and 500. In other embodiments, the isolated nucleic acid molecule is at least about 50 nucleotides, preferably at least about 100 nucleotides, more preferably at least about 150 nucleotides, and even more preferably at least about 200 or more nucleotides in length. In still another embodiment, $R_1$ and $R_3$ are both hydrogen.

The term "protease polynucleotide" or "protease nucleic acid" refers to nucleic acid having the sequences shown in SEQ ID NO: 1–33 as well as variants and fragments of the polynucleotides of SEQ ID NO: 1–33.

An "isolated" protease nucleic acid is one that is separated from other nucleic acid present in the natural source of the protease nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the nucleic acid is isolated from flanking sequences such that it can be subjected to the specific manipulations described herein such as recombinant expression, preparation of probes and primers, and other uses specific to the protease nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector or other construct (i.e., as part of a larger constructed nucleic acid) are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The invention provides isolated polynucleotides encoding protease polypeptides.

The nucleic acid molecule can include all or a portion of the coding sequence. In one embodiment, the protease nucleic acid comprises only the coding region. The polynucleotides include, but are not limited to, the sequence encoding the mature polypeptide alone or the sequence encoding the mature polypeptide and additional coding sequences, such as a leader or secretory sequence (e.g., a pre-pro or pro-protein sequence). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes. The nucleic acid molecule can include the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification, such as those described herein.

Protease polynucleotides can be in the form of RNA, such as mRNA, or in the form of DNA, including cDNA and genomic DNA, obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Protease nucleic acids comprise the nucleotide sequences shown in SEQ ID NOS: 1–33, corresponding to human protease cDNAs.

The invention further provides variant protease polynucleotides, and fragments thereof, that differ from the nucleotide sequence shown in SEQ ID NOS: 1–33 due to degeneracy of the genetic code and thus encode the same protein as that encoded by the nucleotide sequences shown in SEQ ID NOS: 1–33.

The invention also provides protease nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, the variants can contain nucleotide substitutions, deletions, inversions and insertions.

Variation can occur in either or both the coding and non-coding regions. The variations can produce both conservative and non-conservative amino acid substitutions.

Typically, variants have a substantial identity with a nucleic acid molecule selected from the group consisting of SEQ ID NOS: 1–33 and the complements thereof.

Orthologs, homologs, and allelic variants can be identified using methods well known in the art. These variants comprise a nucleotide sequence encoding a protease that is 50–55% at least about 55%, typically at least about 70–75%, more typically at least about 80–85%, and most typically at least about 90–95% or more homologous to the nucleotide sequence shown herein or a fragment of these sequences. Such nucleic acid molecules can be readily identified as being able to hybridize under stringent conditions to a nucleotide sequence or fragments thereof selected from the group consisting of SEQ ID NOS: 1–33 and the complements thereof. In one embodiment, the variants hybridize under high stringency hybridization conditions (e.g., for selective hybridization) to a nucleotide sequence selected from SEQ ID NOS: 1–33. It is understood that stringent hybridization does not indicate substantial homology where it is due to general homology, such as poly A sequences, or sequences common to all or most proteins, sequences common to all or most proteases, or sequences common to all or most members of the protease family to which the specific protease belongs. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a protease at least 50–55%, 55% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, N.Y. (1989), 6.3.1–6.3.6, incorporated by reference. One example of stringent hybridization conditions are hybridization in 6×sodium chloride/sodium citrate (SSC) at about 45° C., followed by one or more washes in 0.2×SSC, 0.1% SDS at 50–65° C. In another non-limiting example, nucleic acid molecules are allowed to hybridize in 6×sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated protease nucleic acid molecule that hybridizes under stringent conditions to the sequence of SEQ ID NOS: 1–33 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to a nucleotide sequence selected from the group consisting of SEQ ID NOS: 1–33 and the complements of SEQ ID NOS: 1–33. In one embodiment, the nucleic acid consists of a portion of a nucleotide sequence selected from the group consisting of SEQ ID NOS: 1–33 and the complements SEQ ID NOS: 1–33. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic proteins or polypeptides described herein are useful. Additionally, nucleic acid sequences described herein can also be contigged to produce longer sequences (see, for example, http://bozeman.mbt.washington.edu/phrap.docs/phrap.html).

In a related aspect, the nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen el al., *Science* 254, 1497–1500 (1991). Typically, a probe comprises a region of nucleotide sequence that hybridizes under highly stringent conditions to at least about 15, typically about 20–25, and more typically about 40, 50 or 75 consecutive nucleotides of a nucleic acid selected from the group consisting of SEQ ID NOS: 1–33 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Fragments include nucleic acid sequences corresponding to specific amino acid sequences described herein. Further fragments can include subfragments of specific domains or sites, such as proteolytic cleavage sites, sites of interaction with a protein that modifies or activates the protease (an "effector" protein), or substrate binding sites. Nucleic acid fragments, according to the present invention, are not to be construed as encompassing those fragments that may have been disclosed prior to the invention.

Protease nucleic acid fragments include sequences corresponding to any domain described herein, subregions also described, and specific functional sites, such as binding and cleavage sites. Protease nucleic acid fragments also include combinations of the domains, regions, segments, and other functional sites described herein. A person of ordinary skill in the art would be aware of the many permutations that are possible.

It is understood that a protease fragment includes any nucleic acid sequence that does not include the entire gene.

Where the location of the domains or sites have been predicted by computer analysis, one of ordinary skill would appreciate that the amino acid residues constituting these domains can vary depending on the criteria used to define the domains.

The invention also provides protease nucleic acid fragments that encode epitope bearing regions of the protease proteins encoded by the cDNAs of the invention.

For example, the coding region of a protease gene can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of protease genes.

The nucleic acid molecules of the invention such as those described above can be identified and isolated using standard molecular biology techniques and the sequence information provided in SEQ ID NOS: 1–33. For example, nucleic acid molecules can be amplified and isolated by the polymerase chain reaction using synthetic oligonucleotide primers designed based on one or more of the sequences provided in SEQ ID NOS: 1–33 and the complements thereof. See generally PCR Technology: *Principles and Applications for DNA Amplification* (ed. H. A. Erlich, Freeman Press, New York, N.Y., 1992); PCR Protocols: *A Guide to Methods and Applications* (Eds. Innis, et al., Academic Press, San Diego, Calif., 1990); Mattila et al., *Nucleic Acids Res.* 19, 4967 (199 1); Eckert el al., *PCR Methods and Applications* 1, 17 (1991), PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Polynucleotide uses

The nucleic acid sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The protease polynucleotides are useful for probes, primers, and in biological assays. Where the polynucleotides are used to assess protease properties or functions, such as in the assays described herein, all or less than all of the entire cDNA can be useful. In this case, even fragments that may have been known prior to the invention are encompassed. Thus, for example, assays specifically directed to protease functions, such as assessing agonist or antagonist activity, encompass the use of known fragments. Further, diagnostic methods for assessing protease function can also be practiced with any fragment, including those fragments that may have been known prior to the invention. Similarly, in methods involving treatment of protease dysfunction, all fragments are encompassed including those which may have been known in the art.

The protease polynucleotides are useful as a hybridization probe for cDNA and genomic DNA to isolate a full-length cDNA and genomic clones encoding the protease polypeptides and to isolate cDNA and genomic clones that correspond to variants producing the same protease polypeptides or the other types of variants described herein. Variants can be isolated from the same tissue and organism from which the polypeptides were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the protease. Accordingly, it could be derived from 5' noncoding regions, the coding region, and 3' noncoding regions.

The nucleic acid probe can be, for example, the full-length cDNA sequence of SEQ ID NOS: 1–33, or fragments thereof, such as an oligonucleotide of at least 12, 15, 30, 50, 100, 250 or 500 nucleotides in length and sufficient to specifically hybridize under stringent conditions to mRNA or DNA. For example, the nucleic acid probe can be all or a portion of SEQ ID NOS: 1–33, or the complement of SEQ ID NOS: 1–33, or a portion thereof. Other suitable probes for use in the diagnostic assays of the invention are described herein.

Fragments of the polynucleotides described herein are also useful to synthesize larger fragments or full-length polynucleotides described herein. For example, a fragment can be hybridized to any portion of an mRNA and a larger or full-length cDNA can be produced.

Antisense nucleic acids of the invention can be designed using the nucleotide sequences of SEQ ID NOS: 1–33, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid) will be of an antisense orientation to a target nucleic acid of interest.

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell proteases in vivo), or agents facilitating transport across the cell membrane (see, e.g., Letsinger et al. (1989) *Proc. Natl. Acad Sci. USA* 86:6553–6556; Lemaitre et al. (1987) *Proc. Natl. Acad. Sci. USA* 84:648–652; PCT Publication No. WO88/0918) or the blood brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The protease polynucleotides are also useful as primers for PCR to amplify any given region of a protease polynucleotide.

The protease polynucleotides are also useful for constructing recombinant vectors. Such vectors include expression vectors that express a portion of, or all of, the protease polypeptides. Vectors also include insertion vectors, used to integrate into another polynucleotide sequence, such as into the cellular genome, to alter in situ expression of protease genes and gene products. For example, an endogenous protease coding sequence can be replaced via homologous recombination with all or part of the coding region containing one or more specifically introduced mutations.

The protease polynucleotides are also useful for expressing antigenic portions of the proteases.

The protease polynucleotides are also useful as probes for determining the chromosomal positions of the proteases by means of in situ hybridization methods.

Once the nucleic acid (or a portion of the sequence) has been isolated, it can be used to map the location of the gene on a chromosome. The mapping of the sequences to chromosomes is an important first step in correlating these sequences with genes associated with disease. Briefly, genes can be mapped to chromosomes by preparing PCR primers (preferably 15–25 bp in length) from the nucleic acid molecules described herein. Computer analysis of the sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the appropriate nucleotide sequences will yield an amplified fragment.

PCR mapping of somatic cell hybrids is a rapid procedure for assigning a particular sequence to a particular chromosome. Three or more sequences can be assigned per day using a single thermal cycle. Using the nucleic acid molecules of the invention to design oligonucleotide primers, sublocalization can be achieved with panels of fragments from specific chromosomes. Other mapping strategies which can similarly be used to map a specified sequence to its chromosome include in situ hybridization (described in Fan, Y et al. (1990) *PNAS*, 97:6223–27), pre-screening with labeled flow-sorted chromosomes, and pre-selection by hybridization to chromosome specific cDNA libraries.

Fluorescence in situ hybridization (FISH) of a nucleotide sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a nucleotide sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J et al. (1987) *Nature*, 325:783–787.

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible form chromosome spreads or detectable using PCR based on that DNA sequence. Ultimately, complete sequencing of genes from several individuals can be performed to confirm the presence of a mutation and to distinguish mutations from polymorphisms.

The polynucleotide probes are also useful to determine patterns of the presence of the gene encoding the proteases and their variants with respect to tissue distribution, for example, whether gene duplication has occurred and whether the duplication occurs in all or only a subset of tissues. The genes can be naturally-occurring or can have been introduced into a cell, tissue, or organism exogenously.

The polynucleotides are also useful for designing ribozymes corresponding to all, or a part, of the mRNA produced from genes encoding the polynucleotides described herein.

The polynucleotides are also useful for constructing host cells expressing a part, or all, of the protease polynucleotides and polypeptides.

The polynucleotides are also useful for constructing transgenic animals expressing all, or a part, of the protease polynucleotides and polypeptides.

The polynucleotides are also useful as hybridization probes for determining the level of protease nucleic acid expression. Accordingly, the probes can be used to detect the presence of, or to determine levels of, protease nucleic acid in cells, tissues, and in organisms. The nucleic acid whose level is determined can be DNA or RNA, including mRNA. Accordingly, probes corresponding to the polypeptides described herein can be 10 used to assess gene copy number in a given cell, tissue, or organism. This is particularly relevant in cases in which there has been an amplification of the protease genes.

Alternatively, the probe can be used in an in situ hybridization context to assess the position of extra copies of the protease genes, as on extrachromosomal elements or as integrated into chromosomes in which the protease gene is not normally found, for example as a homogeneously staining region.

These uses are relevant for diagnosis of disorders involving an increase or decrease in protease expression relative to normal, such as a proliferative disorder, a differentiative or developmental disorder, or a hematopoietic disorder.

Thus, the present invention provides a method for identifying a disease or disorder associated with aberrant expression or activity of protease nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease, such as by measuring a level of a protease-encoding nucleic acid in a sample of cells from a subject e.g., mRNA or genomic DNA, or determining if a protease gene has been mutated.

Nucleic acid expression assays are useful for drug screening to identify compounds that modulate protease nucleic acid expression (e.g., antisense, polypeptides, peptidomimetics, small molecules or other drugs). A cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. The modulator may bind to the nucleic acid or indirectly modulate expression, such as by interacting with other cellular components that affect nucleic acid expression.

The invention thus provides a method for identifying a compound that can be used to treat a disorder associated with nucleic acid expression of the protease gene. The method typically includes assaying the ability of the compound to modulate the expression of the protease nucleic acid and thus identifying a compound that can be used to treat a disorder characterized by undesired protease nucleic acid expression.

The assays can be performed in cell-based and cell-free systems. Cell-based assays include cells naturally expressing the protease nucleic acid or recombinant cells genetically engineered to express specific nucleic acid sequences.

Modulatory methods can be performed in vitro (e.g., by culturing the cell with the agent) or, alternatively, in vivo (e.g., by administering the agent to a subject) in patients or in transgenic animals.

The assay for protease nucleic acid expression can involve direct assay of nucleic acid levels, such as mRNA levels, or on collateral compounds involved in the pathway in which the protease is found. Further, the expression of genes that are up- or down-regulated in response to the protease function in the pathway can also be assayed. In this embodiment the regulatory regions of these genes can be operably linked to a reporter gene such as luciferase.

Accordingly, the invention provides methods of treatment, with the nucleic acid as a target, using a compound identified through drug screening as a gene modulator to modulate protease nucleic acid expression. Modulation includes both up-regulation (i.e. activation or agonization) or down-regulation (suppression or antagonization) or effects on nucleic acid activity (e.g. when nucleic acid is mutated or improperly modified) Treatment is of disorders characterized by aberrant expression or activity of nucleic acid.

One aspect of the invention relates to diagnostic assays for determining nucleic acid expression as well as activity in the context of a biological sample (e.g., blood, serum, cells, tissue) to thereby determine whether an individual has a disease or disorder, or is at risk of developing a disease or disorder, associated with aberrant expression or activity. Such assays can be used for prognostic or predictive purpose to thereby prophylactically treat an individual prior to the onset of a disorder characterized by or associated with expression or activity of the nucleic acid molecules.

The protease polynucleotides are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The protease polynucleotides are also useful in diagnostic assays for qualitative changes in protease nucleic acid, and particularly in qualitative changes that lead to pathology. The polynucleotides can be used to detect mutations in protease genes and gene expression products such as mRNA. The polynucleotides can be used as hybridization probes to detect naturally-occurring genetic mutations in a protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of a protease gene associated with a dysfunction provides a diagnostic tool for an active disease or susceptibility to disease when the disease results from overexpression, underexpression, or altered expression of a protease.

Individuals carrying mutations in the protease gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA*, 87:1874–1878), transcriptional amplification system (Kwoh, D. Y. et al., (1989) *Proc. Natl. Acad. Sci. USA*, 86:1173–1177), Q-Beta Replicase (Lizardi, P. M. et al., (1988) *Bio/Technology*, 6:1197), or any other nucleic acid amplification method, followed by the detection of the amplified molecules using techniques well known to those of skill in the art. These detection schemes are especially useful for the detection of nucleic acid molecules if such molecules are present in very low numbers.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and SI protection or the chemical cleavage method.

Furthermore, sequence differences between a mutant protease gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)).

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis*, 15:1657–1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039. In other embodiments, electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.*, 7: 5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin, M. T. et al. (1996) *Human Mutation*, 7:244–255; Kozal, M. J. et al. (1996) *Nature Medicine*, 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. Pharmacogenomics deal with clinically significant hereditary variations in the response to drugs due to altered drug disposition and abnormal action in affected persons. See, e.g., Eichelbaum, M., *Clin. Exp. Pharmacol. Physiol.* 23(10–11):983–985 (1996), and Linder, M. W., *Clin. Chem.* 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease in which one or more of the protease functions in one population is different from those in another population.

The protease polynucleotides are thus useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in a protease gene that results in altered affinity for substrate or effector could result in an excessive or decreased drug effect with standard concentrations of effector that activates the protease or substrate cleaved by the protease. Accordingly, the protease polynucleotides described herein can be used to assess the mutation content of the protease gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The protease polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The protease polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the protease sequence can be used to provide an alternative technique which determines the actual DNA sequence of selected fragments in the genome of an individual. Thus, the protease sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The protease sequences can be used to obtain such identification sequences from individuals and from tissue. The sequences represent unique fragments of the human genome. Each of the sequences described herein can, to some degree, be used as a standard against which DNA from an individual can be compared for identification purposes. The noncoding sequences of these sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The protease polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The protease polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique. Examples of polynucleotide reagents include the nucleic acid molecules or the invention, or portions thereof, e.g., fragments having a length of at least 20 bases, preferably at least 30 bases.

The protease polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of protease probes can be used to identify tissue by species and/or by organ type.

In a similar fashion, these primers and probes can be used to screen tissue culture for contamination (i.e. screen for the presence of a mixture of different types of cells in a culture).

Alternatively, the protease polynucleotides can be used directly to block transcription or translation of protease gene sequences by means of antisense or ribozyme constructs. Thus, in a disorder characterized by abnormally high or undesirable protease gene expression, nucleic acids can be directly used for treatment.

The protease polynucleotides are thus useful as antisense constructs to control protease gene expression in cells, tissues, and organisms. A DNA antisense polynucleotide is designed to be complementary to a region of the gene involved in transcription, preventing transcription and hence production of protease protein. An antisense RNA or DNA polynucleotide would hybridize to the mRNA and thus block translation of mRNA into protease protein.

Examples of antisense molecules useful to inhibit nucleic acid expression include antisense molecules complementary to a fragment of any 5' untranslated regions present in SEQ ID NOS: 1–33 which also includes the start codon and antisense molecules which are complementary to a fragment of any 3' untranslated region present in SEQ ID NOS: 1–33.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding and cleavage site.

The protease polynucleotides also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. For example, the kit can comprise reagents such as a labeled or labelable nucleic acid (probe or primer) or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease mRNA or DNA.

Polypeptides

The invention thus relates to novel proteases having the deduced amino acid sequences encoded by the open reading frames present in the nucleic acid molecules of SEQ ID NOS: 1–33.

The term "protease polypeptide" or "protease" refers to a protein sequence encoded by the nucleic acid sequences represented by SEQ ID NOS: 1–33. The term "protease" or "protease polypeptide", however, further includes the numerous variants described herein, as well as fragments derived from the polypeptides and variants.

The present invention thus provides an isolated or purified protease polypeptides and variants and fragments thereof.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%/o, or less than about 5% of the volume of the protein preparation.

In some instances, the protease will be associated with cellular membranes. This could include intracellular membranes or the outer cellular membrane. In either case, a protease is considered isolated if it is part of a purified membrane preparation or if it is purified and then reconstituted into membrane vesicles or liposomes.

The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid comprising a nucleotide sequence selected from the group consisting of SEQ ID NOS: 1–33 and the complements thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide encoded by a nucleic acid comprising a nucleotide sequence selected from the group consisting of SEQ ID NOS: 1–33 and the complements thereof. Variants also include proteins substantially homologous to the protease but derived from another organism, i.e., an ortholog. Variants also include proteins that are substantially homologous to the protease that are produced by chemical synthesis. Variants also include proteins that are substantially homologous to the protease that are produced by recombinant methods. It is understood, however, that variants exclude any amino acid sequences disclosed prior to the invention.

As used herein, two proteins (or a region of the proteins) are substantially homologous when the amino acid sequences are at least about 50–55%, 55–60%, typically at least about 70–75%, more typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of a nucleic acid sequence selected from the group consisting of SEQ ID NOS: 1–33, or portion thereof under stringent conditions as more described above.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptide. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247 1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished by well-known methods such as using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al., *Proc. Natl. Acad. Sci. USA* 90:5873–5877 (1993). Such an algorithm is incorporated into the NBLAST and XBLAST programs (version 2.0) as described in Altschul et al., *Nucleic Acids Res.*, 25:3389–3402 (1997). When utilizing BLAST and Gapped BLAST programs, the default parameters of the respective programs (e.g., NBLAST) can be used. See http://www.ncbi.nlm.nih.gov. In one embodiment, parameters for sequence comparison can be set at score=100, wordlength= 12, or can be varied (e.g., W=5 or W=20).

In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.* 10:3–5; and FASTA described in Pearson and Lipman (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to substrate binding, subcellular localization, such as membrane association, and proteolytic cleavage, effector binding, effector modification of the protease, other modification sites, or site of interaction with any other protein.

Fully functional variants typically contain only conservative variation or variation in non-critical residues or in non-critical regions. Functional variants can also contain substitution of similar amino acids which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the protease. This includes preventing immunogenicity from pharmaceutical formulations by preventing protein aggregation.

Useful variations further include alteration of substrate binding and cleavage characteristics. For example, one embodiment involves a variation at the binding site that results in binding but not release, or slower release, of substrate. A further useful variation at the same sites can result in a higher affinity for substrate. Useful variations also include changes that provide for affinity for another substrate. Another useful variation includes one that allows binding but which prevents proteolysis of the substrate. Another useful variation includes variation in the domain that provides for reduced or increased binding by the appropriate activator (effector) or for binding by a different activator than the one with which the protease is normally associated. Another useful variation provides a fusion protein in which one or more domains or subregions is operationally fused to one or more domains or subregions from another protease.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as protease binding, cleavage, or in vitro, or in vitro proliferative activity. Sites that are critical for protease binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

Substantial homology can be to the entire nucleic acid or amino acid sequence or to fragments of these sequences.

The invention also includes polypeptide fragments of the polypeptides of the invention Fragments can be derived from a polypeptide encoded by a nucleic acid comprising a nucleotide sequence selected from the group consisting of SEQ ID NOS: 1–33 and the complements thereof. However, the invention also encompasses fragments of the variants of the polypeptides encoded by the nucleic acid described herein.

In one embodiment, the fragment is or includes an open reading frame. Open reading frames can be determined by routine computerized homology search procedures.

The fragments to which the invention pertains, however, are not to be construed as encompassing fragments that may be disclosed prior to the present invention.

As used herein, a fragment comprises at least 10 contiguous amino acids. Fragments can retain one or more of the biological activities of the protein, for example the ability to bind to a substrate or activator, as well as fragments that can be used as an immunogen to generate protease antibodies.

Biologically active fragments (peptides which are, for example, 10, 12, 15, 20, 30, 35, 36, 37, 38, 39, 40, 50, 100 or more amino acids in length) can comprise a domain or region, as indicated, identified by analysis of the polypeptide sequence by well-known methods, e.g., cleavage sites, substrate binding sites, glycosylation sites, cAMP and cGMP-dependent phosphorylation sites, N-myristoylation sites, activator binding sites, casein kinase II phosphorylation sites, palmitoylation sites, amidation sites, or parts of any of these. Such domains or sites can be identified by means of routine procedures for computerized homology or motif analysis.

Fragments further include combinations of the various functional regions described herein. Other fragments include the mature protein. Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

Accordingly, possible fragments include but are not limited to fragments defining a substrate-binding site, fragments defining a phosphorylation site, fragments defining membrane association, fragments defining glycosylation sites, fragments defining interaction with activators and fragments defining myristoylation sites. By this is intended a discrete fragment that provides the relevant function or allows the relevant function to be identified. In a preferred embodiment, the fragment contains the substrate or activator-binding site.

The invention also provides fragments with immunogenic properties. These contain an epitope-bearing portion of the protease and variants. These epitope-bearing peptides are useful to raise antibodies that bind specifically to a protease polypeptide or region or fragment. These peptides can contain at least 10, 12, at least 14, or between at least about 15 to about 30 amino acids.

Non-limiting examples of antigenic polypeptides that can be used to generate antibodies include peptides derived from the amino terminal extracellular domain or any of the extracellular loops. Regions having a high antigenicity index can be determined by routine computerized amino acid sequence analysis. However, intracellularly-made antibodies ("intrabodies") are also encompassed, which would recognize intracellular peptide regions.

The polypeptides (including variants and fragments which may have been disclosed prior to the present invention) are useful for biological assays related to proteases. Such assays involve any of the known protease functions or activities or properties useful for diagnosis and treatment of protease-related conditions.

The epitope-bearing protease and polypeptides may be produced by any conventional means (Houghten, R. A., *Proc. Natl. Acad Sci. USA* 82:5131–5135 (1985)). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the protease fragment and an additional region fused to the carboxyl terminus of the fragment.

The invention thus provides chimeric or fusion proteins. These comprise a protease amino acid sequence operatively linked to a heterologous protein having an amino acid sequence not substantially homologous to the protease. "Operatively linked" indicates that the protease sequence and the heterologous protein are fused in-frame. The heterologous protein can be fused to the N-terminus or C-terminus of the protease sequence.

In one embodiment the fusion protein does not affect protease function per se. For example, the fusion protein can be a GST-fusion protein in which the protease sequences are fused to the C-terminus of the GST sequences or an influenza HA marker. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant protease. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett el al. (*J. Mol. Recog.* 8:52–58 (1995)) and Johanson et al. (*J. Biol. Chem.* 2 70, 16:9459–9471 (1995)). Thus, this invention also encompasses soluble fusion proteins containing a protease polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease encoding nucleic acid can be cloned into such an expression vector such that the fusion moiety is linked in-frame to the protease sequence.

Another form of fusion protein is one that directly affects protease functions. Accordingly, a polypeptide is encompassed by the present invention in which one or more of the protease domains (or parts thereof) has been replaced by homologous domains (or parts thereof) from another protease or other type of protease. Accordingly, various permutations are possible. The substrate binding, or subregion thereof, can be replaced, for example, with the corresponding domain or subregion from another substrate for the protease. Thus, chimeric proteases can be formed in which one or more of the native domains or subregions has been replaced.

The isolated protease sequence can be purified from cells that naturally express it, purified from cells that have been altered to express it (recombinant), or synthesized using known protein synthesis methods.

In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

As is also well known, polypeptides are not always entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http:H/www.ncbi.nlm.nih.gov.

The protease polypeptides are useful for producing antibodies specific for the protease, regions, or fragments.

The polypeptides (including variants and fragments which may have been disclosed prior to the present invention) are useful for biological assays related to proteases. Such assays involve any of the known protease functions or activities or properties useful for diagnosis and treatment of protease-related conditions.

The polypeptides are also useful in drug screening assays, in cell-based or cell-free systems. Cell-based systems can be native, i.e., cells that normally express the protease protein, as a biopsy or expanded in cell culture. In one embodiment, however, cell-based assays involve recombinant host cells expressing the protease protein.

The polypeptides can be used to identify compounds that modulate protease activity. Such compounds can increase or decrease affinity or rate of binding to a known substrate or activator, compete with substrate or activator for binding to the protease, or displace substrate or activator bound to the protease. Both protease protein and appropriate variants and fragments can be used in high-throughput screens to assay candidate compounds for the ability to bind to the protease. These compounds can be further screened against a functional protease to determine the effect of the compound on the protease activity. Compounds can be identified that activate (agonist) or inactivate (antagonist) the protease to a desired degree. Modulatory methods can be performed in vitro (e.g., by culturing the cell with the agent) or, alternatively, in vivo (e.g., by administering the agent to a subject).

The protease polypeptides can be used to screen a compound for the ability to stimulate or inhibit interaction between the protease protein and a target molecule that normally interacts with the protease protein. The target can be a component of the pathway with which the protease normally interacts. The assay includes the steps of combining the protease with a candidate compound under conditions that allow the protease or fragment to interact with the target molecule, and to detect the formation of a complex between the protein and the target or to detect the biochemical consequence of the interaction with the protease and the target, such as any of the associated effects of proteolytic cleavage, such as detecting the induction of a reporter gene (comprising a target-responsive regulatory element operatively linked to a nucleic acid encoding a detectable marker, e.g., luciferase), detecting a cellular response, for example, development, differentiation or rate of proliferation detection of activation of the substrate, or change in substrate levels (i.e., level of end product).

Determining the ability of the protein to bind to a target molecule can also be accomplished using a technology such as real-time Bimolecular Interaction Analysis (BIA). Sjolander, S. and Urbaniczky, C. (1991) *Anal. Chem.*, 63:2338–2345 and Szabo et al. (1995) *Curr. Opin. Struct. Biol.*, 5:699–705, As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. U.S.A.*, 90:6909, Erb et al. (I 994) *Proc. Natl. Acad. Sci. U.S.A.*, 91:11422; Zuckermann et al. (1994). *J. Med. Chem.*, 37:2678; Cho et al.(1993) *Science*, 261:1303; Carell et al. (1994) *Angew. Chem. Int. Ed. Engl.*, 33:2059; Carell et al. (1994) *Angew. Chem. Int. Ed. Engl.*, 33:2061; and in Gallop et al. (1994) *J. Med. Chem.*, 37:1233.

Libraries of compounds may be presented in solution (e.g., Houghten (1992) *Biotechniques*, 13:412–421), or on beads (Lam(1991) *Nature*, 354:82–84), chips (Fodor (1993) *Nature*, 364;555–556), bacteria(Ladner U.S. Pat. No. 5,223, 409), spores (Ladner U.S. Pat. No. '409), plasmids (Cull et al.(1992) *Proc. Natl. Acad. Sci. U.S.A.*, 89:1865–1869) or on phage (Scott and Smith (1990) *Science*, 249:386–390); (Devlin (1990) *Science*, 249:404–406); (Cwirla et al. (1990) *Proc. Natl. Acad. Sci.*, 97:6378–6382); (Felici (1991) *J. Mol. Biol.*, 222:301–310); (Ladner supra).

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length protease or fragment that competes for substrate or activator binding. Other candidate compounds include mutant proteases or appropriate fragments containing mutations that affect protease function and thus compete for substrate, activator or other protein that interacts with the protease. Accordingly, a fragment that competes for substrate or activator, for example with a higher affinity, or a fragment that binds substrate or activator but does not allow release, is encompassed by the invention.

The invention provides other end points to identify compounds that modulate (stimulate or inhibit) protease activity. The assays typically involve an assay of events in the pathway in which the protease is found that indicate protease activity. Thus, the expression of genes that are up- or down-regulated in response to the protease protein dependent cascade can be assayed. In one embodiment, the regulatory region of such genes can be operably linked to a marker that is easily detectable, such as luciferase. Alternatively, modification of the protease protein, or a protease protein target, could also be measured.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric proteases in which a domain, or parts thereof, are replaced by heterologous domains or subregions. For example, a substrate-binding region can be used that interacts with a different substrate than that which is recognized by the native protease. Accordingly, a different set of pathway components is available as an end-point assay for activation. Alternatively, a portion or subregions can be replaced with a portion or subregions specific to a host cell that is different from the host cell from which the domain is derived. This allows for assays to be performed in other than the specific host cell from which the protease is derived. Alternatively, the substrate or activator could be replaced by a domain (and/or other binding region) binding a different substrate or activator, thus providing an assay for test compounds that interact with the heterologous domain (or region) but still cause the events in the pathway. Finally, activation can be detected by a reporter gene containing an easily detectable coding region operably linked to a transcriptional regulatory sequence that is part of the native signal transduction pathway.

The protease polypeptides are also useful in competition binding assays in methods designed to discover compounds that interact with the protease. Thus, a compound is exposed to a protease polypeptide under conditions that allow the compound to bind or to otherwise interact with the polypeptide. Soluble polypeptide is also added to the mixture. If the test compound interacts with the soluble polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

Determining the ability of the test compound to interact with the polypeptide can also comprise determining the ability of the test compound to preferentially bind to the polypeptide as compared to the ability of the native counterpart, such as activator or substrate, or a biologically active portion thereof, to bind to the polypeptide.

To perform cell free drug screening assays, it is desirable to immobilize either the protease, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/protease fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule; as well as enzyme-linked assays which rely on detecting an enzymatic activity associated with the target molecule.

Modulators of protease activity identified according to these drug screening assays can be used to treat a subject with a disorder mediated by the protease pathway, by treating cells that express the protease. These methods of treatment include the steps of administering the modulators of protein activity in a pharmaceutical composition as described herein, to a subject in need of such treatment. The compounds may be tested first in an animal model to determine safety and efficacy.

The protease polypeptides are thus useful for treating a protease-associated disorder characterized by aberrant expression or activity of a protease. In one embodiment, the method involves administering an agent (e.g., an agent identified by a screening assay described herein), or combination of agents that modulates (e.g., upregulates or downregulates) expression or activity of the protein. In another embodiment, the method involves administering a protein as therapy to compensate for reduced or aberrant expression or activity of the protein. Accordingly, methods for treatment include the use of soluble protease or fragments of the protease protein that compete, for example, with activator or substrate binding. These proteases or fragments can have a higher affinity for the activator or substrate so as to provide effective competition.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. Another example of such a situation is where the subject has a proliferative disease (e.g., cancer) or a disorder characterized by an aberrant hematopoietic response. Yet another example of such a situation is where it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317, Zervos et al. (1993) *Cell*, 72:223–232; Madura et al. (1993) *J. Biol. Chem.*, 268:12046–12054; Bartel et al. (1993) *Biotechniques*, 14:920–924; Iwabuchi et al. (1993) *Oncogene*, 8:1693–1696; and Brent WO94/10300), to identify other proteins (captured proteins) which bind to or interact with the proteins of the invention and modulate their activity. Such captured proteins are also likely to be involved in the pathway that includes by the proteins of the invention as, for example, downstream elements of a protease-mediated pathway.

The protease polypeptides also are useful to provide a target for diagnosing a disease or predisposition to disease mediated by the protease, such as a proliferative disorder, a differentiative or developmental disorder, or a hematopoietic disorder. Accordingly, methods are provided for detecting the presence, or levels of the protease in a cell, tissue, or organism. The method can involve contacting a biological sample with a compound capable of interacting with the protease such that the interaction can be detected.

One agent for detecting a protease is an antibody capable of selectively binding to the protease. A biological sample includes tissues, cells and biological fluids isolated from a subject, as well as tissues, cells and fluids present within a subject.

The protease also provides a target for diagnosing active disease, or predisposition to disease, in a patient having a variant protease. Thus, protease can be isolated from a biological sample, assayed for the presence of a genetic mutation that results in aberrant protease. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in activator, substrate, or antibody-binding pattern, altered isoelectric point, direct amino acid sequencing, and any other of the known assay techniques useful for detecting mutations in a protein.

In vitro techniques for detection of protease include enzyme linked immunosorbent assays (ELISAs), Western blots, immunoprecipitations and immunofluorescence. Alternatively, the protein can be detected in vivo in a subject by introducing into the subject a labeled anti-protease antibody. For example, the antibody can be labeled with a radioactive marker whose presence and location in a subject can be detected by standard imaging techniques. Particularly useful are methods which detect the allelic variant of a protease expressed in a subject and methods which detect fragments of a protease in a sample.

It is also within the scope of this invention to determine the ability of a test compound to interact with the polypeptide without the labeling of any of the interactants. For example, a microphysiometer can be used to detect the interaction of a test compound with the polypeptide without the labeling of either the test compound or the polypeptide. McConnell, H. M. et al. (1992) *Science*, 257:1906–1912.

The present invention provides for both prophylactic and therapeutic methods of treating a subject at risk of (or susceptible to) a disorder or having a disorder associated with aberrant expression or activity of proteins of the invention. Administration of a prophylactic agent can occur prior to the manifestation of symptoms characteristic of the aberrancy, such that a disease or disorder is prevented or, alternatively, delayed in its progression.

With regard to both prophylactic and therapeutic methods of treatment, such treatments may be specifically tailored or modified, based on knowledge obtained from the field of pharmacogenomics. The polypeptides thus provide a target to ascertain a genetic predisposition that can affect treatment modality. Thus, in a substrate-based treatment, polymorphism may give rise to substrate or activator-binding regions that are more or less active in substrate or activator binding, and protease activation or proteolysis. Accordingly, activator or substrate dosage would necessarily be modified to maximize the therapeutic effect within a given population containing a polymorphism. As an alternative to genotyping, specific polymorphic polypeptides could be identified.

The protease polypeptides are also useful for monitoring therapeutic effects during clinical trials and other treatment. Thus, the therapeutic effectiveness of an agent that is designed to increase or decrease gene expression, protein levels or protease activity can be monitored over the course of treatment using the polypeptides as an end-point target. The monitoring can be, for example, as follows: (i) obtaining a pre-administration sample from a subject prior to administration of the agent, (ii) detecting the level of expression of a specified protein in the pre-administration sample; (iii) obtaining one or more post-administration samples from the subject; (iv) detecting the level of expression or activity of the protein in the post-administration samples, (v) comparing the level of expression or activity of the protein in the pre-administration sample with the protein in the post-administration sample or samples; and (vi) increasing or decreasing the administration of the agent to the subject accordingly.

The invention also comprises kits for detecting a protease protein. The kit can comprise a labeled compound or agent capable of detecting protein in a biological sample, such as an antibody or other binding compound; means for determining the amount of in the sample; and means for comparing the amount of in the sample with a standard. The compound or agent can be packaged in a suitable container. The kit can further comprise instructions for using the kit to detect the protein.

Antibodies

In another aspect, the invention provides antibodies to the polypeptides and polypeptide fragments of the invention, e.g., having an amino acid encoded by a nucleic acid comprising all or a portion of a nucleotide sequence selected from the group consisting of SEQ ID NOS: 1–33. Antibodies selectively bind to the protease and its variants and fragments. An antibody is considered to selectively bind, even if it also binds to other proteins that are not substantially homologous with the protease. These other proteins share homology with a fragment or domain of the protease. This conservation in specific regions gives rise to antibodies that bind to both proteins by virtue of the homologous sequence. In this case, it would be understood that antibody binding to the protease is still selective.

To generate antibodies, an isolated protease polypeptide is used as an immunogen to generate antibodies using standard techniques for polyclonal and monoclonal antibody preparation. Either the full-length protein or an antigenic peptide fragment can be used.

Antibodies are preferably prepared from these regions or from discrete fragments in antigenic regions. However, antibodies can be prepared from any region of the peptide as described herein. A preferred fragment produces an antibody that diminishes or completely prevents substrate or activator-binding. Antibodies can be developed against the entire protease or portions of the protease, for example, specific segments or any portions thereof. Antibodies may also be developed against specific functional sites, such as the site of substrate or activator-binding, or sites that are phosphorylated, glycosylated, myristoylated, or otherwise modified, such as amidated.

An antigenic fragment will typically comprise at least 10 contiguous amino acid residues. The antigenic peptide can comprise, however, at least 12, at least 14 amino acid residues, at least 15 amino acid residues, at least 20 amino acid residues, or at least 30 amino acid residues. In one embodiment, fragments correspond to regions that are located on the surface of the protein, e.g., hydrophilic regions. These fragments are not to be construed, however, as encompassing any fragments which may be disclosed prior to the invention.

Antibodies can be polyclonal or monoclonal. An intact antibody, or a fragment thereof (e.g. Fab or F(ab')$_2$) can be used.

Any of the many well known protocols used for fusing lymphocytes and immortalized cell lines can be applied for the purpose of generating a monoclonal antibody to a polypeptide of the invention.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, protein or chemically synthesized peptides.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825, U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." This technology is described, for example, in Jespers et al. (1994, *Bio/technology* 12:899–903).

Antibody Uses

The antibodies can be used to isolate a protease by standard techniques, such as affinity chromatography or immunoprecipitation. The antibodies can facilitate the purification of the natural protease from cells and recombinantly produced protease expressed in host cells.

The antibodies are useful to detect the presence of a protease in cells or tissues to determine the pattern of expression of the protease among various tissues in an organism and over the course of normal development.

The antibodies can be used to detect a protease in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length protease can be used to identify protease turnover.

Further, the antibodies can be used to assess protease expression in disease states such as in active stages of the disease or in an individual with a predisposition toward disease related to protease function. When a disorder is caused by an inappropriate tissue distribution, developmental expression, or level of expression of the protease protein, the antibody can be prepared against the normal protease. If a disorder is characterized by a specific mutation in the protease, antibodies specific for this mutant protein can be used to assay for the presence of the specific mutant protease. However, intracellularly-made antibodies ("intrabodies") are also encompassed, which would recognize intracellular protease peptide regions.

The antibodies can also be used to assess normal and aberrant subcellular localization of cells in the various tissues in an organism. Antibodies can be developed against the whole protease or portions of the protease, such as those described herein.

The diagnostic uses can be applied, not only in genetic testing, but also in monitoring a treatment modality. Accordingly, where treatment is ultimately aimed at correcting protease expression level or the presence of aberrant proteases and aberrant tissue distribution or developmental expression, antibodies directed against the protease or relevant fragments can be used to monitor therapeutic efficacy.

Antibodies accordingly can be used diagnostically to monitor levels in tissue as part of a clinical testing procedure, e.g., to, for example, determine the efficacy of a given treatment regimen.

Additionally, antibodies are useful in pharmacogenomic analysis. Thus, antibodies prepared against polymorphic proteases can be used to identify individuals that require modified treatment modalities.

The antibodies are also useful as diagnostic tools as an immunological marker for aberrant protease analyzed by electrophoretic mobility, isoelectric point, tryptic peptide digest, and other physical assays known to those in the art.

The antibodies are also useful for tissue typing. Thus, where a specific protease has been correlated with expression in a specific tissue, antibodies that are specific for this protease can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting protease function, for example, blocking substrate or activator binding.

These uses can also be applied in a therapeutic context in which treatment involves inhibiting protease function. An antibody can be used, for example, to block activator or substrate binding. Antibodies can be prepared against specific fragments containing sites required for function or against intact protease associated with a cell.

The invention also encompasses kits for using antibodies to detect the presence of a protease in a biological sample. The kit can comprise antibodies such as a labeled or labelable antibody and a compound or agent for detecting protease in a biological sample; means for determining the amount of protease in the sample; and means for comparing the amount of protease in the sample with a standard. The compound or agent can be packaged in a suitable container. The kit can further comprise instructions for using the kit to detect protease.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention thus provides vectors containing the protease polynucleotides. Another aspect of the invention pertains to nucleic acid constructs containing a nucleic acid selected from the group consisting of SEQ ID NOS: 1–33 (or a portion thereof). The term "vector" refers to a vehicle, preferably a nucleic acid molecule, that can transport the protease polynucleotides. When the vector is a nucleic acid molecule, the protease polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the protease polynucleotides. Alternatively, the vector may integrate into the host cell genome and produce additional copies of the protease polynucleotides when the host cell replicates.

The invention provides vectors for the maintenance (cloning vectors) or vectors for expression (expression vectors) of the protease polynucleotides. The vectors can function in procaryotic or eukaryotic cells or in both (shuttle vectors).

Expression vectors contain cis-acting regulatory regions that are operably linked in the vector to the protease polynucleotides such that transcription of the polynucleotides is allowed in a host cell. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The polynucleotides can be introduced into the host cell with a separate polynucleotide capable of affecting transcription. Thus, the second polynucleotide may provide a trans-acting factor interacting with the cis-regulatory control region to allow transcription of the protease polynucleotides from the vector. Alternatively, a trans-acting factor may be supplied by the host cell. Finally, a trans-acting factor can be produced from the vector itself.

It is understood, however, that in some embodiments, transcription and/or translation of the protease polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989), and such regulatory sequences are described, for example, in Goeddel, *Gene Expression Technology: Methods in Enzymology* 185, Academic Press, San Diego, Calif. (1990).

A variety of expression vectors can be used to express a protease polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, adeno-associated virus, poxviruses, pseudorabies viruses, and retroviruses. Vectors may also be derived from combinations of these sources such as those derived from plasmid and bacteriophage genetic elements, e.g,. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The protease polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of protease polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 1 d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the polynucleotide of interest can be altered to provide preferential codon usage for a specific host cell, for example *E. coli*. (Wada et al., *Nucleic Acids Res.* 20:2111–2118 (1992)).

The protease polynucleotides can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The protease polynucleotides can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the polynucleotides described herein are expressed in mammalian cells using mammalian expression vectors. Examples of mammalian expression vectors include pCDM8 (Seed, B. *Nature* 329:840 (1987)) and pMT2PC (Kaufman et al., *EMBO J.* 6:187–195 (1987)). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

Suitable host cells are discussed further in Goeddel, supra. Alternatively, the recombinant expression vector can be transcribed and translated in vitro, for example using T7 promoter regulatory sequences and T7 polymerase.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The expression vectors listed herein are provided by way of example only of the well-known vectors available to those of ordinary skill in the art that would be useful to express the protease polynucleotides. The person of ordinary skill in the art would be aware of other vectors suitable for maintenance propagation or expression of the polynucleotides described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as plant, fungal, and insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the protease polynucleotides can be introduced either alone or with other polynucleotides that are not related to the protease polynucleotides such as those providing trans-acting factors for expression vectors. When more than one vector is introduced into a cell, the vectors can be introduced independently, co-introduced or joined to the protease polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the protease polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also under stood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

The host cells expressing the polypeptides described herein, and particularly recombinant host cells, have a variety of uses. First, the cells are useful for producing protease polypeptides that can be further purified to produce desired amounts of these. Thus, host cells containing expression vectors are useful for polypeptide production.

Host cells are also useful for conducting cell-based assays involving the protease or protease fragments. Thus, a recombinant host cell expressing a native protease is useful to assay for compounds that stimulate or inhibit protease function. This includes activator binding, gene expression at the level of transcription or translation, substrate interaction, and components of the pathway in which the protease is a member.

Host cells are also useful for identifying protease mutants in which these functions are affected. If the mutants naturally occur and give rise to a pathology, host cells containing the mutations are useful to assay compounds that have a desired effect on the mutant protease (for example, stimulating or inhibiting function) which may not be indicated by their effect on the native protease.

Recombinant host cells are also useful for expressing the chimeric polypeptides described herein to assess compounds that activate or suppress activation by means of a heterologous activator binding domain. Alternatively, a heterologous proteolytic region can be used to assess the effect of a desired proteolytic domain on any given host cell. In this embodiment, a proteolytic region (or parts thereof) compatible with the specific host cell is used to make the chimeric vector. Alternatively, a heterologous substrate binding domain can be introduced into the host cell.

Further, mutant proteases can be designed in which one or more of the various functions is engineered to be increased or decreased (e.g., activator binding or substrate binding) and used to augment or replace proteases in an individual. Thus, host cells can provide a therapeutic benefit by replacing an aberrant protease or providing an aberrant protease that provides a therapeutic result. In one embodiment, the cells provide proteases that are abnormally active.

In another embodiment, the cells provide proteases that are abnormally inactive. These proteases can compete with endogenous proteases in the individual.

In another embodiment, cells expressing proteases that cannot be activated, are introduced into an individual in order to compete with endogenous proteases for activator.

For example, in the case in which excessive activator is part of a treatment modality, it may be necessary to inactivate this activator at a specific point in treatment. Providing cells that compete for the activator, but which cannot be affected by protease activation would be beneficial.

Homologously recombinant host cells can also be produced that allow the in situ alteration of endogenous protease polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the protease polynucleotides or sequences proximal or distal to a protease gene are allowed to integrate into a host cell genome by homologous recombination where expression of the gene can be affected. In one embodiment, regulatory sequences are introduced that either increase or decrease expression of an endogenous sequence. Accordingly, a protease protein can be produced in a cell not normally producing it. Alternatively, increased expression of protease protein can be effected in a cell normally producing the protein at a specific level. Further, expression can be decreased or eliminated by introducing a specific regulatory sequence. The regulatory sequence can be heterologous to the protease protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant protease proteins. Such mutations could be introduced, for example, into the specific functional regions such as the substrate-binding site.

In one embodiment, the host cell can be a fertilized oocyte or embryonic stem cell that can be used to produce a transgenic animal containing the altered protease gene.

Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous protease gene is selected (see e.g., Li, E. et al., *Cell* 15 69:915 (1992)). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the 20 homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity.

Other examples of transgenic animals include non-human primates, sheep, dogs, cows, goats, chickens, and amphibians.

In one embodiment, a host cell is a fertilized oocyte or an embryonic stem cell into which protease polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding, protease activation, and the pathway events may not be evident from in vitro cell-free or cell-based assays. Accordingly, it is useful to provide non-human transgenic animals to assay in? vivo protease function, including substrate or activator interaction, the effect of specific mutant proteases on protease function and interaction with other components, and the effect of chimeric proteases. It is also possible to assess the effect of null mutations, that is mutations that substantially or completely eliminate one or more protease functions.

In general, methods for producing transgenic animals include introducing a nucleic acid sequence according to the present invention, the nucleic acid sequence capable of expressing the protease protein in a transgenic animal, into a cell in culture or in vivo. When introduced in vivo, the nucleic acid is introduced into an intact organism such that one or more cell types and, accordingly, one or more tissue types, express the nucleic acid encoding the protease. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The protease nucleic acid molecules, protein (particularly fragments that comprise an extracellular domain), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a protease or anti-protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al., PNAS 91:3054–3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art.

Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

As discussed above, the inventors identified human genes encoding members of protease families based on a specific consensus motif or protein domain that characterizes the family. A search (hunt) of the nucleic acid sequence database was performed using one or more HMM (Hidden Markov Model) motifs or a TRANS BLASTN set or both.

The database was derived from random cDNA sequencing or by contigging nucleic acid fragments in pre-existing databases.

Hunts Included:
  ace
  aspartyl
  astacin
  c15
  caax
  calpain
  caspase
  cathepsin
  gamma-glutamyl
  hemoglobinase
  insulinase
  lon
  m17
  m18
  MAP
  matrixin
  neprilysin
  pcnp
  peptidase-m20b
  picornain3c
  prolyloligo
  prox
  renaldipep
  reprolysin
  s2p
  sercarboxy
  subtilase
  t1a
  thimet
  trypsin
  uch1
  uch2
  zncarboxy
  znprotease

HUNT SUMMARIES

Hunt Summary: Ace (angiotensin-converting enzyme)
  Profiles/HMMs: 1
  TBLASTN: 2
- - -
HMM Probes for Angiotensin-converting Enzyme
  Name: Peptidase$_{13}$ M2
  Acc: PF01401
Description: Angiotensin-converting Enzyme
  Accession PF01401
= = =
  ID Peptidase_M2
  AC PF01401
  Angiotensin-converting enzyme
  AU Bateman A, Coates D
  AL Clustalw_manual
  SE Swiss-Prot
  GA −45–45
  TC −43.70–43.70
  NC −291.80–291.80
  BM hmmbuild HMM SEED
  BM hmmcalibrate—seed 0 HMM
  RN [1]
  RM 98292810
  RT Toward a role for angiotensin-converting enzyme in insects.
  RA Isaac R E, Schoofs L, Williams T A, Corvol P, Veelaert D,
  RA Sajid M, Coates D;
  RL Ann. NY Acad. Sci. (1998) 839:288–292.
  RN [2]
  RM 95405266
  RT Peptidyl dipeptidase A: angiotensin I-converting enzyme.
  RA Corvol P, Williams T A, Soubrier F;
  RL Methods Enzymol. (1995) 248:283–305.
  DC This is family M2 in the peptidase classification.
  DR MEROPS; M2;
  DC This Prosite motif covers only the active site.
  DR PROSITE; PDOC00129;
  CC Members of this family are dipeptidyl carboxydipeptidases
  CC (cleave carboxyl dipeptides) and most notably convert
  CC angiotensin I to angiotensin II.
  CC Many members of this family contain a tandem duplication CC of the 600 amino acid peptidase domain, both of these are
CC catalytically active. Most members are secreted membrane
CC bound ectoenzymes.
SQ 20
- - -
Accession PDOC00129
= = =
- - -
TBLASTN Probes for Angiotensin-converting Enzyme
DbAcc: SP:P22966
Species: *Homo sapiens*
Description: angiotensin-converting enzyme precursor, testis-specific (EC 3.4.15.1) (ACE-T) (dipeptidyl carboxypeptidase I) (kininase II).
DbAcc: SP:P12821
Species: *Homo sapiens*
Description: angiotensin-converting enzyme precursor, somatic (EC 3.4.15.1) (ACE) (dipeptidyl carboxypeptidase I) (kininase II).
- - -
Hunt Summary: Hemoglobinase
Profiles/HMMs: 0
TBLASTN: 2
- - -
HMM Probes for Hemoglobinase
None.
- - -
TBLASTN Probes for Hemoglobinase
DbAcc: GP:Y07596
Species: *Homo sapiens*
Description: GPI transamidase
bAcc: SP:Q99538
Species: *Homo sapiens*
Description: Legumain Precursor (EC 3.4.22.34) (asparaginyl endopeptidase).
- - -
Hunt Summary: Matrixin (matrix metalloproteases)
Profiles/HMMs 1
TBLASTN: 27
- - -
HMM Probes for Matrix Metalloproteases
Name: Peptidase_M10
Acc: PF00413
Description: Matrixin
Accession PF00413
= = =
ID Peptidase_M10
AC PF00413
Matrixin
PI matrixin;
AU Bateman A, Finn R D
AL Clustalw
SE Prosite
GA -50-50
TC -49.10-49.10
NC -55.50-55.50
BM hmmbuild HMM SEED
BM hmmcalibrate—seed 0 HMM
RN [1]
RM 95405261
RT Evolutionary families of metallopeptidases.
RA Rawlings N D, Barrett A J;
RL *Meth. Enzymol.* (1995) 248:183–228.
RN [2]
RM 95384761
RT The NMR structure of the inhibited catalytic domain of
RT human stromelysin-1.
RA Gooley P R, O'Connell J F, Marcy A I, Cuca G C, Salowe S P, Bush
RA B L, Hermes J D, Esser C K, Hagmann W K, Springer J P, et al;
RL *Nat. Struct. Biol.* (1994) 1:111–118.
DC This is family M10 in the peptidase classification.
DR MEROPS; M10;
DC This Prosite motif covers only the active site.
DR PROSITE; PDOC00472;
DR PRINTS, PR00138;
DR SCOP; 2srt; fa;
DC The following Pfam-B families contain sequences that according to Prodom
DC are members of this Pfam-A family.
DR PFAMB, PB035983;
DR PFAMB; PB036528;
CC The members of this family are enzymes that cleave peptides.
CC These proteases require zinc for catalysis.
SQ 99
- - -
Accession PDOC00472
= = =
- - -
TBLASTN Probes for Matrix Metalloproteases
DbAcc: SP:P03956
Species: *Homo sapiens*
Description: interstitial collagenase precursor (EC 3.4.24.7) (matrix metalloproteinase-1) (MMP-1) (fibroblast collagenase).
DbAcc: SP:P08253
Species: *Homo sapiens*
Description: 72 KD type IV collagenase precursor (EC 3.4.24.24) (72 KD gelatinase) (matrix metalloproteinase-2) (MMP-2) (gelatinase A) (TBE-1).
DbAcc: SP:P08254
Species: *Homo sapiens*
Description: stromelysin-1 precursor (EC 3.4.24.17) (matrix metalloproteinase-3) (MMP-3) (TRANSIN-1) (SL-1).
DbAcc: SP:P22894
Species: *Homo sapiens*
Description: neutrophil collagenase precursor (EC 3.4.24.34) (matrix metalloproteinase-8) (MMP-8) (PMNL collagenase) (PMNL-CL).
DbAcc: SP:P14780
Species: *Homo sapiens*
Description: 92 KD type IV collagenase precursor (EC 3.4.24.35) (92 KD gelatinase) (matrix metalloproteinase-9) (MMP-9) (gelatinase B).

DbAcc: SP:P39900
  Species: *Homo sapiens*
Description: macrophage metalloelastase precursor (EC 3.4.24.65) (HME) (matrix metalloproteinase-12) (MMP-12).
DbAcc: SP:P50281
  Species: *Homo sapiens*
Description: matrix metalloproteinase-14 precursor (EC 3.4.24.-) (MMP-14) (membrane-type matrix metalloproteinase 1) (MT-MMP 1) (MTMMP1).
DbAcc: SP:P51511
  Species: *Homo sapiens*
Description: matrix metalloproteinase-15 precursor (EC 3.4.24.-) (MMP-15) (membrane-type matrix metalloproteinase 2) (MT-MMP 2) (MTMMP 2).
DbAcc: SP:P51512
  Species: *Homo sapiens*
Description: matrix metalloproteinase-16 precursor (EC 3.4.24.-) (MMP-16) (membrane-type matrix metalloproteinase 3) (MT-MMP 3) (MTMMP3) (MMP-X2).
DbAcc: SP:P09238
  Species: *Homo sapiens*
Description: stromelysin-2 precursor (EC 3.4.24.22) (matrix metalloproteinase-10) (MMP-10) (TRANSIN-2) (SL-2).
DbAcc: SP:P24347
  Species: *Homo sapiens*
Description: stromelysin-3 precursor (EC 3.4.24.-) (matrix metalloproteinase-11) (MMP-11) (ST3) (SL-3).
DbAcc: SP:P45452
  Species: *Homo sapiens*
Description: collagenase 3 precursor (EC 3.4.24.-) (matrix metalloproteinase-13) (MMP-13).
DbAcc: SP:P09237
  Species: *Homo sapiens*
Description: matrilysin precursor (EC 3.4.24.23) (PUMP-1 protease) (uterine metalloproteinase) (matrix metalloproteinase-7) (MMP-7) (MATRIN).
DbAcc: GP:X92521
  Species: *Homo sapiens*
Description: 1731986 MMP-19 (matrix metalloproteinase)
DbAcc: GP:X89576
  Species: *Homo sapiens*
Description: 1490312 MT4-MMP
DbAcc: GP:AB010960
  Species: *Rattus rattus*
Description: 2879941 MIFR
DbAcc: GP:AJ003144
  Species: *Homo sapiens*
Description: 2808655 MMP20
DbAcc: GP:AB007815
  Species: *Caenorhabditis elegans*
Description: 3152402 matrix metalloproteinase
DbAcc: GP:AB007817
  Species: *Caenorhabditis elegans*
Description: 3152406 matrix metalloproteinase
DbAcc: GP:Z95309
  Species: *Caenorhabditis elegans*
Description: 3878095 H36L18.1 Similarity to human matrix metalloprotease I (MMP1)
DbAcc: GP:AF040648
  Species: *Caenorhabditis elegans*
Description: H19M22.3 contains similarity to the M10B peptidase family
DbAcc: GP:U00038
  Species: *Caenorhabditis elegans*
Description: T21D11.1 similar to hatching enzyme precursor and other zinc metalloproteinases
DbAcc: GP:AF003534
  Species: *Chilo iridescent virus*
Description: putative metallopeptidase
DbAcc: GP:AC002396
  Species: *Arabidopsis thaliana*
Description: F3I6.6 similar to zinc metalloproteinases
DbAcc: GP:AF063866
  Species: *Melanoplus sanguinipes entomopoxvirus*
Description: MSV179
DbAcc: SP:P16317
  Species: *Erwinia chrysanthemi*
Description: secreted protease C precursor (EC 3.4.24.-) (PROC).
DbAcc: GP:Z78414
  Species: *Caenorhabditis elegans*
Description: 1350129 W09D12.1 predicted using Genefinder

- - -

Hunt Summary: pcnp (procollagen N-proteinase)
Profiles/HMMs: 0
TBLASTN: 1

- - -

HMM Probes for procollagen N-proteinase
None.

- - -

TBLASTN Probes for Procollagen N-proteinase
  DbAcc: GP:AJ003125
    Species: *Homo sapiens*
  Description: 3928000 hPCPNI

- - -

Hunt Summary: Reprolysin (ADAM family of metalloprotease)
Profiles/HMMs: 1
TBLASTN: 24

- - -

HMM Probes for ADAM Family of Metalloprotease
  Name: Reprolysin
  Acc: PF01421
  Description: Reprolysin (M12B) family zinc metalloprotease
  Accession PF01421
  = = =
  ID Reprolysin
  AC PF01421
Reprolysin (M12B) Family Zinc Metalloprotease
  AU Bateman A
  AL Clustalw
  SE Swissprot
  GA -100-100
  TC -96.50 -96.50
  NC -111.80-111.80
  BM hmmbuild HMM SEED BM hmmcalibrate—seed 0 HMM
RN [1]
RM 95405261
RT Evolutionary families of metallopeptidases.
RA Rawlings N D, Barrett A J;
RL *Meth. Enzymol.* (1995)248:183–228.
DC This Prosite motif covers only the active site.
DR PROSITE; PDOC00129;
DR SCOP; last; fa;
DC This is family M12B in the peptidase classification.
DR MEROPS; M12;
DC The following Pfam-B families contain sequences that according to Prodom
DC are members of this Pfam-A family.
DR PFAMB; PB016125;
DR PFAMB; PB031186;
DR PFAMB; PB035940;
DR PFAMB, PB036263;
CC The members of this family are enzymes that cleave peptides.
CC These proteases require zinc for catalysis. Members of this
CC family are also known as adamalysins.
CC Most members of this family are snake venom endopeptidases,
CC but there are also some mammalian proteins such as Swiss:P78325,
CC and fertilin Swiss:Q28472. Fertilin and closely related
CC proteins appear to not have some active site residues and
CC may not be active enzymes.
SQ 115
- - -
Accession PDOC00129
= = =
- - -
TBLASTN Probes for ADAM Family of Metalloprotease
  DbAcc: SP:QD5910
    Species: *Mus musculus*
  Description: cell surface antigen MS2 precursor (EC 3.4.24.-) (macrophage cysteine-rich glycoprotein).
  DbAcc: GP:U41767
    Species: *Homo sapiens*
  Description: metargidin precursor
  DbAcc: GP:AF009615
    Species: *Homo sapiens*
  Description: disintegrin-metalloprotease MADM
  DbAcc: GP:AJ242015
    Species: *Homo sapiens*
  Description: 4757044 eMDC II protein
  DbAcc: GP:D31872
    Species: *Homo sapiens*
  Description: 836684 metalloprotease/disintegrin-like protein
  DbAcc: GP:D67076
    Species: *Mus musculus*
  Description: 1813340 secretory protein containing thrombospondin
  DbAcc: SP:P78325
    Species: *Homo sapiens*
  Description: cell surface antigen MS2 precursor (EC 3.4.24.-) (CD156 antigen).
  DbAcc: GP:AF019887
    Species: *Mus musculus*
  Description: metalloprotease-disintegrin meltrin beta
  DbAcc: GP:U22058
    Species: *Mus musculus*
  Description: ADAM 4 protein precursor
  DbAcc: GP:AF029899
    Species: *Homo sapiens*
  Description: ADAM 20
  DbAcc: GP:AF006196
    Species: *Mus musculus*
  Description: metalloprotease-disintegrin MDC15
  DbAcc: GP:AJ012603
    Species: *Rattus rattus*
  Description: 1340857 TNF-alpha converting enzyme (TACE)
  DbAcc: GP:AB009672
    Species: *Homo sapiens*
  Description: 3419878 MDC3
  DbAcc: GP:X77619
    Species: *Macaca macaca*
  Description: tMDC II
  DbAcc: GP:Y13323
    Species: *Homo sapiens*
  Description: 2370107 disintegrin-protease
  DbAcc: GP:U68185
    Species: *Caenorhabditis elegans*
  Description: adm-1 domain organization is identical to PH-30/fertilin
  DbAcc: GP:U42846
    Species: *Caenorhabditis elegans*
  Description: T19D2.1 coded for by *C. elegans* cDNA yk126d9.3
  DbAcc: GP:Z81460
    Species: *Caenorhabditis elegans*
  Description: 3873969 C04A11.4 Similarity to mouse meltrin alpha protein
  DbAcc: SP:013766
    Species: *Schizosaccharomyces pombe*
  Description: probable zinc metallopeptidase C17A5.04C precursor (EC 3.4.24.-).
  DbAcc: GP:Y10615
    Species: *Homo sapiens*
  Description: 2198473 CYRN2 member of ADAM family
  DbAcc: GP:AJ010688
    Species: *Mus musculus*
  Description: 1320044 CYRN1
  DbAcc: GP:AF032383
    Species: *Xenopus laevis*
  Description: MDC 11 b
  DbAcc: GP:U78185
    Species: *Xenopus laevis*
  Description: xMDC 16
  DbAcc: SP:P30403
    Species: *Agkistrodon rhodostoma*
  Description: hemorrhagic protein-rhodostomin precursor (EC 3.4.24.-) (RHO) [contains: disintegrin rhodostomin].

---
Hunt Summary: Sercarboxy (serine carboxypeptidases)
  Profiles/HMMs: 1
  TBLASTN: 9
---
HMM Probes for Serine Carboxypeptidases
  Name: serine_carbpept
  Acc: PF00450
  Description: Serine Carboxypeptidase
  Accession PF00450
  = = =
  ID serine_carbpept
  AC PF00450
  Serine carboxypeptidase
  AU Finn RD
  AL Clustalw
  SE Prosite
  GA 25 0
  TC 69.10 4.50
  NC 6.10 6.10
  BM hmmbuild –f HMM SEED
  BM hmmcalibrate—seed 0HMM
  DR PROSITE; PDOC00122;
  DR PRINTS; PR00724;
  DR SCOP; 1whs; fa;
  SQ 89
  ---
  Accession PDOC00122
  = = =
  ---
TBLASTN Probes for Serine Carboxypeptidases
  DbAcc: SP:P10619
    Species: Homo sapiens
    Description: lysosomal protective protein precursor (EC 3.4.16.5) (cathepsin A) (carboxypeptidase C).
  DbAcc: SP:P09620
    Species: Saccharomyces cerevisiae
    Description: carboxypeptidase KEX1 precursor (EC 3.4.16.6) (carboxypeptidase D).
  DbAcc: SP:P38109
    Species: Saccharomyces cerevisiae
    Description: putative serine carboxypeptidase in ESR1-IRA1 intergenic region (EC 3.4.16.-).
  DbAcc: SP:P52714
    Species: Caenorhabditis elegans
    Description: putative serine carboxypeptidase C08H9.1 (EC 3.4.16.-).
  DbAcc: SP:P52715
    Species: Caenorhabditis elegans
    Description: putative serine carboxypeptidase F13S12.6 precursor (EC 3.4.16.-).
  DbAcc: SP:P52717
    Species: Caenorhabditis elegans
    Description: putative serine carboxypeptidase F41C3.5 precursor (EC 3.4.16.-).
  DbAcc: SP:Q09991
    Species: Caenorhabditis elegans
    Description: putative serine carboxypeptidase K10B2.2 precursor (EC 3.4.16.-).
  DbAcc: GP:AC005162
    Species: Homo sapiens
    Description: probable carboxypeptidase precursor
  DbAcc: GP:AC006929
    Species: Arabidopsis thaliana
    Description: T1E2.16
---
Hunt Summary: t1a (t1a (proteasome-a) proteases)
  Profiles/HMMs: 1
  TBLASTN: 23
---
HMM Probes for t1a (proteasome-a) proteases
  Name: proteasome
  Acc: PF00227
  Description: Proteasome A-type and B-type
  Accession PF00227
  = = =
  ID proteasome
  AC PF00227
  Proteasome A-type and B-type
  AU Finn RD
  AL Clustalw
  SE Prosite
  GA 9.6 9.6
  TC 13.40 13.40
  NC 8.10 8.10
  BM hmmbuild '-f HMM SEED
  BM hmmcalibrate—seed 0 HMM
  DR SCOP; 1pma; fa;
  DR PROSITE; PDOC00326;
  DR PROSITE; PDOC00668;
  DR PRINTS; PR00141;
  DC The following Pfam-B families contain sequences that according to Prodom
  DC are members of this Pfam-A family.
  DR PFAMB; PB005708;
  DR PFAMB; PB035721;
  SQ 206
  ---
  Accession PDOC00326
  = = =
  ---
  Accession PDOC00668
  = = =
  ---
TBLASTN Probes for t1a (proteasome-a) proteases
  DbAcc: SP:P49720
    Species: Homo sapiens
    Description: proteasome theta chain (EC 3.4.99.46) (macropain theta chain) (multicatalytic endopeptidase complex theta chain) (proteasome chain 13) (proteasome component C10-II).
  DbAcc: SP:P18421
    Species: Rattus rattus
    Description: proteasome component C5 (EC 3.4.99.46) (macropain subunit C5) (proteasome gamma chain) (multicatalytic endopeptidase complex subunit C5).
  DbAcc: SP:P18420
    Species: Rattus rattus Description: proteasome component C2 (EC 3.4.99.46) (macropain subunit C2) (proteasome nu chain) (multicatalytic endopeptidase complex subunit C2).
DbAcc: SP:P48004
  Species: *Rattus rattus*
Description: proteasome subunit RC6-1 (EC 3.4.99.46) (multicatalytic endopeptidase complex subunit RC6-1).
DbAcc: SP:P28062
  Species: *Homo sapiens*
Description: proteasome component C13 precursor (EC 3.4.99.46) (macropain subunit C13) (multicatalytic endopeptidase complex subunit C13).
DbAcc: SP:P25789
  Species: *Homo sapiens*
Description: proteasome component C9 (EC 3.4.99.46) (macropain subunit C9) (multicatalytic endopeptidase complex subunit C9).
DbAcc: SP:P49721
  Species: *Homo sapiens*
Description: proteasome component C7-I(EC 3.4.99.46) (macropain subunit C7-I) (multicatalytic endopeptidase complex subunit C7-I).
DbAcc: SP:P28070
  Species: *Homo sapiens*
Description: proteasome beta chain precursor (EC 3.4.99.46) (macropain beta chain) (multicatalytic endopeptidase complex beta chain) (proteasome chain 3) (HSN3) (HSBPROS26).
DbAcc: SP:P34062
  Species: *Rattus rattus*
Description: proteasome iota chain (EC 3.4.99.46) (macropain iota chain) (multicatalytic endopeptidase complex iota chain) (27 KD prosomal protein) (PROS-27) (P27K).
DbAcc: SP:P28066
  Species: *Homo sapiens*
Description: proteasome zeta chain (EC 3.4.99.46) (macropain zeta chain) (multicatalytic endopeptidase complex zeta chain).
DbAcc: SP:P49722
  Species: *Mus musculus*
Description: proteasome component C3 (EC 3.4.99.46) (macropain subunit C3) (multicatalytic endopeptidase complex subunit C3).
DbAcc: SP:P22141
  Species: *Saccharomyces cerevisiae*
Description: proteasome component C11 (EC 3.4.99.46) (macropain subunit C11) (proteinase ysce subunit 11) (multicatalytic endopeptidase complex subunit C11).
DbAcc: SP:O23715
  Species: *Arabidopsis thaliana*
Description: proteasome component C8 (EC 3.4.99.46) (macropain subunit C8) (multicatalytic endopeptidase complex subunit C8).
DbAcc: SP:P23724
  Species: *Saccharomyces cerevisiae*
Description: potential proteasome component C5 (EC 3.4.99.46) (multicatalytic endopeptidase complex subunit C5).
DbAcc: SP:P25043
  Species: *Saccharomyces cerevisiae*
Description: proteasome component PUP1 precursor (EC 3.4.99.46) (macropain subunit PUP1) (proteinase YSCE subunit PUP1) (multicatalytic endopeptidase complex subunit PUP1).
DbAcc: SP:P28077
  Species: *Rattus rattus*
Description: proteasome chain 7 precursor (EC 3.4.99.46) (macropain chain 7) (multicatalytic endopeptidase complex chain 7) (ring 12 protein).
DbAcc: SP:Q58634
  Species: *Methanococcus jannaschii*
Description: proteasome, beta subunit (EC 3.4.99.46) (multicatalytic endopeptidase complex beta subunit).
DbAcc: GP:Y13175
  Species: *Arabidopsis thaliana*
Description: 2511572 prcga yeast counterpart beta4_Sc
DbAcc: SP:P30657
  Species: *Saccharomyces cerevisiae*
Description: proteasome component pre4 (EC 3.4.99.46) (macropain subunit PRE4) (proteinase YSCE subunit PRE4) (multicatalytic endopeptidase complex subunit PRE4).
DbAcc: SP:P38624
  Species: *Saccharomyces cerevisiae*
Description: proteasome component PRE3 precursor (EC 3.4.99.46) (macropain subunit PRE3) (proteinase YSCE subunit PRE3) (multicatalytic endopeptidase complex subunit PRE3).
DbAcc: SP:Q09720
  Species: *Schizosaccharomyces pombe*
Description: putative proteasome component C7-I/C11 (EC 3.4.99.46) (macropain subunit) (multicatalytic endopeptidase complex subunit).
DbAcc: SP:P31059
  Species: *Escherichia coli*
Description: heat shock protein HSLV (EC 3.4.99.-).
DbAcc: GP:U80442
  Species: *Caenorhabditis elegans*
Description: T20F5.2 coded for by *C. elegans* cDNA CEESC71F.

- - -

Hunt Summary: Trypsin (trypsin-like serine proteases)
  Profiles/HMMs: 1
  TBLASTN: 69

- - -

HMM Probes for Trypsin-like Serine Proteases
  Name: trypsin
  Acc: PF00089
  Description: Trypsin
  Accession PF00089
  = = =
  ID trypsin
  AC PF00089
  Trypsin
  AU Lutfiyya L L, Sonnhammer E L L
  AL Clustalw
  SE SCOP and Prosite
  GA -35 -35
  TC -34.20 -34.20
  NC -35.60 -35.60
  BM hmmbuild HMM SEED
  BM hmmcalibrate—seed0 HMM RN [1]
RM 95147689
RT Families of Serine Peptidases
RA Rawlings N D, Barrett A J;
RL *Meth. Enzymol.* (1994) 244:19–61.
RN [2]
RM 87292123
RT The Three Dimensional Structure of Asn102 Trypsin: Role of
RT Asp102 in Serine Protease Catalysis
RA Sprang S, Standing T, Fletterick R J, Stroud R M, Finer-Moore
RA J, Xuong N H, Hamlin R, Rutter W J, Craik C S;
RL *Science* (1987) 237:905–909.
DR PROSITE; PDOC00124;
DR SCOP; 1mct; fa;
DC The following Pfam-B families contain sequences that according to Prodom
DC are members of this Pfam-A family.
DR PFAMB; PB001787;
DR PFAMB; PB001799;
DR PFAMB; PB031543;
DR PFAMB; PB036276;
DR PFAMB; PB036371;
DR PFAMB; PB036499;
DR PFAMB; PB036558;
CC Proteins recognized include all proteins in families S1, S2A, S2B,
CC S2C, and S5 in the classification of peptidases.
CC Also included are proteins that are clearly members, but that lack
CC peptidase activity, such as haptoglobin and protein Z (PRTZ*).
SQ 696
- - -
Accession PDOC00124
= = =
- - -
TBLASTN Probes for Trypsin-like Serine Proteases
  DbAcc: SP:P09871
    Species: *Homo sapiens*
  Description: complement C1S component precursor (EC 3.4.21.42) (C1 esterase).
  DbAcc: SP:P00742
    Species: *Homo sapiens*
  Description: coagulation factor X precursor (EC 3.4.21.6) (Stuart factor).
  DbAcc: SP:P00748
    Species: *Homo sapiens*
  Description: coagulation factor XII precursor (EC 3.4.21.38) (Hageman factor) (HAF).
  DbAcc: SP:P08709
    Species: *Homo sapiens*
  Description: coagulation factor VII precursor (EC 3.4.21.21).
  DbAcc: SP:P33587
    Species: *Mus musculus*
  Description: vitamin-K dependent protein C precursor (EC 3.4.21.69) (autoprothrombin IIA) (anticoagulant protein C).
  DbAcc: SP:P22891
    Species: *Homo sapiens*
  Description: vitamin K-dependent protein Z precursor.
  DbAcc: SP:P10323
    Species: *Homo sapiens*
  Description: acrosin precursor (EC 3.4.21.10).
  DbAcc: SP:P00736
    Species: *Homo sapiens*
  Description: complement C1R component precursor (EC 3.4.21.41).
  DbAcc: SP:P20160
    Species: *Homo sapiens*
  Description: azurocidin precursor (cationic antimicrobial protein CAP37) (heparin-binding protein) (HBP).
  DbAcc: SP:P08311
    Species: *Homo sapiens*
  Description: cathepsin G precursor (EC 3.4.21.20).
  DbAcc: SP:P00751
    Species: *Homo sapiens*
  Description: complement factor B precursor (EC 3.4.21.47) (C3/C5 convertase) (properdin factor B) (glycine-rich beta glycoprotein) (GBG) (PBF2).
  DbAcc: SP:P05156
    Species: *Homo sapiens*
  Description: complement factor I precursor (EC 3.4.21.45) (C3B/C4B inactivator).
  DbAcc: SP:P06681
    Species: *Homo sapiens*
  Description: complement C2 precursor (EC 3.4.21.43) (C3/C5 convertase).
  DbAcc: SP:P48740
    Species: *Homo sapiens*
  Description: complement-activating component of RA-reactive factor precursor (EC 3.4.21.-) (RA-reactive factor serine protease P100) (RARF) (mannose-binding protein associated serine protease) (MASP).
  DbAcc: SP:P17538
    Species: *Homo sapiens*
  Description: chymotrypsinogen B precursor (EC 3.4.21.1).
  DbAcc: SP:P13582
    Species: *Drosophila melanogaster*
  Description: serine protease easter precursor (EC 3.4.21.-).
  DbAcc: SP:P08217
    Species: *Homo sapiens*
  Description: elastase 2A precursor (EC 3.4.21.71).
  DbAcc: SP:P08861
    Species: *Homo sapiens*
  Description: elastase IIIB precursor (EC 3.4.21.70) (protease E).
  DbAcc: SP:P12544
    Species: *Homo sapiens*
  Description: granzyme a precursor (EC 3.4.21.78) (cytotoxic T-lymphocyte proteinase 1) (hanukkah factor) (H factor) (HF) (granzyme 1) (CTL tryptase) (fragmentin 1).
  DbAcc: SP:P08883
    Species: *Mus musculus*
  Description: granzyme F precursor (EC 3.4.21.-) (cytotoxic cell protease 4) (CCP4) (CTL serine protease 3) (C134) (cytotoxic serine protease 3) (MCSP3).

DbAcc: SP:P51124
Species: *Homo sapiens*
Description: granzyme M precursor (EC 3.4.21.-) (MET-ASE) (natural killer cell granular protease) (HU-MET-1) (MET-1 serine protease).
DbAcc: SP:P05981
Species: *Homo sapiens*
Description: serine protease hepsin (EC 3.4.21.-).
DbAcc: SP:P26927
Species: *Homo sapiens*
Description: hepatocyte growth factor-like protein precursor (macrophage stimulatory protein) (MSP) (macrophage stimulating protein).
DbAcc: SP:P00737
Species: *Homo sapiens*
Description: haptoglobin-1 precursor.
DbAcc: SP:P26262
Species: *Mus musculus*
Description: plasma kallikrein precursor (EC 3.4.21.34) (plasma prekallikrein) (kininogenin) (Fletcher factor).
DbAcc: SP:P15948
Species: *Mus musculus*
Description: glandular kallikrein K22 precursor (EC 3.4.21.35) (tissue kallikrein) (MGK-22) (epidermal growth factor-binding protein type A) (EGF-BP A) (nerve growth factor beta chain endopeptidase) (beta-NGF- endopeptidase).
DbAcc: SP:P21845
Species: *Mus musculus*
Description: mast cell protease 6 precursor (EC 3.4.21.-) (MMCP-6) (tryptase).
DbAcc: SP:P98159
Species: *Drosophila melanogaster*
Description: serine protease nudel precursor (EC 3.4.21.-).
DbAcc: SP:P00747
Species: *Homo sapiens*
Description: plasminogen precursor (EC 3.4.21.7).
DbAcc: SP:P24158
Species: *Homo sapiens*
Description: myeloblastin precursor (EC 3.4.21.76) (leukocyte proteinase 3) (PR-3) (PR3) (AGP7) (Wegener's autoantigen) (P29) (C-ANCA antigen).
DbAcc: SP:P49862
Species: *Homo sapiens*
Description: stratum corneum chymotryptic enzyme precursoR (EC 3.4.21.-) (SCCE).
DbAcc: SP:P17205
Species: *Drosophila melanogaster*
Description: serine proteases 1 and 2 precursor (EC 3.4.21.-).
DbAcc: SP:P05049
Species: *Drosophila melanogaster*
Description: serine protease snake precursor (EC 3.4.21.-).
DbAcc: SP:Q05319
Species: *Drosophila melanogaster*
Description: serine proteinase stubble (EC 3.4.21.-) (stubble-stubbloid protein).
DbAcc: SP:P00734
Species: *Homo sapiens*
Description: prothrombin precursor (EC 3.4.21.5) (coagulation factor II).
DbAcc: SP:P07477
Species: *Homo sapiens*
Description: trypsinogen 1 precursor (EC 3.4.21.4).
DbAcc: SP:P35005
Species: *Drosophila melanogaster*
Description: trypsin epsilon precursor (EC 3.4.21.4).
DbAcc: SP:P52905
Species: *Drosophila melanogaster*
Description: trypsin iota precursor (EC 3.4.21.4).
DbAcc: SP:P42278
Species: *Drosophila melanogaster*
Description: trypsin theta precursor (EC 3.4.21.4).
DbAcc: SP:P42279
Species: *Drosophila melanogaster*
Description: trypsin eta precursor (EC 3.4.21.4).
DbAcc: SP:P42279
Species: *Drosophila melanogaster*
Description: trypsin eta precursor (EC 3.4.21.4).
DbAcc: SP:P15120
Species: *Gallus gallus*
Description: urokinase-type plasminogen activator precursor (EC 3.4.21.73) (UPA) (U-plasminogen activator).
DbAcc: GP:D49742
Species: *Homo sapiens*
Description: HGF activator like protein
DbAcc: GP:S82666
Species: *Homo sapiens*
Description: Description: normal epithelial cell specific gene
DbAcc: SP:Q16651
Species: *Homo sapiens*
Description: prostasin
DbAcc: GP:U47810
Species: *Mus musculus*
Description: complement factor I
DbAcc: GP:Y09926
Species: *Homo sapiens*
Description: MASP-2 protein
DbAcc: GP:Y13192
Species: *Mus musculus*
Description: neurotrypsin
DbAcc: GP:AE000663
Species: *Mus musculus*
Description: trypsinogen 1
DbAcc: SP:P17945
Species: *Rattus rattus*
Description: hepatocyte growth factor precursor (scatter factor) (SF) (hepatopoeitin A).
DbAcc: SP:P19637
Species: *Rattus rattus*
Description: tissue plasminogen activator precursor (EC 3.4.21.68) (TPA) (T-plasminogen activator).
DbAcc: SP:P97435
Species: *Mus musculus*
Description: enteropeptidase (EC 3.4.21.9) (enterokinase).
DbAcc: SP:P49864
Species: *Rattus rattus*
Description: granzyme K precursor (EC 3.4.21.-) (NK-tryptase-2) (NK-TRYP-2).

DbAcc: GP:AF042822
  Species: *Mus musculus*
Description: epithin
DbAcc: GP:AF042822
  Species: *Mus musculus*
Description: epithin
DbAcc: SP:P27435
  Species: *Rattus rattus*
Description: mast cell protease 7 precursor (EC 3.4.21.-) (RMCP-7) (tryptase, skin).
DbAcc: SP:P32038
  Species: *Rattus rattus*
Description: complement factor D precursor (EC 3.4.21.46) (C3 convertase activator) (properdin factor D) (adipsin) (endogenous vascular elastase).
DbAcc: GP:AB002134
  Species: *Homo sapiens*
Description: 3184184 airway trypsin-like protease
DbAcc: GP:AC003965
  Species: *Homo sapiens*
Description: SP001LA
DbAcc: GP:U76256
  Species: *Sus scrofa*
Description: enamel matrix serine proteinase 1 precursor
DbAcc: GP:X75363
  Species: *Homo sapiens*
Description: serine protease homologue
DbAcc: SP:P39790
  Species: *Bacillus subtilis*
Description: extracellular metalloprotease precursor (EC 3.4.21.-).
DbAcc: GP:AF056311
  Species: *Drosophila melanogaster*
Description: gd
DbAcc: GP:U29380
  Species: *Caenorhabditis elegans*
Description: ZK546.15 similar to plasminogen and to trypsin-like serine
DbAcc: GP:AL031025
  Species: *Drosophila melanogaster*
Description: 1313456 EG:9D2.4 1
DbAcc: GP:U31961
  Species: *Drosophila melanogaster*
Description: serine protease-like protein
DbAcc: GP:U70848
  Species: *Caenorhabditis elegans*
Description: C43G2.5 similar to peptidase family S1
DbAcc: GP:AB026735
  Species: *Bombyx mori*
Description: 4760786 30kP protease A (43k peptide) precursor
DbAcc: SP:P04188
  Species: *Staphylococcus aureus*
Description: glutamyl endopeptidase precursor (EC 3.4.21.19) (staphylococcal serine proteinase) (V8 proteinase) (endoproteinase GLU-C).
- - -
Hunt Summary: uch2 (Ubiquitin carboxyl-terminal hydrolases family 2)
  ProfilesHMMs: 2
  TBLASTN: 33

- - -
HMM Probes for Ubiquitin Carboxyl-terminal Hydrolases Family 2
  Name: UCH-1
  Acc: PF00442
  Description: Ubiquitin Carboxyl-terminal Hydrolases Family 2
  Accession PF00442
= = =
ID UCH-1
AC PF00442
Ubiquitin Carboxyl-terminal Hydrolases Family 2
AU Finn R D
AL Clustalw
SE Prosite
GA 15 15
TC 17.30 17.30
NC 14.80 14.80
BM hmmbuild HMM SEED
BM hmmcalibrate—seed0 HMM
DR PROSITE; PDOC00750;
DC The following Pfam-B family may contain sequences that according to Prodom
DC are members of this Pfam-A family.
DR PFAMB; PB000592;
SQ 81
- - -
Accession PDOC00750
= = =
  Name: UCH-2
  Acc: PF00443
  Description: Ubiquitin Carboxyl-terminal Hydrolases Family 2
  Accession PF00443
= = =
ID UCH-2
AC PF00443
Ubiquitin carboxyl-terminal hydrolases family 2
AU Finn R D
AL Clustalw
SE Prosite
GA 25 25
TC 27.10 27.10
NC 21.80 24.00
BM hmmbuild –f HMM SEED
BM hmmcalibrate—seed0 HMM
DR PROSITE, PDOC00750;
SQ 78
- - -
Accession PDOC00750
= = =
- - -
TBLASTN Probes for Ubiquitin Carboxyl-terminal Hydrolases Family 2
  DbAcc: SP:P40818
    Species: *Homo sapiens*
  Description: probable ubiquitin carboxyl-terminal hydrolase (EC 3.1.2.15) (ubiquitin thiolesterase) (ubiquitin-specific processing protease) (deubiquitinating enzyme) (KIAA0055).

DbAcc: SP:P56399
Species: *Mus musculus*
Description: ubiquitin carboxyl-terminal hydrolase T (EC 3.1.2.15) (ubiquitin thiolesterase T) (ubiquitin-specific processing protease T) (deubiquitinating enzyme T) (isopeptidase T).

DbAcc: SP:P54578
Species: *Homo sapiens*
Description: queuine trna-ribosyltransferase (EC 2.4.2.29) (TRNA-guanine transglycosylase) (guanine insertion enzyme).

DbAcc: SP:Q93008
Species: *Homo sapiens*
Description: probable ubiquitin carboxyl-terminal hydrolase FAF-X (EC 3.1.2.15) (ubiquitin thiolesterase FAF-X) (ubiquitin-specific processing protease FAF-X) (deubiquitinating enzyme FAF-X) (FAT FACETS protein related, X-linked).

Attorney Docket No. 5800–55

DbAcc: SP:Q93009
Species: *Homo sapiens*
Description: probable ubiquitin carboxyl-terminal hydrolase HAUSP (EC 3.1.2.15) (ubiquitin thiolesterase HAUSP) (ubiquitin-specific processing protease HAUSP) (deubiquitinating enzyme HAUSP) (herpesvirus associated ubiquitin-specific protease).

DbAcc: SP:Q14694
Species: *Homo sapiens*
Description: probable ubiquitin carboxyl-terminal hydrolase (EC 3.1.2.15) (ubiquitin thiolesterase) (ubiquitin-specific processing protease) (deubiquitinating enzyme) (KIAA0190).

DbAcc: SP:Q61068
Species: *Mus musculus*
Description: ubiquitin carboxyl-terminal hydrolase DUB-1 (EC 3.1.2.15) (ubiquitin thiolesterase DUB-1) (ubiquitin-specific processing protease DUB-1) (deubiquitinating enzyme 1).

DbAcc: SP:Q92353
Species: *Schizosaccharomyces pombe*
Description: putative ubiquitin carboxyl-terminal hydrolase C6G9.08 (EC 3.1.2.15) (ubiquitin thiolesterase) (ubiquitin-specific processing protease) (deubiquitinating enzyme).

DbAcc: GP:AF079564
Species: *Homo sapiens*
Description: UBP41 similar to *Gallus gallus* ubiquitin-specific DbAcc: GP:AC003974
Species: *Arabidopsis thaliana*
Description: F24L7.8

DbAcc: GP:AF040640
Species: *Caenorhabditis elegans*
Description: F09D1.1 similar to peptidase family C19 (ubiquitin DbAcc: SP:P43593
Species: *Saccharomyces cerevisiae*
Description: putative ubiquitin carboxyl-terminal hydrolase YFRO 1 OW (EC 3.1.2.15) (ubiquitin thiolesterase) (ubiquitin-specific processing protease) (deubiquitinating enzyme).

DbAcc: SP:Q01476
Species: *Saccharomyces cerevisiae*
Description: ubiquitin carboxyl-terminal hydrolase 2 (EC 3.1.2.15) (ubiquitin thiolesterase 2) (ubiquitin-specific processing protease 2) (deubiquitinating enzyme 2).

DbAcc: SP:Q24574
Species: *Drosophila melanogaster*
Description: ubiquitin carboxyl-terminal hydrolase 64e (EC 3.1.2.15) (ubiquitin thiolesterase 64E) (ubiquitin-specific processing protease 64E) (deubiquitinating enzyme 64E).

DbAcc: GP:AF126736
Species: *Homo sapiens*
Description: Ubp-M deubiquitinating enzyme homolog DbAcc: SP:P34547
Species: *Caenorhabditis elegans*
Description: probable ubiquitin carboxyl-terminal hydrolase $R_1$ OEI 1.3 (EC 3.1.2.15) (ubiquitin thiolesterase) (ubiquitin-specific processing protease) (deubiquitinating enzyme).

DbAcc: SP:P39538
Species: *Saccharomyces cerevisiae*
Description: ubiquitin carboxyl-terminal hydrolase 12 (EC 3.1.2.15) (ubiquitin thiolesterase 12) (ubiquitin-specific processing protease 12) (deubiquitinating enzyme 12).

DbAcc: SP:P39944
Species: *Saccharomyces cerevisiae*
Description: ubiquitin carboxyl-terminal hydrolase 5 (EC 3.1.2.15) (ubiquitin thiolesterase 5) (ubiquitin-specific processing protease 5) (deubiquitinating enzyme 5).

DbAcc: SP:P39967
Species: *Saccharomyces cerevisiae*
Description: ubiquitin carboxyl-terminal hydrolase 9 (EC 3.1.2.15) (ubiquitin thiolesterase 9) (ubiquitin-specific processing protease 9) (deubiquitinating enzyme 9).

DbAcc: SP:P50102
Species: *Saccharomyces cerevisiae*
Description: ubiquitin carboxyl-terminal hydrolase 8 (EC 3.1.2.15) (ubiquitin thiolesterase 8) (ubiquitin-specific processing protease 8) (deubiquitinating enzyme 8).

DbAcc: SP:P53874
Species: *Saccharomyces cerevisiae*
Description: ubiquitin carboxyl-terminal hydrolase 10 (EC 3.1.2.15) (ubiquitin thiolesterase 10) (ubiquitin-specific processing protease 10) (deubiquitinating enzyme 10).

DbAcc: SP:Q09738
Species: *Schizosaccharomyces pombe*
Description: putative ubiquitin carboxyl-terminal hydrolase C 13 AI 1.04C (EC 3.1.2.15) (ubiquitin thiolesterase) (ubiquitin-specific processing protease) (deubiquitinating enzyme).

DbAcc: GP:AL021838
Species: *Schizosaccharomyces pombe*
Description: 1251102 SPBC6B1.06c SPBC6B1.06c, ubiquitin carboxyl-terminal hydrolase, DbAcc: SP:P25037
Species: *Saccharomyces cerevisiae*
Description: ubiquitin carboxyl-terminal hydrolASE 1 (EC 3.1.2.15) (ubiquitin thiolesterase 1) (ubiquitin-specific processing protease 1) (deubiquitinating enzyme 1)

DbAcc: SP:P36026
  Species: *Saccharomyces cerevisiae*
Description: ubiquitin carboxyl-terminal hydrolase 11 (EC 3.1.2.15) (ubiquitin thiolesterase 11) (ubiquitin-specific processing protease 11) (deubiquitinating enzyme
DbAcc: SP:Q01477
  Species: *Saccharomyces cerevisiae*
Description: ubiquitin carboxyl-terminal hydrolase 3 (EC 3.1.2.15) (ubiquitin thiolesterase 3) (ubiquitin-specific processing protease 3) (deubiquitinating enzyme 3).
DbAcc: SP:Q02863
  Species: *Saccharomyces cerevisiae*
Description: ubiquitin carboxyl-terminal hydrolase 16 (EC 3.1.2.15) (ubiquitin thiolesterase 16) (ubiquitin-specific processing protease 16) (deubiquitinating enzyme 16).
DbAcc: SP:Q09931
  Species: *Caenorhabditis elegans*
Description: probable ubiquitin carboxyl-terminal hydrolase K02C4.3 (EC 3.1.2.15) (ubiquitin thiolesterase) (ubiquitin-specific processing protease) (deubiquitinating enzyme).
DbAcc: GP:Z81048
  Species: *Caenorhabditis elegans*
Description: 1344704 F30A10.10 similarity to human ubiquitin carboxyl-terminal
DbAcc: GP:Z66512
  Species: *Caenorhabditis elegans*
Description: 3877391 F52H3.3 951003
DbAcc: GP:U64844
  Species: *Caenorhabditis elegans*
Description: T22F3.2 coded for by *C. elegans* cDNA yk85c9.5
DbAcc: GP:U50193
  Species: *Caenorhabditis elegans*
Description: ZK328.1 coded for by *C. elegans* cDNA CEMSG95FB
DbAcc: GP:Z47812
  Species: *Caenorhabditis elegans*
Description: 1349023 T05H10.1 similar to ubiquitin carboxyl-terminal hydrolase;
- - -

HUNT SUMMARIES
Hunt Summary: Aspartyl (aspartyl proteases)
  Profiles/HMMs: 1
  TBLASTN: 15
- - -
HMM Probes for Aspartyl Proteases
  Name: asp
  Acc: PF00026
Description: Eukaryotic Aspartyl Protease
  Accession PF00026
  = = =
  ID asp
  AC PF00026
Eukaryotic Aspartyl Protease
  AU Eddy S R
  AL Clustalw
  SE Overington enriched
  GA 200
  TC 22.50 6.40
  NC 18.30 18.30
  BM hmmbuild -f HMM SEED
  BM hmmcalibrate—seed0HMM
  DR PROSITE; PDOC00128;
  DR PRINTS; PR00792;
  DC The Prosite entry also includes Pfam:PF00077.
  DR SCOP, 1mpp; fa;
  DC The following Pfam-B families contain sequences that according to Prodom
  DC are members of this Pfam-A family.
  DR PFAMB, PB000566;
  DR PFAMB; PB003851;
  DR PFAMB; PB035770;
  DR PFAMB; PB036097;
  DR PFAMB; PB036332;
  CC Aspartyl (acid) proteases include pepsins, cathepsins, and renins.
  CC Two-domain structure, probably arising from ancestral duplication.
  CC This family does not include the retroviral nor retrotransposon
  CC proteases (Pfam:PF00077), which are much smaller and appear to
  CC be homologous to a single domain of the eukaryotic asp proteases.
  SQ 218
- - -
Accession PDOC00128
= = =
- - -
TBLASTN Probes for Aspartyl Proteases
  DbAcc: SP:P00790
    Species: *Homo sapiens*
  Description: pepsinogen A precursor (EC 3.4.23. 1).
  DbAcc3 SP:P07339
    Species: *Homo sapiens*
  Description: cathepsin D precursor eC 3.4.23.5).
  DbAcc: SP:Q05744
    Species: *Gallus gallus*
  Description: cathepsin D precursor (EC 3.4.23.5).
  DbAcc: SP:P32834
    Species: *Schizosaccharomyces pombe*
  Description: aspartic proteinase SXA1 precursor (EC 3.4.23.-).
  DbAcc: SP:P40583
    Species: *Saccharomyces cerevisiae*
  Description: putative aspartyl proteinase YIR039C precursor (EC 3.4.23.-).
  DbAcc: SP:P53379
    Species: *Saccharomyces cerevisiae*
  Description: aspartic proteinase MKC7 precursor (EC 3.4.23.-). 5
  DbAcc: GP:AC005851
    Species: *Arabidopsis thaliana*
  Description: F24D 13.17
  DbAcc: SP:P12630
    Species: *Saccharomyces cerevisiae*
  Description: barrierpepsin precursor (EC 3.4.23.35) (extracellular barrier protein) (BAR proteinase).

DbAcc: SP:P28872
  Species: *Candida albicans*
  Description: candidapepsin 1 precursor (EC 3.4.23.24) (aspartate protease 1) (ACP 1) (secreted aspartic protease 1).
DbAcc: SP:P43096
  Species: *Candida albicans*
  Description: candidapepsin 7 precursor (EC 3.4.23.24) (aspartate protease 7) (ACP 7) (secreted aspartic protease 7).
DbAcc: SP:O42779
  Species: *Candida albicans*
  Description: candidapepsin 9 precursor (EC 3.4.23.24) (aspartate protease 9) (ACP 9) (secreted aspartic protease 9).
DbAcc: SP:P41748
  Species: *Aspergillus fumigatus*
  Description: aspergillopepsin F precursor (EC 3.4.23.18).
DbAcc: GP:U97000
  Species: *Caenorhabditis elegans*
  Description: F21F8.2 similar to eukaryotic aspartyl proteases
DbAcc: GP:AF016435
  Species: *Caenorhabditis elegans*
  Description: F59D6.3 similar to aspartyl protease
DbAcc: GP:U97000
  Species: *Caenorhabditis elegans*
  Description: F21F8.7 similar to eukaryotic aspartyl proteases

- - -

Hunt Summary: Caspase (caspase family of apoptosis regulating proteases)
  Profiles/Ms: 2
  TBLASTN: 16

- - -

HMM Probes for Caspase Family of Apoptosis Regulating Proteases
  Name: ICE_PIO
  Acc: PF00655
  Description: ICE-like protease (caspase) p10 domain
  Accession PF00655
  = = =
  ID ICE_p10
  AC PF00655
  ICE-like prot ease (caspase) p10 domain
  AU Bateman A
  AL pftools
  SE Prosite
  GA 25 25
  TC 26.40 26.40
  NC 7.30 7.30
  BM hmmbuild -f HMM SEED
  BM hmmcalibrate —seed0HM
  RN [1]
  RM 94309732
  RT Structure and mechanism of interleukin-1 beta converting
  RT enzyme.
  RA Wilson K P, Black J A, Thomson J A, Kim E E, Griffith J I), Navia
  RA M A, Murcko M A, Chambers S P, Aldape R A, Raybuck S A, et al.
  RL *Nature* (1994) 370:270–275.
  DC This is family C14 in the peptidase classification.
  DR MEROPS; C14;
  DR PROSITE_PROFILE; PS50207;
  DR PROSITE; PD0C00864;
  DR SCOP; lice; fa;
  SQ 48

- - -

Accession PD0C00864
= = =
Name: ICE_p20
Acc: PF00656
Description: ICE-like protease (caspase) p20 domain
Accession PF00656
= = =
ID ICE_p20
AC PF00656
ICE-like protease (caspase) p20 domain
AU Bateman A
AL Clustalw
SE Prosite
GA 25 25
TC 46.10 43.30
NC 7.00 7.00
BM hmmbuild -f HMM SEED
BM hmmcalibrate—seed0 HMM
RN [1]
RM 94309732
RT Structure and mechanism of interleukin-1 beta converting
RT enzyme.
RA Wilson K P, Black J A, Thomson J A, Kim E E, Griffith J P, Navia
RA M A, Murcko M A, Chambers S P, Aldape R A, Raybuck S A, et al.
RL *Nature* (1994) 370:270–275.
DC This is family C14 in the peptidase classification.
DR MEROPS; C14;
DR PROSITE_PROFLE; PS50208;
DR PROSITE; PDOC00864;
DR SCOP; lice; fa;
SQ 58

- - -

TBLASTN Probes for Caspase Family of Apoptosis Regulating Proteases
  DbAcc: SP:P29466
    Species: *Homo sapiens*
    Description: interleukin-1 beta convertase precursor (IL-1BC) (EC 3.4.22.36) (IL-1 beta converting enzyme) (ICE) (interleukin-1 beta converting enzyme) (P45) (caspase-1).
  DbAcc: SP:P49662
    Species: *Homo sapiens*
    Description: caspase-4 precursor (EC 3.4.22.-) (ICH-2 protease) (TX protease) (ICEREL-II).
  DbAcc: SP:P51878
    Species: *Homo sapiens*

Description: ICH-3 protease precursor (EC 3.4.22.-) (TY protease) (ICEREL-III).
DbAcc: SP:P42575
  Species: *Homo sapiens*
Description: caspase-2 precursor (EC 3.4.22.-) (ICH-1 protease) (ICH-1L/1S).
DbAcc: SP:P55210
  Species: *Homo sapiens*
Description: caspase-7 precursor (EC 3.4.22.-) (ICE-like apoptotic protease 3) (ICE-LAP3) (apoptotic protease MCH-3) (CMH-1).
DbAcc: SP:P55211
  Species: *Homo sapiens*
Description: caspase-9 precursor (EC 3.4.22.-) (ICE-like apoptotic protease 6) (ICE-LAP6) (apoptotic protease MCH-6).
DbAcc: SP:P55212
  Species: *Homo sapiens*
Description: apoptotic protease MCH-2 precursor (EC 3.4.22.-).
DbAcc: SP:P42574
  Species: *Homo sapiens*
Description: apopain precursor (EC 3.4.22.-) (cysteine protease CPP32) (YAMA protein).
DbAcc: SP:Q15121
  Species: *Homo sapiens*
Description: astrocytic phosphoprotein PEA-15.
DbAcc: SP:Q92851
  Species: *Homo sapiens*
Description: caspase-10 precursor (EC 3.4.22.-) (ICE-like apoptotic protease 4) (apoptotic protease MCH-4) (FAS-associated death domain protein interleukin-1B-converting enzyme 2) (FLICE2).
DbAcc: SP:Q14790
  Species: *Homo sapiens*
Description: caspase-8 precursor (EC 3.4.22.-) (ICE-like apoptotic protease 5) (MORT1-associated CED-3 homolog) (MACH) (FADD-homologous ICE/CED-3-like protease) (FADD-like ICE) (FLICE) (apoptotic cysteine protease) (apoptotic protease MCH-5) (CAP4).
DbAcc: SP:P42573
  Species: *Caenorhabditis elegans*
Description: cell death protein 3 precursor (EC 3.4.22.-).
DbAcc: GP:AF010127
  Species: *Homo sapiens*
Description: casper
DbAcc: GP:AJ007750
  Species: *Mus musculus*
Description: 3550510 caspase- 14
DbAcc: GP:AF001464
  Species: *Drosophila melanogaster*
Description: caspase-1
DbAcc: GP:AF097874
  Species: *Homo sapiens*
Description: caspase 14 precursor
- - -
Hunt Summary: m17 (peptidase family m17)
  Profiles/HMMs: 1
  TBLASTN: 5
- - -
HMM Probes for Peptidase Family m17
  Name: Peptidase_M17
  Acc: PF00883
  Description: Cytosol Aminopeptidase Family
  Accession PF00883
= = =
ID Peptidase_M17
AC PF00883
Cytosol aminopeptidase family
AU Bateman A
AL Clustalw
SE Pfam-B_990 (release 3.0)
GA 10 10
TC 11.60 11.60
NC −260.90−260.90
BM hmmbuild −F HMM SEED
BM hmmcalibrate—seed 0 HMM
DR SCOP; 11am; fa,
DR PROSITE; PDOC00548;
DC This family belongs to family M17 of the peptidase classification.
DR MEROPS; M17;
SQ 30
- - -
Accession PDOC00548
= = =
- - -
TBLASTN Probes for Peptidase Family m17
  DbAcc: GP:AF061738
    Species: *Homo sapiens*
  Description: leucine aminopeptidase
  DbAcc: SP:P34629
    Species: *Caenorhabditis elegans*
  Description: putative aminopeptidase ZK353.6 in chromosome III (EC 3.4.11.-).
  DbAcc: SP:P37095
    Species: *Escherichia coli*
  Description: peptidase B
  DbAcc: SP:P30184
    Species: *Arabidopsis thaliana*
  Description: cytosol aminopeptidase (EC 3.4.11.1) (leucine aminopeptidase) (LAP) (leucyl aminopeptidase) (proline aminopeptidase) (EC 3.4.11.5) (prolyl aminopeptidase).
  DbAcc: GP:Z78018
    Species: *Caenorhabditis elegans*
  Description: 3880567 W07G4.4 Identity to *C. elegans* protein WP:W07A12.3; cDNA EST
- - -
Hunt Summary: Prolyloligo (prolyl oligopeptidases)
  ProfilesHMMs: 2
  TBLASTN: 5
- - -
HMM Probes for Prolyl Oligopeptidases
  Name: DPPIV_N_term
  Acc: PF00930
Description: Dipeptidyl peptidase IV (DPP IV) N-terminal region
  Accession PF00930

= = =
ID DPPIV_N_term
AC PF00930
Dipeptidyl peptidase IV (DPP IV) N-terminal region
AU Finn R D, Bateman A
AL Clustalw
SE Pfam-B_1017 (release 3.0)
GA –114 –114
TC 18.20 18.20
NC –168.70 –168.70
BM hmmbuild –F HMM SEED
BM hmmcalibrate —seed0 HMM
DR PROSITE; PDOC00587;
DC The following Pfam-B family may contain sequences that according to Prodom
DC are members of this Pfam-A family.
DR PFAMB; PB036169,
CC This family is an alignment of the region to the
CC N-terminal side of the active site.
CC The Prosite motif does not correspond to this Pfam entry.
SQ 23
- - -
Accession PDOC00587
= = =
Name: Peptidase_S9
Acc: PF00326
Description: Prolyl Oligopeptidase Family
Accession PF00326
= = =
ID Peptidase_S9
AC PF00326
Prolyl oligopeptidase family
PI Prolyl oligopep;
AU Finn R D
AL Clustalw
SE Prosite
GA 12.8 12.8
TC 12.90 12.90
NC 12.50 12.50
BM hmmbuild –f HMM SEED
BM hmmcalibrate—seed0 HMM
DC This family belongs to family S9 of the peptidase classification.
DR MEROPS; S9;
DR PROSITE; PDOC00587;
SQ 53
- - -
TBLASTN Probes for Prolyl Oligopeptidases
DbAcc: SP:P48147
Species: *Homo sapiens*
Description: prolyl endopeptidase (EC 3.4.21.26) (post-proline cleaving enzyme) (PE).
DbAcc: SP:P28843
Species: *Mus musculus*
Description: dipeptidyl peptidase IV (EC 3.4.14.5) (DPP IV) (thymocyte-activating molecule) (THAM).
DbAcc: SP:P42658
Species: *Homo sapiens*
Description: dipeptidyl peptidase IV like protein (dipeptidyl aminopeptidase- related protein) (dipeptidylpeptidase VI) (DPPX-L/DPPX-S).
DbAcc: SP:P33894
Species: *Saccharomyces cerevisiae*
Description: dipeptidyl aminopeptidase A (EC 3.4.14.-) (DPAP A) (YSCIV).
DbAcc: SP:P18962
Species: *Saccharomyces cerevisiae*
Description: dipeptidyl aminopeptidase B (EC 3.4.14.-) (DPAP B) (YSCV).
- - -
Hunt Summary: Renaldipep
ProfileslHMMs: 1
TBLASTN: 1
- - -
HMM Probes for Renaldipep
Name: Renal_dipeptase
Acc: PF01244
Description: Renal Dipeptidase
Accession PF01244
= = =
ID Renal dipeptase
AC PF01244
Renal dipeptidase
AU Finn R D, Bateman A
AL Clustalw
SE Prosite
GA 25 25
TC 271.60 271.60
NC –28.90–28.90
BM hmmbuild –F HMM SEED
BM hmmcalibrate—seed0 H
DR PROSITE; PDOC00678;
DC The following Pfam-B families contain sequences that according to Prodom
DC are members of this Pfam-A family.
DR PFAMB; PB012247;
DR PFAMB, PB019330;
SQ 8
- - -
Accession PDOC00678
= = =
- - -
TBLASTN Probes for Renaldipep
Mineld: 6453
DbAcc: SP:P16444
Species: *Homo sapiens*
Description: microsomal dipeptidase precursor (EC 3.4.13.19) (MDP) (dehydropeptidase-i) (renal dipeptidase) (RDP).
- - -
Hunt Summary: Reprolysin (ADAM family of metalloprotease)
Profiles/HMMs: 1
TBLASTN: 24
- - -
HMM Probes for ADAM Family of Metalloprotease Name: Reprolysin
Acc: PF01421
Description: Reprolysin (M12B) Family Zinc Metalloprotease
Accession PF01421
= = =
ID Reprolysin
AC PF01421
Reprolysin (M12B) family zinc metalloprotease
AU Bateman A
AL Clustalw
SE Swissprot
GA −100–100
TC −96.50 −96.50
NC −111.80–111.80
BM hmmbuild HMM SEED
BM hmmcalibrate—seed0HMM
RN [1]
RM 95405261
RT Evolutionary families of metallopeptidases.
RA Rawlings N D, Barrett A J,
RL Meth Enzymol 1995,248:183–228.
DC This Prosite motif covers only the active site.
DR PROSITE; PDOC00129:
DR SCOP; last; fa;
DC This is family M12B in the peptidase classification.
DR MEROPS; M12;
DC The following Pfam-B families contain sequences that according to Prodom
DC are members of this Pfam-A family.
DR PFAMB; PB016125;
DR PFAMB; PB031186;
DR PFAMB; PB035940;
DR PFAMB; PB036263;
CC The members of this family are enzymes that cleave peptides.
CC These proteases require zinc for catalysis. Members of this
CC family are also known as adamalysins.
CC Most members of this family are snake venom endopeptidases,
CC but there are also some mammalian proteins such as Swiss:P78325,
CC and fertilin Swiss:Q28472. Fertilin and closely related
CC proteins appear to not have some active site residues and
CC may not be active enzymes.
SQ 115
- - -
Accession PDOC00129
= = =
- - -
TBLASTN Probes for ADAM Family of Metalloprotease
DbAcc: SP:Q05910
Species: *Mus musculus*
Description: cell surface antigen MS2 precursor (EC 3.4.24.-) (macrophage cysteine-rich glycoprotein).
DbAcc: GP:U41767
Species: *Homo sapiens*
Description: metargidin precursor
DbAcc: GP:AF009615
Species: *Homo sapiens*
Description: disintegrin-metalloprotease MADM
DbAcc: GP:AJ242015
Species: *Homo sapiens*
Description: 4757044 eMDC II protein
DbAcc: GP:D31872
Species: *Homo sapiens*
Description: 836684 metalloprotease/disintegrin-like protein
DbAcc: GP:D67076
Species: *Mus musculus*
Description: 1813340 secretory protein containing thrombospondin
DbAcc: SP:P78325
Species: *Homo sapiens*
Description: cell surface antigen MS2 precursor (EC 3.4.24.-) (CD156 antigen).
DbAcc: GP:AF019887
Species: *Mus musculus*
Description: metalloprotease-disintegrin meltrin beta
DbAcc: GP:U22058
Species: *Mus musculus*
Description: ADAM 4 protein precursor
DbAcc: GP:AF029899
Species: *Homo sapiens*
Description: ADAM 20
DbAcc: GP:AF006196
Species: *Mus musculus*
Description: metalloprotease-disintegrin MDC 15
DbAcc: GP:AJ012603
Species: *Rattus rattus*
Description: 1340857 TNF-alpha converting enzyme (TACE)
DbAcc: GP:AB009672
Species: *Homo sapiens*
Description: 3419878 MDC3
DbAcc: GP:X77619
Species: *Macaca macaca*
Description: tMDC II
DbAcc: GP:Y13323
Species: *Homo sapiens*
Description: 2370107 disintegrin-protease
DbAcc: GP:U68185
Species: *Caenorhabditis elegans*
Description: adm-1 domain organization is identical to PH-30/fertilin
DbAcc: GP:U42846
Species: *Caenorhabditis elegans*
Description: T19D2.1 coded for by *C. elegans* cDNA yk126d9.3
DbAcc: GP:Z81460
Species: *Caenorhabditis elegans*
Description: 3873969 C04A11.4 Similarity to Mouse meltrin alpha protein
DbAcc: SP:O13766
Species: *Schizosaccharomyces pombe*
Description: probable zinc metallopeptidase C17A5.04C precursor (EC 3.4.24.-).

DbAcc: GP:Y10615
 Species: *Homo sapiens*
Description: 2198473 CYRN2 member of ADAM family
DbAcc: GP:AJ010688
 Species: *Mus musculus*
Description: 1320044 Cyrn1
DbAcc: GP:AF032383
 Species: *Xenopus laevis*
Description: MDC11b DbAcc: GP:U78185
 Species: *Xenopus laevis*
Description: xMDC16
DbAcc: SP:P30403
 Species: *Agkistrodon rhodostoma*
Description: hemorrhagic protein-rhodostomin precursor (EC 3.4.24.-) (RHO) [contains: disintegrin rhodostomin].

That which is claimed:

1. An isolated nucleic acid molecule having the nucleotide sequence shown in SEQ ID NO:1 or a complement thereof.

* * * * *